(12) United States Patent
Fisher et al.

US012325863B2

(10) Patent No.: US 12,325,863 B2
(45) Date of Patent: Jun. 10, 2025

(54) MDA-7/IL-24 SECRETORY VARIANTS AND METHODS OF USE

(71) Applicant: Virginia Commonwealth University, Richmond, VA (US)

(72) Inventors: Paul B. Fisher, Henrico, VA (US); Mitchell E. Menezes, Richmond, VA (US); Praveen Bhoopathi, Richmond, VA (US); Swadesh K Das, Richmond, VA (US); Luni Emdad, Richmond, VA (US); Devanand Sarkar, Richmond, VA (US); Anjan K. Pradhan, Richmond, VA (US); Xiang-Yang Wang, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1359 days.

(21) Appl. No.: 16/963,529

(22) PCT Filed: Jan. 23, 2019

(86) PCT No.: PCT/US2019/014686
§ 371 (c)(1),
(2) Date: Jul. 21, 2020

(87) PCT Pub. No.: WO2019/147623
PCT Pub. Date: Aug. 1, 2019

(65) Prior Publication Data
US 2020/0354745 A1    Nov. 12, 2020

Related U.S. Application Data

(60) Provisional application No. 62/620,649, filed on Jan. 23, 2018, provisional application No. 62/620,673, filed on Jan. 23, 2018.

(51) Int. Cl.
| | |
|---|---|
| *C12N 15/86* | (2006.01) |
| *A61K 31/5377* | (2006.01) |
| *A61K 35/17* | (2015.01) |
| *A61K 38/00* | (2006.01) |
| *A61K 39/00* | (2006.01) |
| *A61P 35/00* | (2006.01) |
| *C07K 14/54* | (2006.01) |
| *C07K 14/62* | (2006.01) |

(52) U.S. Cl.
CPC .......... *C12N 15/86* (2013.01); *A61K 31/5377* (2013.01); *A61K 35/17* (2013.01); *A61K 39/4611* (2023.05); *A61K 39/4635* (2023.05); *A61K 39/4644* (2023.05); *A61P 35/00* (2018.01); *C07K 14/54* (2013.01); *C07K 14/62* (2013.01); *A61K 38/00* (2013.01); *A61K 2239/31* (2023.05); *A61K 2239/49* (2023.05); *A61K 2239/55* (2023.05); *A61K 2239/58* (2023.05)

(58) Field of Classification Search
CPC .......... C12N 15/86; C12N 2710/10343; A61K 31/5377; A61K 35/17; A61K 38/00; A61K 2239/55; A61K 2239/58; A61K 39/4611; A61K 39/4635; A61K 39/4644; A61K 2239/31; A61K 2239/49; A61K 48/00; A61P 35/00; C07K 14/54; C07K 14/62
See application file for complete search history.

(56) References Cited

U.S. PATENT DOCUMENTS

| | | | |
|---|---|---|---|
| 9,175,048 B2 * | 11/2015 | Lenormand | C07K 14/4702 |
| 2004/0234531 A1 * | 11/2004 | Casares | A61P 37/00 530/391.1 |
| 2006/0062772 A1 | 3/2006 | Keegan et al. | |
| 2006/0292157 A1 | 12/2006 | Fisher et al. | |
| 2006/0292457 A1 * | 12/2006 | Fisher | |
| 2007/0009484 A1 | 1/2007 | Hunt et al. | |
| 2008/0242603 A1 * | 10/2008 | Wang | C07K 14/54 435/348 |
| 2009/0053244 A1 | 2/2009 | Chen et al. | |
| 2012/0237533 A1 | 9/2012 | Kulik et al. | |
| 2014/0235702 A1 | 8/2014 | Nikolovska-Coleska et al. | |

FOREIGN PATENT DOCUMENTS

WO    WO-93/18157 A1    9/1993

OTHER PUBLICATIONS

Sauane (Oncogene 23.46 (2004): 7679-7690) (Year: 2004).*
Sauane (Journal of cellular physiology 196.2 (2003): 334-345) (Year: 2003).*
Goldfine (Endocrine Reviews 8.3 (1987): 235-255) (Year: 1987).*
Boelens (In Vivo 21.2 (2007): 215-226) (Year: 2007).*
Su (Proceedings of the National Academy of Sciences 102.4 (2005): 1059-1064) (Year: 2005).*
International Search Report and Written Opinion dated Oct. 2, 2019 issued in International Application No. PCT/US2019/014686.

(Continued)

*Primary Examiner* — Nancy J Leith
*Assistant Examiner* — Kyle T Rega
(74) *Attorney, Agent, or Firm* — Goodwin Procter LLP

(57) ABSTRACT

In various aspects, the present disclosure provides polynucleotides encoding a fusion protein, as well as vectors, cells, and compositions comprising the same. In embodiments, the fusion protein includes an insulin signal peptide and an MDA-7/IL-24 protein. Methods of using the polynucleotides, vectors, cells, and compositions, such as in the treatment or prevention of cancer, are also provided.

33 Claims, 31 Drawing Sheets
Specification includes a Sequence Listing.

(56) References Cited

OTHER PUBLICATIONS

Tian, Hui et al, "Critical Role of Lysine 123 in the Ubiquitin-Mediated Degradation of MDA-7/IL-24," Journal of Interferon & Cytokine Research, vol. 32, No. 12, 2012.
F. Wei et al., "The Alarmin HMGN1 Contributes to Antitumor Immunity and Is a Potent Immunoadjuvant," Cancer Research, vol. 74, No. 21, Sep. 9, 2014, pp. 5989-5998, XP055376833.
Pradhan, Anjan K. et al., "Enhanced Cancer Therapy Using an Engineered Designer Cytokine Alone and in Combination With an Immune Checkpoint Inhibitor", Frontiers in Oncology, Mar. 2022, vol. 12, Article 812560, doi.org/10.3389/fonc.2022.812560 <https://doi.org/10.3389/fonc.2022.812560>.

\* cited by examiner

Decorated MB

SEQUENCE LISTING

<160> NUMBER OF SEQ ID NOS: 20

<210> SEQ ID NO 1
<211> LENGTH: 621
<212> TYPE: DNA
<213> ORGANISM: Artificial sequence
<220> FEATURE:
<223> OTHER INFORMATION: Synthetic polynucleotide

<400> SEQUENCE: 1

```
atgaattttc aacagaggct gcaaagcctg tggactttag ccagacccTT ctgccctcct    60
ttgctggcga cagcctctca aatgcagatg gttgtgctcc cttgcctggg ttttaccctg    120
cttctctgga gccaggtatc aggggcccag ggccaagaat tccactttgg gccctgccaa    180
gtgaagggg ttgttcccca gaaactgtgg gaagccttct gggctgtgaa agacactatg    240
caagctcagg ataacatcac gagtgcccgg ctgctgcagc aggaggttct gcagaacgtc    300
tcggatgctg agagctgtta ccttgtccac accctgctgg agttctactt gaaaactgtt    360
ttcaaaaact accacaatag aacagttgaa gtcaggactc tgaagtcatt ctctactctg    420
gccaacaact ttgttctcat cgtgtcacaa ctgcaaccca gtcaagaaaa tgagatgttt    480
tccatcagag acagtgcaca caggcggttc ctgctattcc ggagagcatt taaacagttg    540
gacgtagaag cagctctgac caaagcccTT ggggaagtgg acattcttct gacctggatg    600
cagaaattct acaagctctg a                                              621
```

<210> SEQ ID NO 2
<211> LENGTH: 206
<212> TYPE: PRT
<213> ORGANISM: Artificial sequence
<220> FEATURE:
<223> OTHER INFORMATION: Synthetic polypeptide

<400> SEQUENCE: 2

```
Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
            20                  25                  30

Leu Pro Cys Leu Gly Phe Thr Leu Leu Leu Trp Ser Gln Val Ser Gly
        35                  40                  45

Ala Gln Gly Gln Glu Phe His Phe Gly Pro Cys Gln Val Lys Gly Val
    50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Gln Glu Val
                85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
    130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190
```

```
Val Asp Ile Leu Leu Thr Trp Met Gln Lys Phe Tyr Lys Leu
        195                 200                 205

<210> SEQ ID NO 3
<211> LENGTH: 157
<212> TYPE: PRT
<213> ORGANISM: Artificial sequence
<220> FEATURE:
<223> OTHER INFORMATION: Synthetic polypeptide

<400> SEQUENCE: 3

Gln Gly Gln Glu Phe His Phe Gly Pro Cys Gln Val Lys Gly Val Val
1               5                   10                  15

Pro Gln Lys Leu Trp Glu Ala Phe Trp Ala Val Lys Asp Thr Met Gln
            20                  25                  30

Ala Gln Asp Asn Ile Thr Ser Ala Arg Leu Leu Gln Gln Glu Val Leu
        35                  40                  45

Gln Asn Val Ser Asp Ala Glu Ser Cys Tyr Leu Val His Thr Leu Leu
    50                  55                  60

Glu Phe Tyr Leu Lys Thr Val Phe Lys Asn Tyr His Asn Arg Thr Val
65                  70                  75                  80

Glu Val Arg Thr Leu Lys Ser Phe Ser Thr Leu Ala Asn Asn Phe Val
                85                  90                  95

Leu Ile Val Ser Gln Leu Gln Pro Ser Gln Glu Asn Glu Met Phe Ser
            100                 105                 110

Ile Arg Asp Ser Ala His Arg Arg Phe Leu Leu Phe Arg Arg Ala Phe
        115                 120                 125

Lys Gln Leu Asp Val Glu Ala Ala Leu Thr Lys Ala Leu Gly Glu Val
    130                 135                 140

Asp Ile Leu Leu Thr Trp Met Gln Lys Phe Tyr Lys Leu
145                 150                 155

<210> SEQ ID NO 4
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 4

Glu Ser Cys Tyr Leu Val His Thr Leu Leu Glu Phe Tyr Leu Lys Thr
1               5                   10                  15

Val Phe Lys Asn Tyr His Asn Arg Thr Val Glu Val Arg Thr Leu Lys
            20                  25                  30

Ser Phe Ser Thr Leu Ala Asn Asn Phe Val Leu Ile Val Ser Gln Leu
        35                  40                  45

Gln Pro Ser Gln Glu Asn Glu Met Phe Ser Ile Arg Asp Ser Ala His
    50                  55                  60

Arg Arg Phe Leu Leu Phe Arg Arg Ala Phe Lys Gln Leu Asp Val Glu
65                  70                  75                  80

Ala Ala Leu Thr Lys Ala Leu Gly Glu Val Asp Ile Leu Leu Thr Trp
                85                  90                  95

Met Gln Lys Phe Tyr Lys Leu
            100

<210> SEQ ID NO 5
<211> LENGTH: 24
<212> TYPE: PRT
```

<213> ORGANISM: Artificial sequence
<220> FEATURE:
<223> OTHER INFORMATION: Synthetic polypeptide

<400> SEQUENCE: 5

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 6
<211> LENGTH: 582
<212> TYPE: DNA
<213> ORGANISM: Artificial sequence
<220> FEATURE:
<223> OTHER INFORMATION: Synthetic polynucleotide

<400> SEQUENCE: 6

```
atggcgctgt ggatgcgcct gctgccgctg ctggcgctgc tggcgctgtg gggcccagat      60
ccggcggcgg cgcatcacca tcaccatcac gagaacctgt acttccaggg catgcaagaa     120
ttccactttg gccctgcca agtgaagggg gttgttcccc agaaactgtg gaagccttc      180
tgggctgtga agacactat gcaagctcag gataacatca cgagtgcccg gctgctgcag     240
caggaggttc tgcagaacgt ctcggatgct gagagctgtt accttgtcca caccctgctg     300
gagttctact tgaaaactgt tttcaaaaac taccacaata gaacagttga agtcaggact     360
ctgaagtcat tctctactct ggccaacaac tttgttctca tcgtgtcaca actgcaaccc     420
agtcaagaaa tgagatgtt ttccatcaga cagtgcac acaggcggtt cctgctattc     480
cggagagcat tcaaacagtt ggacgtagaa gcagctctga ccaaagccct ggggaagtg     540
gacattcttc tgacctggat gcagaaattc tacaagctct ag                       582
```

<210> SEQ ID NO 7
<211> LENGTH: 567
<212> TYPE: DNA
<213> ORGANISM: Artificial sequence
<220> FEATURE:
<223> OTHER INFORMATION: Synthetic polynucleotide

<400> SEQUENCE: 7

```
atgacagtgc tggcgccagc ctggagccca acaacctatc tcctcctgct gctgctgctg      60
agcggatcca tgcaagaatt ccactttggg ccctgccaag tgaaggggt tgttccccag     120
aaactgtggg aagccttctg gctgtgaaa gacactatgc aagctcagga taacatcacg     180
agtgcccggc tgctgcagca ggaggttctg cagaacgtct cggatgctga gagctgttac     240
cttgtccaca ccctgctgga gttctacttg aaaactgttt tcaaaaacta ccacaataga     300
acagttgaag tcaggactct gaagtcattc tctactctgg ccaacaactt tgttctcatc     360
gtgtcacaac tgcaacccag tcaagaaat gagatgtttt ccatcagaga cagtgcacac     420
aggcggtttc tgctattccg gagagcattc aaacagttgg acgtagaagc agctctgacc     480
aaagcccttg ggaagtgga cattcttctg acctggatgc agaaattcta caagctcggg     540
ggttctcatc atcatcatca tcattga                                        567
```

<210> SEQ ID NO 8
<211> LENGTH: 561
<212> TYPE: DNA
<213> ORGANISM: Artificial sequence
<220> FEATURE:
<223> OTHER INFORMATION: Synthetic polynucleotide

<400> SEQUENCE: 8

| | | |
|---|---|---|
| atgagagcct ggatctttt tctgctctgc ctcgctggca gagccctggc tcatcaccat | 60 |
| caccatcacg agaacctgta cttccagggc atgcaagaat ccactttgg gccctgccaa | 120 |
| gtgaagggg ttgttcccca gaaactgtgg gaagccttct gggctgtgaa agacactatg | 180 |
| caagctcagg ataacatcac gagtgcccgg ctgctgcagc aggaggttct gcagaacgtc | 240 |
| tcggatgctg agagctgtta ccttgtccac accctgctgg agttctactt gaaaactgtt | 300 |
| ttcaaaaact accacaatag aacagttgaa gtcaggactc tgaagtcatt ctctactctg | 360 |
| gccaacaact ttgttctcat cgtgtcacaa ctgcaaccca gtcaagaaaa tgagatgttt | 420 |
| tccatcagag acagtgcaca caggcggttt ctgctattcc ggagagcatt caaacagttg | 480 |
| gacgtagaag cagctctgac caaagccct ggggaagtgg acattcttct gacctggatg | 540 |
| cagaaattct acaagctctg a | 561 |

<210> SEQ ID NO 9
<211> LENGTH: 513
<212> TYPE: DNA
<213> ORGANISM: Artificial sequence
<220> FEATURE:
<223> OTHER INFORMATION: Synthetic polynucleotide

<400> SEQUENCE: 9

| | | |
|---|---|---|
| atgcagctgc tgtcatgcat cgcattgatc ttggcgctgg tgatgcaaga attccacttt | 60 |
| gggccctgcc aagtgaaggg ggttgttccc cagaaactgt gggaagcctt ctgggctgtg | 120 |
| aaagacacta tgcaagctca ggataacatc acgagtgccc ggctgctgca gcaggaggtt | 180 |
| ctgcagaacg tctcggatgc tgagagctgt taccttgtcc acaccctgct ggagttctac | 240 |
| ttgaaaactg ttttcaaaaa ctaccacaat agaacagttg aagtcaggac tctgaagtca | 300 |
| ttctctactc tggccaacaa ctttgttctc atcgtgtcac aactgcaacc cagtcaagaa | 360 |
| aatgagatgt tttccatcag agacagtgca cacaggcggt ttctgctatt ccggagagca | 420 |
| ttcaaacagt tggacgtaga agcagctctg accaaagccc ttggggaagt ggacattctt | 480 |
| ctgacctgga tgcagaaatt ctacaagctc tga | 513 |

<210> SEQ ID NO 10
<211> LENGTH: 621
<212> TYPE: DNA
<213> ORGANISM: Artificial sequence
<220> FEATURE:
<223> OTHER INFORMATION: Synthetic polynucleotide

<400> SEQUENCE: 10

| | | |
|---|---|---|
| atgaattttc aacagaggct gcaaagcctg tggactttag ccagacccct ctgccctcct | 60 |
| ttgctggcga cagcctctca aatgcagatg gttgtgctcc cttgcctggg ttttaccctg | 120 |
| cttctctgga gccaggtatc aggggcccag ggccaagaat ccactttgg gccctgccaa | 180 |
| gtgaagggg ttgttcccca gaaactgtgg gaagccttct gggctgtgaa agacactatg | 240 |
| caagctcagg ataacatcac gagtgcccgg ctgctgcagc aggaggttct gcagaacgtc | 300 |
| tcggatgctg agagctgtta ccttgtccac accctgctgg agttctactt gaaaactgtt | 360 |
| ttcagaaact accacaatag aacagttgaa gtcaggactc tgaagtcatt ctctactctg | 420 |
| gccaacaact ttgttctcat cgtgtcacaa ctgcaaccca gtcaagaaaa tgagatgttt | 480 |
| tccatcagag acagtgcaca caggcggttt ctgctattcc ggagagcatt caaacagttg | 540 | gacgtagaag cagctctgac caaagcccctt ggggaagtgg acattcttct gacctggatg    600 cagaaattct acaagctctg a    621

<210> SEQ ID NO 11
<211> LENGTH: 582
<212> TYPE: DNA
<213> ORGANISM: Artificial sequence
<220> FEATURE:
<223> OTHER INFORMATION: Synthetic polynucleotide

<400> SEQUENCE: 11
atggcgctgt ggatgcgcct gctgccgctg ctggcgctgc tggcgctgtg gggcccagat    60
ccggcggcgg cgcatcacca tcaccatcac gagaacctgt acttccaggg catgcaagaa    120
ttccactttg ggccctgcca agtgaagggg gttgttcccc agaaactgtg gaagccttc    180 tgggctgtga agacactat gcaagctcag ataacatca cgagtgcccg gctgctgcag    240
caggaggttc tgcagaacgt ctcggatgct gagagctgtt accttgtcca caccctgctg    300
gagttctact tgaaaactgt tttcagaaac taccacaata gaacagttga agtcaggact    360
ctgaagtcat tctctactct ggccaacaac tttgttctca cgtgtcaca actgcaaccc    420 agtcaagaaa atgagatgtt ttccatcaga gacagtgcac acaggcggtt cctgctattc    480
cggagagcat tcaaacagtt ggacgtagaa gcagctctga ccaaagcccct ggggaagtg    540 gacattcttc tgacctggat gcagaaattc tacaagctct ag    582

<210> SEQ ID NO 12
<211> LENGTH: 426
<212> TYPE: DNA
<213> ORGANISM: Artificial sequence
<220> FEATURE:
<223> OTHER INFORMATION: Synthetic polynucleotide

<400> SEQUENCE: 12
atggcgctgt ggatgcgcct gctgccgctg ctggcgctgc tggcgctgtg gggcccagat    60
ccggcggcgg cgcatcacca tcaccatcac gagaacctgt acttccaggg catggagagc    120
tgttaccttg tccacaccct gctggagttc tacttgaaaa ctgttttcaa aaactaccac    180
aatagaacag ttgaagtcag gactctgaag tcattctcta ctctggccaa caactttgtt    240
ctcatcgtgt cacaactgca acccagtcaa gaaaatgaga tgttttccat cagagacagt    300
gcacacaggc ggttcctgct attccggaga gcattcaaac agttggacgt agaagcagct    360
ctgaccaaag cccttgggga gtggacattc ttctgacct ggatgcagaa attctacaag    420
ctctag    426

<210> SEQ ID NO 13
<211> LENGTH: 357
<212> TYPE: DNA
<213> ORGANISM: Artificial sequence
<220> FEATURE:
<223> OTHER INFORMATION: Synthetic polynucleotide

<400> SEQUENCE: 13
atgcagctgc tgtcatgcat cgcattgatc ttggcgctgg tgatggagag ctgttacctt    60
gtccacaccc tgctggagtt ctacttgaaa actgttttca aaaactacca caatagaaca    120
gttgaagtca ggactctgaa gtcattctct actctggcca acaactttgt tctcatcgtg    180
tcacaactgc aacccagtca agaaaatgag atgttttcca tcagagacag tgcacacagg    240
cggtttctgc tattccggag agcattcaaa cagttggacg tagaagcagc tctgaccaaa    300
gcccttgggg aagtggacat tcttctgacc tggatgcaga aattctacaa gctctga     357

<210> SEQ ID NO 14
<211> LENGTH: 408
<212> TYPE: DNA
<213> ORGANISM: Artificial sequence
<220> FEATURE:
<223> OTHER INFORMATION: Synthetic polynucleotide

<400> SEQUENCE: 14
atgacagtgc tggcgccagc ctggagccca acaacctatc tcctcctgct gctgctgctg     60
agcggatccg agagctgtta ccttgtccac accctgctgg agttctactt gaaaactgtt     120
ttcaaaaact accacaatag aacagttgaa gtcaggactc tgaagtcatt ctctactctg     180
gccaacaact ttgttctcat cgtgtcacaa ctgcaaccca gtcaagaaaa tgagatgttt     240
tccatcagag acagtgcaca caggcggttt ctgctattcc ggagagcatt caaacagttg     300
gacgtagaag cagctctgac caaagccctt ggggaagtgg acattcttct gacctggatg     360
cagaaattct acaagctcgg gggttctcat catcatcatc atcattga     408

<210> SEQ ID NO 15
<211> LENGTH: 471
<212> TYPE: DNA
<213> ORGANISM: Artificial sequence
<220> FEATURE:
<223> OTHER INFORMATION: Synthetic polynucleotide

<400> SEQUENCE: 15
atgaattttc aacagaggct gcaaagcctg tggactttag ccagaccctt ctgccctcct     60
ttgctggcga cagcctctca aatgcagatg gttgtgctcc cttgcctggg ttttacccctg     120 cttctctgga gccaggtatc aggggcccag ggcggatccg agagctgtta ccttgtccac     180
accctgctgg agttctactt gaaaactgtt ttcaaaaact accacaatag aacagttgaa     240
gtcaggactc tgaagtcatt ctctactctg gccaacaact ttgttctcat cgtgtcacaa     300
ctgcaaccca gtcaagaaaa tgagatgttt tccatcagag acagtgcaca caggcggttt     360
ctgctattcc ggagagcatt caaacagttg gacgtagaag cagctctgac caaagccctt     420
ggggaagtgg acattcttct gacctggatg cagaaattct acaagctctg a     471

<210> SEQ ID NO 16
<211> LENGTH: 408
<212> TYPE: DNA
<213> ORGANISM: Artificial sequence
<220> FEATURE:
<223> OTHER INFORMATION: Synthetic polynucleotide

<400> SEQUENCE: 16
atgacagtgc tggcgccagc ctggagccca acaacctatc tcctcctgct gctgctgctg     60
agcggatccg agagctgtta ccttgtccac accctgctgg agttctactt gaaaactgtt     120
ttcagaaact accacaatag aacagttgaa gtcaggactc tgaagtcatt ctctactctg     180
gccaacaact ttgttctcat cgtgtcacaa ctgcaaccca gtcaagaaaa tgagatgttt     240
tccatcagag acagtgcaca caggcggttt ctgctattcc ggagagcatt caaacagttg     300
gacgtagaag cagctctgac caaagccctt ggggaagtgg acattcttct gacctggatg     360
cagaaattct acaagctcgg gggttctcat catcatcatc atcattga     408

<210> SEQ ID NO 17

```
<211> LENGTH: 426
<212> TYPE: DNA
<213> ORGANISM: Artificial sequence
<220> FEATURE:
<223> OTHER INFORMATION: Synthetic polynucleotide

<400> SEQUENCE: 17
atggcgctgt ggatgcgcct gctgccgctg ctggcgctgc tggcgctgtg gggcccagat      60
ccggcggcgg cgcatcacca tcaccatcac gagaacctgt acttccaggg catggagagc     120
tgttaccttg tccacaccct gctggagttc tacttgaaaa ctgttttcag aaactaccac     180
aatagaacag ttgaagtcag gactctgaag tcattctcta ctctggccaa caactttgtt     240
ctcatcgtgt cacaactgca acccagtcaa gaaaatgaga tgttttccat cagagacagt     300
gcacacaggc ggttcctgct attccggaga gcattcaaac agttggacgt agaagcagct     360
ctgaccaaag cccttgggga agtggacatt cttctgacct ggatgcagaa attctacaag     420
ctctag                                                                 426

<210> SEQ ID NO 18
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 18

Glu Ser Cys Tyr Leu Val His Thr Leu Leu Glu Phe Tyr Leu Lys Thr
1               5                   10                  15

Val Phe Arg Asn Tyr His Asn Arg Thr Val Glu Val Arg Thr Leu Lys
            20                  25                  30

Ser Phe Ser Thr Leu Ala Asn Asn Phe Val Leu Ile Val Ser Gln Leu
        35                  40                  45

Gln Pro Ser Gln Glu Asn Glu Met Phe Ser Ile Arg Asp Ser Ala His
    50                  55                  60

Arg Arg Phe Leu Leu Phe Arg Arg Ala Phe Lys Gln Leu Asp Val Glu
65                  70                  75                  80

Ala Ala Leu Thr Lys Ala Leu Gly Glu Val Asp Ile Leu Leu Thr Trp
                85                  90                  95

Met Gln Lys Phe Tyr Lys Leu
            100

<210> SEQ ID NO 19
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 19
caactgttct attgtggtag tttctgaaaa cagttttcaa gtagaac                    47

<210> SEQ ID NO 20
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 20
gttctacttg aaaactgttt tcagaaacta ccacaataga acagttg                    47
```

MDA-7/IL-24 SECRETORY VARIANTS AND METHODS OF USE

CROSS-REFERENCES TO RELATED APPLICATIONS

This application claims the benefit of U.S. Provisional Application No. 62/620,649, filed Jan. 23, 2018, and U.S. Provisional Application No. 62/620,673, filed Jan. 23, 2018, which are hereby incorporated by reference in their entireties and for all purposes.

SEQUENCE LISTING

The Sequence Listing written in file 053151-506001WO_Sequence_Listing_ST25.txt, created on Jan. 18, 2019, 17,015 bytes, machine format IBM-PC, MS-Windows operating system, is hereby incorporated by reference.

BACKGROUND

Cancer is a leading cause of death and is responsible for increasing health costs. Traditionally, cancer has been treated using chemotherapy, radiotherapy and surgical methods. Tumor cell plasticity and heterogeneity, however, remain challenges for effective treatments of many cancers. In addition, traditional therapies may have drawbacks, e.g. insufficient specificity, intolerable toxicity and too low efficacy.

Melanoma differentiation associated gene-7/Interleukin-24 (MDA-7/IL24), a secreted protein of the IL-10 family, functions as a cytokine at normal physiological levels and is expressed in tissues of the immune system. At supra-physiological levels, MDA-7/IL-24 plays a prominent role in inhibiting tumor growth, invasion, metastasis and angiogenesis and was recently shown to target tumor stem/initiating cells for death. MDA-7/IL-24 can selectively induce cell death in cancer cells without affecting normal cells.

BRIEF SUMMARY

In view of the foregoing, there is a need for improved cancer therapies, and optimized versions of MDA-7/IL-24 in particular. The present disclosure provides methods and compositions that address this need, and provide additional benefits as well.

In some aspects, the present disclosure provides polynucleotides encoding a fusion protein, wherein the fusion protein includes an insulin signal peptide and an MDA-7/IL-24 protein. In embodiments, the MDA-7/IL-24 protein includes an amino acid sequence that is at least 90% identical to SEQ ID NO: 4. In embodiments, the MDA-7/IL-24 protein includes an amino acid sequence that is at least 90% identical to SEQ ID NO: 3. In embodiments, the MDA-7/IL-24 protein includes a mutation corresponding to (a) a change of K122R relative to SEQ ID NO: 2, (b) a change of K73R relative to SEQ ID NO: 3, or (c) a change of K19R relative to SEQ ID NO: 4. In embodiments, the insulin signal peptide is a human insulin signal peptide. In embodiments, the insulin signal peptide includes an amino acid sequence that is at least 90% identical to SEQ ID NO: 5. In embodiments, the polynucleotide includes a nucleotide sequence that is at least 90% identical to any one of SEQ ID NOs: 6, 10-12, or 17. In embodiments, the MDA-7/IL-24 protein is capable of activating an IL-20/IL-22 receptor complex of a cancer cell. In embodiments, the MDA-7/IL-24 protein includes an amino acid sequence of SEQ ID NO: 18. In embodiments, the polynucleotide does not encode amino acids 1-49 of SEQ ID NO: 2. In embodiments, the polynucleotide does not encode amino acids 1-54 of SEQ ID NO: 3.

In some aspects, the present disclosure provides vectors including a polynucleotide described herein. In embodiments, the vector is a plasmid. In embodiments, the vector is a virus, such as an adenovirus. In embodiments, the adenovirus is replication incompetent. In embodiments, the adenovirus is under control of a cancer-specific promoter, such as a Progression Elevated Gene (PEG)-3 promoter.

In some aspects, the present disclosure provides a cell including a polynucleotide or vector disclosed herein. In embodiments, the cell is an immune cell, such as a T cell.

In some aspects, the present disclosure provides a composition including (a) a polynucleotide or vector disclosed herein, and (b) a pharmaceutically acceptable excipient. In embodiments, the composition further includes an Mcl-1 inhibitor, such as BI-97D6, BI-97C1, UMI-77, Marinopyrrole A, or A-1210477. In embodiments, the composition further includes a PI3K inhibitor, such as LY294002.

In some aspects, the present disclosure provides methods of treating cancer. In embodiments, the methods include administering to a subject in need thereof a polynucleotide, a vector, or a composition described herein. In embodiments, the method includes administering an Mcl-1 inhibitor, such as BI-97D6, BI-97C1, UMI-77, Marinopyrrole A, or A-1210477. In embodiments, the method includes administering a PI3K inhibitor, such as LY294002. In embodiments, the cancer is prostate cancer, breast cancer, or lung cancer. In embodiments, the cancer is prostate cancer. In embodiments, the prostate cancer includes cancer cells having an increased expression of one or more of Mcl-1, RANKL, Bcl-2, Bcl-xL, and Akt, relative to normal prostate cells.

In some aspects, the present disclosure provides uses of a composition in the manufacture of a medicament for the treatment of cancer in a subject in need thereof. In embodiments, the composition includes a polynucleotide, vector, cell, or composition described herein.

In some aspects, the present disclosure provides proteins. In embodiments, the protein is a protein encoded by a polynucleotide or vector disclosed herein, or a secretion product thereof. In embodiments, the protein is a fusion protein including an insulin signal peptide and an MDA-7/IL-24 protein.

BRIEF DESCRIPTION OF THE DRAWINGS

FIG. 27A: A murine CaP cell line, a mu-PDX, derived from a Hi-Myc mouse was subcutaneously implanted in 4-month-old (n=3 for control and treated group) Hi-Myc mice. Once subcutaneous tumors appeared (~7 days) the tumor was injected with either Ad. null or Ad.CTV (108 VP/injections) 3× a week for 4 weeks. Mice were kept an additional 2 weeks without any treatment and then euthanized. Both the prostate and the primary subcutaneous tumors were compared (representative photomicrographs are presented). FIG. 27B: 4-month old Hi-Myc mice received either Ad. null or Ad.CTV delivered in microbubbles for a total of 6 IV injections combined with ultrasound over a two-week period (UTMD approach). Hi-Myc mu-PDX cells were subcutaneously implanted and treatment continued for one additional week through tail vein injection, combined with ultrasound virus release. Mice were kept one week without any additional treatment and euthanized. Prostate tumors and subcutaneously implanted tumors were compared. Representative photographs are presented.

FIG. 28A: Tumor-sensitized T cells, derived from RM1 CaP bearing mice, were expanded by IL-7/IL-15 and infected with lentiviruses encoding MDA-7/IL-24 or empty vector. The level of MDA-7/IL24 in the media was examined using immunoblotting. C57BL/6 mice with established RMI-Luc lung metastases were treated with or without MDA-7/IL-24-producing T cells. Pulmonary metastases were followed using a small animal imaging system (FIG. 28B) and quantified by clonogenic assays using lung tissues (FIG. 28C).

FIG. 31A: CD8+ T cells were stimulated with anti-CD3/CD28 antibodies in the presence or absence of purified MDA-7/IL-24 protein (20 ng/ml). Cell proliferation was measured using $^3$H-thymidine (TdR) incorporation assays. p<0.05. FIG. 31B: C57BL/6 mice were injected i.v. with MDA-7/IL-24 protein (10 μg) or PBS. 48 h later, lymph node cells were assessed for IFN-γ-producing CD8+ T cells by intracellular staining.

FIG. 32A. Establishment of bone metastases by intratibial injection of the RMI-Luc cells, followed by bioluminescence imaging analysis. FIG. 32B: CD8+ cells in the bone marrow cavity from naïve mice or mice with established CaP bone metastases were examined for PD-1 expression by FACS.

FIGS. 34A and 34C: measurement of tumor volume. The data represent mean±SD with a minimum of five mice per group. FIGS. 34B and 34D: measurement of tumor weight at the end of the study. The data represent mean±SD with at least five mice per group.

FIG. 35A: representative images of mice treated with or without Ad.5.CTV-m7 virus. 50% of palpable tumors that formed were injected with Ad.5.-CTV-m7. A maximum of 10 injections were administered per injected tumor (depending on when the tumors arose) over 4 weeks. FIG. 35B: representative images of the resected tumors. The average tumor volumes are represented graphically. FIG. 35C: immunohistochemical staining of tumors to detect MDA-7/IL-24 expression. While tumors that formed in the control mice do not show MDA-7/IL-24 expression, both injected and uninjected tumors on Ad5.CTV-m7 treated mice showed expression of MDA-7/IL-24.

FIG. 36C: MDA-MB-231 cells (2×10$^6$) were infected with the indicated viruses (2000 or 5000 VP) and after 48 hours, cell lysates were analyzed for fusion protein by Western blotting.

FIG. 37A: to confirm the association of His-MDA-7 with MBs, Alexa Fluor 488 labeled His-MDA-7 was mixed and incubated with lyophilized MBs. The unincorporated labeled His-MDA-7 was removed by centrifugation and the MB (white layer) was mixed with 1 ml PBS and observed under a fluorescent microscope. The labeled his-MDA-7 (green fluorescence) was associated with the lipid shell of the MB. FIG. 37B: DU-145, human prostate cancer cells were established as xenografts in the left flank of nude mice. Alexa Fluor labeled His-MDA-7/MB complexes were injected through the tail vein and sonoporated in the tumor implanted in the left flank with an ultrasound portable SonoSite Micro-Maxx US platform (SonoSite) for 10 min. The fluorescent image was captured using Xenogen IVIS spectrum. FIG. 37C: biotinylated anti-V-CAM-1 (B-VCAM-1) (100 μg) was incubated with Streptavidin microbubble (MB-SA) (~10$^9$ MB particles) that formed the complex Biotin-anti-V-CAM-1-Streptavidin-MB (MB-SA-B-anti-VCAM-1; D-MB). In order to validate the preparation of D-MB, both the D-MB as well as simple MB-SA was mixed with Avidin-FITC, and flow-cytometry confirmed the formation of D-MB. FIG. 37D: D-MB complexed with Ad.luc was systemically injected via tail vein and sonoporated in the tumor region of MMTV-PyMT. Bioluminescence imaging (BLI) was done after 72-h of post injection of D-MB/Ad.luc using IVIS spectrum.

FIG. 38A: T cells from 4T1-mammary tumor-bearing mice were reprogrammed and expanded by IL-7/IL-15, and engineered with a lentivirus encoding MDA-7/IL-24. Media of modified T cells were analyzed for MDA-7/IL-24 levels by immunoblotting. FIG. 38B: mice were injected i.v. with 2.5×10$^5$ 4T1-Luc cells, followed by treatment with T cells engineered to produce MDA-7/IL-24 (T-MDA-7) or T cells correspondingly modified with a control virus (T-vec). Tumors in the lungs were imaged two weeks later.

FIG. 41A: immunogenic BCa cell death induced by MDA-7/IL-24 therapy. BALB/c mice were immunized with irradiated, Ad.mda-7 (1,2) or Ad.null (3,4) infected 4T1 cells (MOI=1), challenged with live 4T1 cells. The images were taken two weeks' post-tumor challenge. FIG. 41B: ER stress response induced by MDA-7/IL-24, indicated by upregulation of ER-resident chaperones. FIG. 41C: MDA-7/IL-24 therapy triggers the surface presence of CRT, assessed by immunofluorescence staining (left) and immunoblotting analysis of plasma membrane or cytosolic fractions (right).

DETAILED DESCRIPTION

Figure 1:
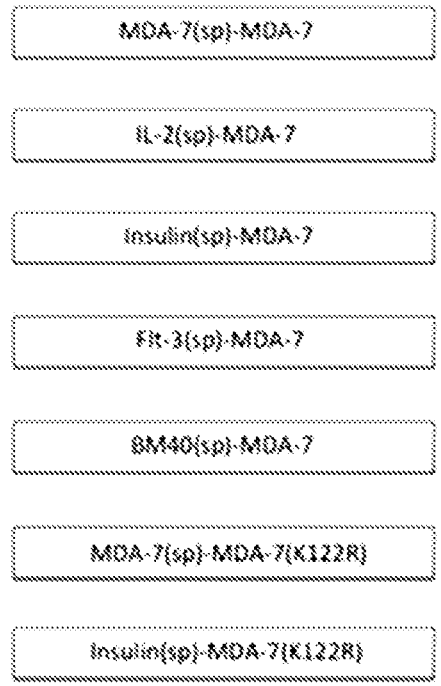
FIG. 1 shows a schematic illustration of example MDA-7/IL-24 modifications (not drawn to scale).

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

Section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entireties for any purpose.

Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention. The following definitions are provided to facilitate understanding of certain terms used frequently herein and are not meant to limit the scope of the present disclosure.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

It is noted that, as used herein and in the appended claims, the singular forms "a," "an," and "the" include plural referents unless the context clearly dictates otherwise. It is further noted that the claims may be drafted to exclude any optional element. As such, this statement is intended to serve as support for the recitation in the claims of such exclusive terminology as "solely," "only," and the like in connection with the recitation of claim elements, or use of a "negative" limitations, such as "wherein [a particular feature or element] is absent," or "except for [a particular feature or element]," or "wherein [a particular feature or element] is not present (included, etc.) . . . ."

The terms "nucleic acid," "nucleic acid molecule," "nucleic acid oligomer," "oligonucleotide," "nucleic acid sequence," "nucleic acid fragment," and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide," and "protein" are used interchangeably herein to refer to a polymer of amino acid residues, of any length. The polymer may be linear or branched, it may comprise modified amino acids, and it may be interrupted by non amino acids. The terms also encompass an amino acid polymer that has been modified; for example, by disulfide bond formation, glycosylation, lipidation, acetylation, phosphorylation, or any other manipulation, such as conjugation with a labeling component. A "fusion protein" refers to a chimeric protein including two or more separate protein sequences that are recombinantly expressed as a single moiety.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a sequence comparison algorithm (optionally, with default parameters) or by manual alignment and visual inspection. In embodiments, sequences that are "substantially identical" are at least 80%, 90%, 95%, 99%, or more identical. In the case of nucleic acids, percent identity may also refer to, or may be applied to, the complement of a test sequence. As described below, the preferred algorithms can account for gaps and the like. In embodiments, identity exists over a region that is at least about 25 amino acids or nucleotides in length, or more preferably over a region that is 50-100 amino acids or nucleotides in length.

"Percentage of sequence identity" is determined by comparing two optimally aligned sequences over a comparison window, wherein the portion of the polynucleotide or polypeptide sequence in the comparison window may comprise additions or deletions as compared to the reference sequence (which does not comprise the additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison (e.g., with respect to the reference sequence), and multiplying the result by 100 to yield the percentage of sequence identity. Programs for determining sequence identity are known to those skilled in the art, and include, without limitation, BLAST (see, e.g., NCBI web site www.ncbi.nlm.nih.gov/BLAST or the like, optionally using default parameters), the Needleman-Wunsch algorithm (see e.g. the EMBOSS Needle aligner available at www.ebi.ac.uk/Tools/psa/emboss-_needle/, optionally with default settings).

An amino acid or nucleotide base "position" is denoted by a number that sequentially identifies each amino acid (or nucleotide base) in the reference sequence based on its position relative to the N-terminus (or 5-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence. Amino acid mutations may be identified by a designation identifying the original amino acid (e.g., as in a wild-type or reference sequence), the position of the mutation, and the amino acid to which the original amino acid was changed. For example, "K122R relative to SEQ ID NO: 2" indicates a mutation of the lysine at position 122 of SEQ ID NO: 2 to an arginine. Nucleotide mutations can use a similar designation scheme.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. Whether an amino acid corresponds to a particular position in a reference sequence (e.g., a mutation of K122R relative to SEQ ID NO: 2), optionally at a different position, can be determined by sequence alignment. In general, an alignment showing identity of one or more amino acids flanking the indicated position of the reference sequence will allow the corresponding position of the query sequence to be positioned locally with respect to the reference sequence to confirm the presence of a mutation of the corresponding amino acid, optionally at a shifted numerical position in the query sequence. In embodiments, a region comprising at least three to fifteen amino acids, including the mutation position, will locally align with the corresponding reference sequence with a relatively high percent identity, except for the position of the mutant amino acid along the query sequence (e.g. at least about 90%, 95%, or 100% identity). In embodiments, an amino acid of a query MDA-7/IL-24 protein sequence corresponds to a particular position of a reference sequence if the polypeptide of the query sequence aligns to the particular position of the reference sequence when the two sequences are optimally aligned using a BLASTP alignment algorithm with default parameters.

The terms "MDA-7," "IL-24," or "MDA-7/IL-24" refer to a protein (including homologs, isoforms, and functional fragments thereof) with MDA-7 activity. The term includes any recombinant or naturally-occurring form of MDA-7 or variants, homologs, or isoforms thereof that maintain MDA-7 activity (e.g. within at least 30%, 40%, 50%, 60%, 70%, 80%, 90%, 95%, or 100% activity compared to wild-type MDA-7). In embodiments, the variants, homologs, or isoforms have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring MDA-7 protein. In embodiments, the MDA-7 protein is substantially identical to the protein identified by Accession No. NP_006841 or a variant or homolog having substantial identity thereto. In embodiments, the MDA-7 protein is substantially identical to the protein identified by UniProt Q13007 or a variant or homolog having substantial identity thereto. In embodiments, the IL-24 gene is substantially identical to the nucleic acid sequence set forth in RefSeq (mRNA) NM_006850, or a variant or homolog having substantial identity thereto. In embodiments, the IL-24 gene is substantially identical to the nucleic acid sequence set forth in Ensembl reference number ENSG00000162892, or a variant or homolog having substantial identity thereto. In embodiments, the amino acid sequence or nucleic acid sequence is the sequence known at the time of filing of the present application. In embodiments, the protein is a precursor form that includes a signal sequence. In embodiments, the signal sequence is not the native MDA-7 signal sequence, such as a modified native signal sequence, an unmodified signal sequence from another gene (e.g., the insulin gene), or a modified signal sequence from another gene. In embodiments, the protein is a mature form of MDA-7, in which a signal sequence at the N-terminus of a precursor form of the protein is absent. The mature form can be produced post-translationally from a precursor form containing a signal sequence, or can be translated directly from a polynucleotide encoding the mature form without a signal sequence N-terminal with respect to the sequence of the mature MDA-7. In embodiments, the MDA-7/IL-24 protein comprises SEQ ID NO: 4, or variants, homologs, or isoforms thereof that maintain or enhance MDA-7 activity. In embodiments, the MDA-7/IL-24 protein comprises SEQ ID NO: 3, or variants, homologs, or isoforms thereof that maintain or enhance MDA-7 activity. In embodiments, the MDA-7/IL-24 protein does not comprise the first 49 amino acids of SEQ ID NO: 2. In embodiments, the MDA-7/IL-24 protein comprises SEQ ID NO: 18, or variants, homologs, or isoforms thereof that maintain or enhance MDA-7 activity.

The terms "signal sequence" and "signal peptide" refer to a polypeptide sequence that is capable of directing the secretion of a protein that includes the signal peptide. Typically, a signal peptide is at or near the N-terminus of a protein. The signal peptide may be immediately adjacent to the protein to be secreted, or may be joined by a linker of one or more amino acids. In eukaryotes, secretion typically involves directing a protein to the endoplasmic reticulum, and may involve cleavage to remove some or all of the signal peptide prior to secretion out of the cell. In bacteria, proteins may be secreted to the periplasm or into the medium. A signal peptide is capable of directing the secretion of a protein that includes the signal peptide if, when the signal peptide is attached to a protein of interest (e.g., an MDA-7/IL-24 protein), more of the protein of interest is secreted from a cell than in the absence of the signal peptide. In embodiments, at least about 10%, 20%, 30%, 40%, 50%, 60%, 70%, 80%, 90%, 95% or more of the protein of interest is secreted. In embodiments, at least 50% of the protein of interest is secreted. Secretion can be measured in any suitable system, such as in cultured cells described herein. In embodiments, the signal sequence is joined to a protein of interest such that cleavage during the secretion process removes the entire signal sequence.

One of skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Certain amino acids may be substituted for other amino acids in a protein structure without appreciable loss of tumoricidal effects. Since it is the interactive capacity and nature of a protein that defines that protein's biological functional activity, certain amino acid substitutions can be made in a protein sequence, and, of course, in its DNA encoding sequence, and nevertheless obtain a protein with like properties. It is thus contemplated that various changes may be made in the polypeptide sequences of the present disclosure, or corresponding DNA sequences which encode said polypeptides, while retaining at least some of their biological activity. Such biological activity can be assessed by various techniques, such as for instance assays described in the examples herein.

The term "purified," when applied to a nucleic acid or protein, denotes that the nucleic acid or protein is essentially free of one or more other cellular components with which it is associated in the natural state or in a whole cell lysate. It can be, for example, in a homogeneous state or in a mixture with one or more other compounds, and may be in either a dry or aqueous solution. For example, an MDA-7/IL-24 protein (or a polynucleotide or vector encoding the same) may be purified from a cell lysate, then combined with one or more other agents (e.g., an Mcl-1 inhibitor and/or a PI3K inhibitor). As such, compositions comprising a purified MDA-7/IL-24 protein (or a polynucleotide or vector encoding the same) may comprise additional compounds, but will generally lack or be reduced in one or more impurities present in a lysate or media from which an MDA-7/IL-24 protein (or a polynucleotide or vector encoding the same) is initially isolated. Purity and homogeneity are typically determined using analytical chemistry techniques such as polyacrylamide gel electrophoresis or high performance liquid chromatography. A molecule that is the predominant species present in a preparation is substantially purified.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head and neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is a cancer that metastasized to bone. In embodiments, the cancer is prostate cancer, such as prostate cancer-derived bone metastasis.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., prostate, which site is referred to as a primary tumor, e.g., primary prostate cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if prostate cancer metastasizes to the bone, the secondary tumor at the site of the bone consists of abnormal prostate cells and not abnormal bone cells. The secondary tumor in the bone is referred to as a metastatic bone cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the bone.

As used herein, a "subject" can be a mammal such as a non-primate (e.g., cows, pigs, horses, cats, dogs, rats, etc.) or a primate (e.g., monkey and human). In embodiments, the subject is a human. In embodiments, the subject is a mammal (e.g., a human) having or potentially having a cancer, such as a metastatic cancer, described herein. In embodiments, the subject is a mammal (e.g., a human) at risk of developing a cancer, such as a metastatic cancer, described herein.

"Treating" or "treatment" as used herein broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, delay or slowing of disease progression, amelioration or palliation of the disease state, diminishment of the reoccurrence of disease, and remission, whether partial or total and whether detectable or undetectable. In other words, "treatment" as used herein includes any cure or amelioration of a disease. Treatment may relieve the disease's symptoms fully or partially remove the disease's underlying cause, shorten a disease's duration, or do a combination of these things. In the case of cancer, treatment may include slowing, halting, or reversing cancer cell multiplication (e.g., as in growth of a tumor, as measured by tumor size or a rate of change thereof).

"Preventing" as used herein refers to a decrease in the occurrence or incidence of one or more disease symptoms in a patient. Prevention may be complete (no detectable symptoms) or partial, such that fewer symptoms are observed than would likely occur absent treatment. Prevention includes prophylactic treatment.

The length of treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prevention may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, administering a composition of the present disclosure both treats a cancer of a subject (e.g., metastatic bone cancer), and prevents further disease systems (e.g., metastasis, such as bone metastases).

The compositions described herein can be used in combination with one another, or with other active agents known to be useful in treating a cancer, such as anti-cancer agents.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cancer cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

As used herein, the term "administering" encompasses oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). In embodiments, "administering" a protein or a composition comprising the protein refers to administering the protein itself (e.g., an MDA-7/IL-24 protein), rather than a polynucleotide encoding the protein.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

A "combined synergistic amount" as used herein refers to the sum of a first amount (e.g., an amount of MDA-7/IL-24 recombinant protein, or polynucleotide or vector encoding the same) and a second amount (e.g., an amount of an inhibitor, such as an Mcl-1 inhibitor), that results in a synergistic effect (i.e. an effect greater than an additive effect). Therefore, the terms "synergy," "synergism," "synergistic," "combined synergistic amount," and "synergistic therapeutic effect" which are used herein interchangeably, refer to a measured effect of compounds administered in combination where the measured effect is greater than the sum of the individual effects of each of the compounds administered alone as a single agent.

In embodiments, a combined synergistic amount is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the first amount (e.g., MDA-7/IL-24 protein, or polynucleotide or vector encoding the same) when used separately from the second amount (e.g., an inhibitor, such as an Mcl-1 inhibitor). In embodiments, a combined synergistic amount is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the second amount (e.g., an inhibitor, such as an Mcl-1 inhibitor) when used separately from the first amount (e.g., MDA-7/IL-24 protein, or polynucleotide or vector encoding the same).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor that binds to a target protein). In embodiments, inhibition refers to a reduction of activity of a target protein from an indirect interaction (e.g., an inhibitor that binds to a protein that activates a target protein, thereby preventing target protein activation). "Mcl-1 inhibitors" include compounds that negatively affect (e.g. decreases) the activity or function of Mcl-1 or other signaling pathway components (e.g., proteins, genes) involved in the Mcl-1 signaling pathway relative to the activity or function of Mcl-1 or signaling pathway components (e.g., proteins, genes) involved in the Mcl-1 signaling pathway in the absence of the inhibitor. In embodiments, an Mcl-1 inhibitor is an agent that directly binds to and inhibits the activity of Mcl-1.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a Mcl-1 with a compound as described herein (e.g., Mcl-1 inhibitor) may reduce the level of a product of the Mcl-1 catalyzed reaction or the level of a downstream derivative of the product, or binding may reduce the interactions between Mcl-1 or an Mcl-1 reaction product and downstream effectors or signaling pathway components, resulting in changes in cell growth, proliferation, or survival.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Compositions

In some aspects, the present disclosure provides a polynucleotide encoding a fusion protein. In embodiments, the fusion protein includes an insulin signal peptide and an MDA-7/IL-24 protein.

In embodiments, the MDA-7/IL-24 protein includes an amino acid sequence of SEQ ID NO: 4, or a variant thereof. In embodiments, the MDA-7/IL-24 protein includes an amino acid sequence that is about or at least about 80%, 85%, 90%, 95%, 96%, 97%, 98%, 99%, or 100% identical to SEQ ID NO: 4. In embodiments, the MDA-7/IL-24 protein includes an amino acid sequence that is about or at least about 90% identical to SEQ ID NO: 4. In embodiments, the MDA-7/IL-24 protein includes an amino acid sequence that is about or at least about 95% identical to SEQ ID NO: 4.

In embodiments, the MDA-7/IL-24 protein includes an amino acid sequence that is about or at least about 80% identical to SEQ ID NO: 4. In embodiments, the MDA-7/IL-24 protein includes an amino acid sequence that is about or at least about 85% identical to SEQ ID NO: 4. In embodiments, the MDA-7/IL-24 protein includes an amino acid sequence that is about or at least about 90% identical to SEQ ID NO: 4. In embodiments, the MDA-7/IL-24 protein includes an amino acid sequence that is about or at least about 95% identical to SEQ ID NO: 4. In embodiments, the MDA-7/IL-24 protein includes an amino acid sequence that is about or at least about 96% identical to SEQ ID NO: 4. In embodiments, the MDA-7/IL-24 protein includes an amino acid sequence that is about or at least about 97% identical to SEQ ID NO: 4. In embodiments, the MDA-7/IL-24 protein includes an amino acid sequence that is about or at least about 98% identical to SEQ ID NO: 4. In embodiments, the MDA-7/IL-24 protein includes an amino acid sequence that is about or at least about 99% identical to SEQ ID NO: 4. In embodiments, the MDA-7/IL-24 protein includes an amino acid sequence that is about 100% identical to SEQ ID NO: 4. In embodiments, the MDA-7/IL-24 protein includes an amino acid sequence that is about or at least about 80%, 85%, 90%, 95%, 96%, 97%, 98%, 99%, or 100% identical across 25, 50, 75, or 100 continuous amino acids of SEQ ID NO: 4.

In embodiments, the MDA-7/IL-24 protein includes an amino acid sequence of SEQ ID NO: 18, or a variant thereof. In embodiments, the MDA-7/IL-24 protein includes an amino acid sequence that is about or at least about 80%, 85%, 90%, 95%, 96%, 97%, 98%, 99%, or 100% identical to SEQ ID NO: 18. In embodiments, the MDA-7/IL-24 protein includes an amino acid sequence that is about or at least about 90% identical to SEQ ID NO: 18. In embodiments, the MDA-7/IL-24 protein includes an amino acid sequence that is about or at least about 95% identical to SEQ ID NO: 18.

In embodiments, the MDA-7/IL-24 protein includes an amino acid sequence that is about or at least about 80% identical to SEQ ID NO: 18. In embodiments, the MDA-7/IL-24 protein includes an amino acid sequence that is about or at least about 85% identical to SEQ ID NO: 18. In embodiments, the MDA-7/IL-24 protein includes an amino acid sequence that is about or at least about 90% identical to SEQ ID NO: 18. In embodiments, the MDA-7/IL-24 protein includes an amino acid sequence that is about or at least about 95% identical to SEQ ID NO: 18. In embodiments, the MDA-7/IL-24 protein includes an amino acid sequence that is about or at least about 96% identical to SEQ ID NO: 18. In embodiments, the MDA-7/IL-24 protein includes an amino acid sequence that is about or at least about 97% identical to SEQ ID NO: 18. In embodiments, the MDA-7/IL-24 protein includes an amino acid sequence that is about or at least about 98% identical to SEQ ID NO: 18. In embodiments, the MDA-7/IL-24 protein includes an amino acid sequence that is about or at least about 99% identical to SEQ ID NO: 18. In embodiments, the MDA-7/IL-24 protein includes an amino acid sequence that is about 100% identical to SEQ ID NO: 18. In embodiments, the MDA-7/IL-24 protein includes an amino acid sequence that is about or at least about 80%, 85%, 90%, 95%, 96%, 97%, 98%, 99%, or 100% identical across 25, 50, 75, or 100 continuous amino acids of SEQ ID NO: 18.

In embodiments, the MDA-7/IL-24 protein includes an amino acid sequence of SEQ ID NO: 3, or a variant thereof. In embodiments, the MDA-7/IL-24 protein includes an amino acid sequence that is about or at least about 80%, 85%, 90%, 95%, 96%, 97%, 98%, 99%, or 100% identical to SEQ ID NO: 3. In embodiments, the MDA-7/IL-24 protein includes an amino acid sequence that is about or at least about 90% identical to SEQ ID NO: 3. In embodiments, the MDA-7/IL-24 protein includes an amino acid sequence that is about or at least about 95% identical to SEQ ID NO: 3.

In embodiments, the MDA-7/IL-24 protein includes an amino acid sequence that is about or at least about 80% identical to SEQ ID NO: 3. In embodiments, the MDA-7/IL-24 protein includes an amino acid sequence that is about or at least about 85% identical to SEQ ID NO: 3. In embodiments, the MDA-7/IL-24 protein includes an amino acid sequence that is about or at least about 90% identical to SEQ ID NO: 3. In embodiments, the MDA-7/IL-24 protein includes an amino acid sequence that is about or at least about 95% identical to SEQ ID NO: 3. In embodiments, the MDA-7/IL-24 protein includes an amino acid sequence that is about or at least about 96% identical to SEQ ID NO: 3. In embodiments, the MDA-7/IL-24 protein includes an amino acid sequence that is about or at least about 97% identical to SEQ ID NO: 3. In embodiments, the MDA-7/IL-24 protein includes an amino acid sequence that is about or at least about 98% identical to SEQ ID NO: 3. In embodiments, the MDA-7/IL-24 protein includes an amino acid sequence that is about or at least about 99% identical to SEQ ID NO: 3. In embodiments, the MDA-7/IL-24 protein includes an amino acid sequence that is about 100% identical to SEQ ID NO: 3. In embodiments, the MDA-7/IL-24 protein includes an amino acid sequence that is about or at least about 80%, 85%, 90%, 95%, 96%, 97%, 98%, 99%, or 100% identical across 50, 75, 100, or 150 continuous amino acids of SEQ ID NO: 3.

In embodiments, the MDA-7/IL-24 protein includes a lysine to arginine mutation corresponding to a change of K122R relative to SEQ ID NO: 2, a change of K73R relative to SEQ ID NO: 3, or a change of K19R relative to SEQ ID NO: 4. SEQ ID NO: 18 is an example of an amino acid sequence having a mutation of K122R relative to SEQ ID NO: 2. However, because SEQ ID NO: 18 represents a shorter sequence than SEQ ID NO: 2, the position of the mutation with respect to SEQ ID NO: 18 is amino acid 19. Nonetheless, optimal alignment between the two sequences shows that SEQ ID NO: 18 aligns to a portion within SEQ ID NO: 2 that is 100% identical except at position 19 of SEQ ID NO: 18, corresponding to position 122 of SEQ ID NO: 2. In addition, SEQ ID NO: 18 represents the result of a K19R mutation to SEQ ID NO: 4, as the two sequences are completely identical except at the mutant position.

In embodiments, the insulin signal peptide is a human insulin signal peptide. In embodiments, the insulin signal peptide includes an amino acid sequence of SEQ ID NO: 5, or a variant thereof. In embodiments, the insulin signal peptide includes an amino acid sequence that is at least about 80%, 85%, 90%, 95%, 96%, 97%, 98%, 99%, or 100% identical to SEQ ID NO: 5. In embodiments, the insulin signal peptide includes an amino acid sequence that is about or at least about 90% identical to SEQ ID NO: 5. In embodiments, the insulin signal peptide includes an amino acid sequence that is about or at least about 95% identical to SEQ ID NO: 5. In embodiments, the insulin signal peptide has 1, 2, 3, 4, or 5 amino acid substitutions with respect to SEQ ID NO: 5. In embodiments, the insulin signal peptide is joined to the MDA-7/IL-24 protein by a linker of about or more than about 1, 2, 3, 4, 5, 6, 7, 8, 9, 10, or more amino acids. In embodiments, the linker is about 1-10, 2-8, 3-7, or 4-6 amino acids in length. In embodiments, the insulin signal peptide is at the N-terminus of the fusion protein. In embodiments, the insulin signal peptide is within about 1, 2, 3, 4, 5, or more amino acids of the N-terminus of the fusion protein.

In embodiments, the insulin signal peptide includes an amino acid sequence that is about or at least about 80% identical to SEQ ID NO: 5. In embodiments, the insulin signal peptide includes an amino acid sequence that is about or at least about 85% identical to SEQ ID NO: 5. In embodiments, the insulin signal peptide includes an amino acid sequence that is about or at least about 90% identical to SEQ ID NO: 5. In embodiments, the insulin signal peptide includes an amino acid sequence that is about or at least about 95% identical to SEQ ID NO: 5. In embodiments, the insulin signal peptide includes an amino acid sequence that is about or at least about 96% identical to SEQ ID NO: 5. In embodiments, the insulin signal peptide includes an amino acid sequence that is about or at least about 97% identical to SEQ ID NO: 5. In embodiments, the insulin signal peptide includes an amino acid sequence that is about or at least about 98% identical to SEQ ID NO: 5. In embodiments, the insulin signal peptide includes an amino acid sequence that is about or at least about 99% identical to SEQ ID NO: 5. In embodiments, the insulin signal peptide includes an amino acid sequence that is about 100% identical to SEQ ID NO: 5. In embodiments, the insulin signal peptide includes an amino acid sequence that is about or at least about 80%, 85%, 90%, 95%, 96%, 97%, 98%, 99%, or 100% identical across 5, 10, 15, 20, or 24 continuous amino acids of SEQ ID NO: 5.

In embodiments, the inclusion of the insulin signal peptide in the fusion protein functions to increase the mRNA transcript level, protein level, mature protein level, mature protein fraction, secretion, and/or anti-cancer activity of the MDA-7/IL-24 protein. In embodiments, functions of the signal peptide are measured relative to a protein consisting of the amino acid sequence of SEQ ID NO: 2 (or a polynucleotide or vector encoding the same). In embodiments, functions of the signal peptide are measured relative to the corresponding MDA-7/IL-24 protein lacking the insulin signal peptide (or a polynucleotide or vector encoding the same). In embodiments, the mRNA transcript level, protein level, mature protein level, mature protein fraction, secretion, and/or anti-cancer activity of the MDA-7/IL-24 protein is increased by about or at least about 5%, 10%, 15%, 20%, 30%, 40%, 50%, 75%, 100%, 150%, 200% or more. In embodiments, the increase is about 5-200%, 10-150%, 20-100%, or 40-75%. In embodiments, the increase is at least about 5%. Relative changes effected by the insulin signal peptide can be measured in any suitable system, such as in cultured cells described herein.

In embodiments, the polynucleotide encoding the fusion protein includes a sequence described herein. In embodiments, the polynucleotide includes a nucleotide sequence of any one of SEQ ID NOs: 6, 10-12, or 17, or a variant thereof. In embodiments, the polynucleotide includes a nucleotide sequence that is at least about 80%, 85%, 90%, 95%, 96%, 97%, 98%, 99%, or 100% identical to any one of SEQ ID NOs: 6, 10-12, or 17. In embodiments, the polynucleotide includes a nucleotide sequence that is about or at least about 90% identical to any one of SEQ ID NOs: 6, 10-12, or 17. In embodiments, the polynucleotide includes a nucleotide sequence that is about or at least about 95% identical to any one of SEQ ID NOs: 6, 10-12, or 17. In embodiments, the polynucleotide includes a nucleotide sequence that is about or at least about 80% identical (e.g. 90%, 95%, or 100% identical) to SEQ ID NO: 17.

In embodiments, the polynucleotide encoding the fusion protein includes a nucleotide sequence that is about or at least about 80% identical to SEQ ID NO: 6. In embodiments, the polynucleotide includes a nucleotide sequence that is about or at least about 85% identical to SEQ ID NO: 6. In embodiments, the polynucleotide includes a nucleotide sequence that is about or at least about 90% identical to SEQ ID NO: 6. In embodiments, the polynucleotide includes a nucleotide sequence that is about or at least about 95% identical to SEQ ID NO: 6. In embodiments, the polynucleotide includes a nucleotide sequence that is about or at least about 96% identical to SEQ ID NO: 6. In embodiments, the polynucleotide includes a nucleotide sequence that is about or at least about 97% identical to SEQ ID NO: 6. In embodiments, the polynucleotide includes a nucleotide sequence that is about or at least about 98% identical to SEQ ID NO: 6. In embodiments, the polynucleotide includes a nucleotide sequence that is about or at least about 99% identical to SEQ ID NO: 6. In embodiments, the polynucleotide includes a nucleotide sequence that is about 100% identical to SEQ ID NO: 6. In embodiments, the polynucleotide includes a nucleotide sequence that is about or at least about 80%, 85%, 90%, 95%, 96%, 97%, 98%, 99%, or 100% identical across 50, 100, 150, 200, 250, 300, or more continuous nucleotides of SEQ ID NO: 6.

In embodiments, the polynucleotide encoding the fusion protein includes a nucleotide sequence that is about or at least about 80% identical to SEQ ID NO: 10. In embodiments, the polynucleotide includes a nucleotide sequence that is about or at least about 85% identical to SEQ ID NO: 10. In embodiments, the polynucleotide includes a nucleotide sequence that is about or at least about 90% identical to SEQ ID NO: 10. In embodiments, the polynucleotide includes a nucleotide sequence that is about or at least about 95% identical to SEQ ID NO: 10. In embodiments, the polynucleotide includes a nucleotide sequence that is about or at least about 96% identical to SEQ ID NO: 10. In embodiments, the polynucleotide includes a nucleotide sequence that is about or at least about 97% identical to SEQ ID NO: 10. In embodiments, the polynucleotide includes a nucleotide sequence that is about or at least about 98% identical to SEQ ID NO: 10. In embodiments, the polynucleotide includes a nucleotide sequence that is about or at least about 99% identical to SEQ ID NO: 10. In embodiments, the polynucleotide includes a nucleotide sequence that is about 100% identical to SEQ ID NO: 10. In embodiments, the polynucleotide includes a nucleotide sequence that is about or at least about 80%, 85%, 90%, 95%, 96%, 97%, 98%, 99%, or 100% identical across 50, 100, 150, 200, 250, 300, or more continuous nucleotides of SEQ ID NO: 10.

In embodiments, the polynucleotide encoding the fusion protein includes a nucleotide sequence that is about or at least about 80% identical to SEQ ID NO: 11. In embodiments, the polynucleotide includes a nucleotide sequence that is about or at least about 85% identical to SEQ ID NO: 11. In embodiments, the polynucleotide includes a nucleotide sequence that is about or at least about 90% identical to SEQ ID NO: 11. In embodiments, the polynucleotide includes a nucleotide sequence that is about or at least about 95% identical to SEQ ID NO: 11. In embodiments, the polynucleotide includes a nucleotide sequence that is about or at least about 96% identical to SEQ ID NO: 11. In embodiments, the polynucleotide includes a nucleotide sequence that is about or at least about 97% identical to SEQ ID NO: 11. In embodiments, the polynucleotide includes a nucleotide sequence that is about or at least about 98% identical to SEQ ID NO: 11. In embodiments, the polynucleotide includes a nucleotide sequence that is about or at least about 99% identical to SEQ ID NO: 11. In embodiments, the polynucleotide includes a nucleotide sequence that is about 100% identical to SEQ ID NO: 11. In embodiments, the polynucleotide includes a nucleotide sequence that is about or at least about 80%, 85%, 90%, 95%, 96%, 97%, 98%, 99%, or 100% identical across 50, 100, 150, 200, 250, 300, or more continuous nucleotides of SEQ ID NO: 11.

In embodiments, the polynucleotide encoding the fusion protein includes a nucleotide sequence that is about or at least about 80% identical to SEQ ID NO: 12. In embodiments, the polynucleotide includes a nucleotide sequence that is about or at least about 85% identical to SEQ ID NO: 12. In embodiments, the polynucleotide includes a nucleotide sequence that is about or at least about 90% identical to SEQ ID NO: 12. In embodiments, the polynucleotide includes a nucleotide sequence that is about or at least about 95% identical to SEQ ID NO: 12. In embodiments, the polynucleotide includes a nucleotide sequence that is about or at least about 96% identical to SEQ ID NO: 12. In embodiments, the polynucleotide includes a nucleotide sequence that is about or at least about 97% identical to SEQ ID NO: 12. In embodiments, the polynucleotide includes a nucleotide sequence that is about or at least about 98% identical to SEQ ID NO: 12. In embodiments, the polynucleotide includes a nucleotide sequence that is about or at least about 99% identical to SEQ ID NO: 12. In embodiments, the polynucleotide includes a nucleotide sequence that is about 100% identical to SEQ ID NO: 12. In embodiments, the polynucleotide includes a nucleotide sequence that is about or at least about 80%, 85%, 90%, 95%, 96%, 97%, 98%, 99%, or 100% identical across 50, 100, 150, 200, 250, 300, or more continuous nucleotides of SEQ ID NO: 12.

In embodiments, the polynucleotide encoding the fusion protein includes a nucleotide sequence that is about or at least about 80% identical to SEQ ID NO: 17. In embodiments, the polynucleotide includes a nucleotide sequence that is about or at least about 85% identical to SEQ ID NO: 17. In embodiments, the polynucleotide includes a nucleotide sequence that is about or at least about 90% identical to SEQ ID NO: 17. In embodiments, the polynucleotide includes a nucleotide sequence that is about or at least about 95% identical to SEQ ID NO: 17. In embodiments, the polynucleotide includes a nucleotide sequence that is about or at least about 96% identical to SEQ ID NO: 17. In embodiments, the polynucleotide includes a nucleotide sequence that is about or at least about 97% identical to SEQ ID NO: 17. In embodiments, the polynucleotide includes a nucleotide sequence that is about or at least about 98% identical to SEQ ID NO: 17. In embodiments, the polynucleotide includes a nucleotide sequence that is about or at least about 99% identical to SEQ ID NO: 17. In embodiments, the polynucleotide includes a nucleotide sequence that is about 100% identical to SEQ ID NO: 17. In embodiments, the polynucleotide includes a nucleotide sequence that is about or at least about 80%, 85%, 90%, 95%, 96%, 97%, 98%, 99%, or 100% identical across 50, 100, 150, 200, 250, 300, or more continuous nucleotides of SEQ ID NO: 17.

In embodiments, the MDA-7/IL-24 protein retains a biological activity. As a cytokine and a member of the IL-10 cytokine gene family, MDA-7/IL-24 natively signals through receptor dimers consisting of an R1 type receptor and an R2 type receptor (IL-20R1 and IL-20R2; IL-22R1 and IL-20R2; or a unique receptor pair IL-20R1 and IL-22R1) in order to activate downstream signaling events. Assays for measuring such activities are available (see, e.g., WO2018089995A1). In embodiments, an MDA-7/IL-24 protein is a variant, homolog, or isoform that retains at least 50%, 60%, 70%, 80%, 85%, 90%, 95%, 100%, or more of the biological activity of an MDA-7/IL-24 protein of SEQ ID NO: 2 or SEQ ID NO: 3. In embodiments, the MDA-7/IL-24 protein retains at least 80% of the biological activity of an MDA-7/IL-24 protein of SEQ ID NO: 3. In embodiments, the MDA-7/IL-24 protein retains at least 90% of the biological activity of an MDA-7/IL-24 protein of SEQ ID NO: 3. In embodiments, the MDA-7/IL-24 protein is capable of activating an IL-20/IL-22 receptor complex of a cancer cell of the subject, or of a reference cell line (e.g. DU-145 cells).

In embodiments, the native signal peptide of the MDA-7/IL-24 protein is recombinantly replaced with an insulin signal peptide. In such cases, the polynucleotide does not encode the native signal peptide of MDA-7/IL-24 protein. In embodiments, the polynucleotide does not encode amino acids 1-49 of SEQ ID NO: 2. In embodiments, the MDA-7/IL-24 protein expressed from the polynucleotide, after intracellular processing for secretion, is a mature MDA-7/IL-24 protein lacking the insulin signal peptide initially translated with the MDA-7/IL-24 protein. In embodiments, the MDA-7/IL-24 protein is a truncated form of MDA-7/IL-24 protein that retains biological activity. For example, the MDA-7/IL-24 protein may lack the first 54 amino acids of SEQ ID NO: 3.

In some aspects, the present disclosure provides vectors encoding any of the polynucleotides described herein. In embodiments, the vectors are expression vectors, such that the inserted polynucleotides are operatively linked to regulatory (e.g., transcriptional and/or translational control) sequences. In this context, the term "operatively linked" means that the polynucleotide of interest is inserted into the vector such that regulatory sequences within the vector serve their intended function of regulating the transcription and/or translation of the polynucleotide, such as when expressed in a cell. The vector and expression control sequences are chosen to be compatible with an intended host or target cell. Examples of regulatory sequences include, but are not limited to, promoters, enhancers and other expression control elements (e.g., polyadenylation signals). Non-limiting examples of regulatory sequences for use in expression a protein in a mammalian cell include: promoters and/or enhancers derived from cytomegalovirus (CMV), Simian Virus 40 (SV40), adenovirus, (e.g., the adenovirus major late promoter (AdMLP) and polyoma; nonviral regulatory sequences, such as the ubiquitin promoter or β-globin promoter; and sequences from different sources, such as the SRα promoter system, which contains sequences from the SV40 early promoter and the long terminal repeat of human T cell leukemia virus type 1.

In embodiments, the vector is a plasmid vector. In embodiments, the vector is a viral vector, such as an adenoviral vector (Ad), an associated-adenoviral vector (AAV), a lentiviral vector, a retroviral vector, a herpesvirus, a vaccinia virus, a genetically modified HIV, vesicular stomatatitis virus, or other suitable viral vector. In embodiments, the virus is an adenovirus. A variety of suitable adenoviruses are available. Non-limiting examples of adenoviruses that may be used in the expression of an MDA-7/IL-24 protein include those described in WO2018089995A1, WO2017062708A1, US20180243382A1, US20160008413A1, and Dash et al., Cancer Res 2014; 74:563-74. In embodiments, the virus (e.g., an adenovirus) is a replication incompetent adenovirus, such that viral replication in a target cell is diminished or eliminated relative to a corresponding wild-type virus. In embodiments, viral replication is under control of a cancer-specific promoter, such that viral replication is higher in cancer cells than in non-cancer cells. A non-limiting example of a cancer-specific promoter is the cancer-selective Progression Elevated Gene-3 (PEG-3) promoter. Adenoviral replication can be made cancer-specific by, for example, placing E1A and E1B genes under control of the PEG-3 promoter.

In some aspects, the present disclosure provides proteins produced by expressing a polynucleotide described herein. In embodiments, protein is a protein encoded by a polynucleotide or vector disclosed herein, or an expression product thereof. In embodiments, the protein is a fusion protein that includes a signal peptide or a portion thereof. The fusion protein may be processed by a cell from a precursor form comprising an insulin signal peptide to a mature form in which the signal peptide is partially or completely removed. Thus, in some embodiments, the protein expression product does not include all or any of the insulin signal peptide.

In some aspects, the present disclosure provides a cell, or population of cells, that include a polynucleotide or vector disclosed herein. In embodiments, the cell is a cancer cell, such as a prostate cancer cell, a breast cancer cell, or a lung cancer cell. In embodiments, the cancer cell is a prostate cancer cell. In embodiments, the cell is an immune cell, such as a T cell. In embodiments the cell is a CD8+ T cell. In embodiments, cells are produced by contacting a particular cell or cell population with a polynucleotide or vector described herein. For example, T cells including a polynucleotide of the present disclosure can be produced by contacting T cells with an adenovirus containing an adenoviral including a polynucleotide of the present disclosure.

In some aspects, the present disclosure provides a composition including (a) a polynucleotide or vector disclosed herein, and (b) a pharmaceutically acceptable excipient. In embodiments, the composition further comprises one or more additional agents, or is coadministered with one or more additional agents. In embodiments, the one or more additional agents is an Akt inhibitor, an Mcl-1 inhibitor, or a combination thereof. In embodiments, the one or more additional agents is a phosphoinositide 3-kinase (PI3K) inhibitor, an Mcl-1 inhibitor, or a combination thereof. In embodiments, the additional agent is a PI3K inhibitor (e.g., LY294002). In embodiments, the additional agent is an Mcl-1 inhibitor (e.g., BI-97D6, BI-97CI, UMI-77, Marinopyrrole A, or A-1210477).

A variety of Akt inhibitors are available, which may be subdivided into several classes. A first class contains ATP competitive inhibitors of Akt and includes compounds such as CCT128930 and GDC-0068, which inhibit Akt2 and Akt1. This category also includes the pan-Akt kinase inhibitors such as GSK2110183 (afuresertib), GSK690693, and AT7867. A second class contains lipid-based Akt inhibitors that act by inhibiting the generation of PIP3 by PI3K. This mechanism is employed by phosphatidylinositol analogs such as Calbiochem Akt Inhibitors I, II and III or other PI3K inhibitors such as PX-866. This category also includes compounds such as Perifosine (KRX-0401) (Aeterna Zentaris/Keryx). A third class contains a group of compounds called pseudosubstrate inhibitors. These include compounds such as AKTide-2 T and FOXO3 hybrid. A fourth class consists of allosteric inhibitors of AKT kinase domain, and include compounds such as MK-2206 (8-[4-(1-aminocyclobutyl)phenyl]-9-phenyl-2H-[1,2,4]triazolo[3,4-f][1,6]naphthyridin-3-one; dihydrochloride) (Merck & Co.) (see, e.g., U.S. Pat. No. 7,576,209). A fifth class includes antibodies, such as GST-anti-Akt1-MTS. A sixth class comprises compounds that interact with the PH domain of Akt, and includes Triciribine and PX-316. Other compounds that act as AKT inhibitors include, for example, GSK-2141795 (GlaxoSmithKline), VQD-002, miltefosine, AZD5363, GDC-0068, RX-0201 (an antisense oligonucleotide), PBI-05204, SR13668, and API-1.

A variety of PI3K inhibitors are available, some of which are noted above. Additional examples include, but are not limited to, wortmannin (an irreversible inhibitor of PI3K), demethoxyviridin (a derivative of wortmannin), LY294002 (a reversible inhibitor of PI3K); BKM120 (Buparlisib), Idelalisib (a PI3K Delta inhibitor), duvelisib (IPI-145, an inhibitor of PI3K delta and gamma), alpelisib (BYL719, an alpha-specific PI3K inhibitor), TGR 1202 (also known as RP5264, an oral PI3K delta inhibitor), copanlisib (BAY 80-6946, an inhibitor PI3Kα,δ), BEZ235, RP6530, TGR 1201, SFI126, INK1117, GDC-0941, XL147 (SAR245408), XL765 (SAR245409), Palomid 529, GSK1059615, ZSTK474, PWT33597, IC87114, TG100-115, CAL263, RP6503, PI-103, GNE-477, CUDC-907, AEZS-136, GDC-0980, and GDC-0032. In embodiments, the PI3K inhibitor is LY294002.

A variety of Mcl-1 inhibitors are available. Non-limiting examples of Mcl-1 inhibitors include BI97C10, BI112D1, gossypol (AT-101, Ascenta Therapeutics), obatoclax (GX15-070, Cephalon), MG-132, MIM1, sabutoclax (B197C1, Oncothyreon), and TW-37. Further examples of Mcl-1 inhibitors are disclosed in Varadarajan et al. (Cell Death Differ. 2013 Nov.; 20(11): 1475-1484), Tanaka et al. (J Med Chem 56(23):9635-9645 (2013)), Friberg, et al. (J Med Chem 56(1):15-30 (2013)), US20150045357A1, US20150051249A1, US20130035304A1, US20090054402A1, and US20110112112A1. In embodiments, the Mcl-1 inhibitor is BI-97D6.

In embodiments, compositions are in an amount effective to prevent or treat bone metastasis. In embodiments, the effective amount comprises an amount of the composition (or a component thereof) that is substantially non-toxic to primary bone marrow cells or normal primary human prostate epithelial cells. In embodiments, an amount of a compound is substantially non-toxic to primary bone marrow cells when the amount induces no increased cell death relative to the absence of the compound, or any increase in cell death is less than 20%, 15%, 10%, 5%, or less relative to the absence of the compound. Toxicity effects can be measured, for example, using commercially available live-dead cell staining assays.

In embodiments, the effective amount comprises an amount of the composition (or a component thereof) that is an amount that inhibits osteoclast differentiation. In embodiments, inhibition of osteoclast differentiation comprises a reduction in the number of bone marrow cells that differentiate into osteoclasts by at least 5%, 10%, 15%, 20%, 25%, 30%, 35%, 40%, 50%, 60%, 70%, or more. In embodiments, differentiation of bone marrow cells to osteoclasts is reduced by at least 25%. Effects on osteoclast differentiation can be measured, for example, by comparing treated and untreated cells in culture, or by comparing the number of osteoclasts in a bone marrow sample from a treated subject to the number of osteoclasts in a comparable bone marrow sample from an untreated subject.

In embodiments, the composition comprises an amount of an Mcl-1 inhibitor (e.g., BI-97D6), such as at least about 0.1 mg/kg, 0.2 mg/kg, 0.3 mg/kg, 0.4 mg/kg, 0.5 mg/kg, 0.75 mg/kg, 1 mg/kg, 1.25 mg/kg, 1.5 mg/kg, 2 mg/kg, 3 mg/kg, 4 mg/kg, or 5 mg/kg inhibitor is administered to the subject. In embodiments, between 0.1 mg/kg and 5 mg/kg, between 0.2 mg/kg and 3 mg/kg, or between 0.5 mg/kg and 2 mg/kg are administered to the subject. In embodiments, the composition comprises the Mcl-1 inhibitor at a dose of about 1.5 mg/kg. In embodiments, the Mcl-1 inhibitor is administered separately from a polynucleotide, vector, cell, or protein of the present disclosure, but according to the same dosing schedule.

Methods

In some aspects, the present disclosure provides methods of treating cancer, including treating or preventing metastasis. In embodiments, the methods include administering to a subject in need thereof a polynucleotide, a vector, or a composition described herein. In embodiments, the method includes administering an Mcl-1 inhibitor, such as BI-97D6, BI-97C1, UMI-77, Marinopyrrole A, or A-1210477. In embodiments, the method includes administering a PI3K inhibitor, such as LY294002. In embodiments, the cancer is prostate cancer. In embodiments, the prostate cancer includes cancer cells having an increased expression of one or more of Mcl-1, RANKL, Bcl-2, Bcl-xL, and Akt, relative to normal prostate cells.

In embodiments, administering a composition comprising the MDA-7/IL-24 protein comprises administering to a target tissue, such as to a tumor, a site from which a tumor has been surgically removed, and/or to a bone of a subject. In embodiments, administering to the target tissue comprises injection into or adjacent to the target tissue, or topical application to the target tissue. In embodiments, the composition is delivered distally to the target tissue, but is formulated to traffic the MDA-7/IL-24 protein (or polynucleotide or vector encoding the protein) to the target tissue. In embodiments, a moiety that traffics to a particular tissue, such as a cancer tissues and/or a bone tissue, is complexed with the MDA-7/IL-24 protein (or polynucleotide or vector encoding the protein). Complexing can be directly with the targeting moiety, such as a covalent or non-covalent interaction. Complexing can be indirect, such that the MDA-7/IL-24 protein (or polynucleotide or vector encoding the protein) and the targeting moiety are separated by one or more other molecules joining the two, via covalent or non-covalent interactions. In general, a targeting moiety is a moiety able to bind to or otherwise associate with a biological entity (e.g., a membrane component, a cell surface receptor, cell specific membrane antigen, or the like), with a higher affinity than one or more non-target biological entity (e.g., cell surface components of one or more different tissues). A targeting moiety typically allows a cargo (e.g., a polynucleotide, vector, or protein) to become localized at a particular targeting site to a higher degree than elsewhere in the body of the subject, or to a higher degree at the target site than would be accomplished in the absence of the targeting moiety. Non-limiting examples of targeting moieties include antibodies, antigen-binding antibody fragments, aptamers, peptides, hormones, growth factors, ligands (e.g., receptor ligands), small molecules, and the like. Illustrative examples of targeting moieties that traffic to bone are described in US20120028350A1, US20160052968A1, US20040038946A1, and US20180208650A1.

In embodiments, administration comprises ultrasound-targeted microbubble-destruction (UTMD), allowing for directed delivery of a cargo (e.g., a polynucleotide, vector, or protein) within or complexed to the microbubble to a target tissue. For example, a composition of the present disclosure may be complexed with microbubbles, administered intravenously, then released at a target tissue by applying ultrasound at the target tissue. US20180243382A1 and US20160108429A1 provide an illustrative examples of microbubble delivery technology. In embodiments, the microbubbles are complexed with a targeting moiety that traffics the microbubbles to a particular tissue, such as a cancer tissue, cancer vasculature, or a bone tissue.

In embodiments, metastasis (e.g., bone metastasis) of any of a variety of cancers is treated or prevented. Some cancers have a higher propensity to metastasize to bone. Examples include, without limitation, prostate cancer, breast cancer, lung cancer, kidney cancer, and thyroid cancer. In embodiments, the cancer is a prostate cancer. Various gene expression signatures can be used to distinguish cancer cells from non-cancer cells, cancers of one tissue from cancers of another tissue, and metastatic cancers from non-metastatic cancers. In embodiments, the cancer is a prostate cancer having an increased expression of one or more of Mcl-1, RANKL, Bcl-2, Bcl-xL, and Akt, relative to normal prostate cells, such as a reference prostate cell line or non-cancerous prostate cells of the subject with prostate cancer.

In embodiments, a composition of the present disclosure is administered in an effective amount. In embodiments, the effective amount is an amount of the composition effective to prevent or treat bone metastasis. In embodiments, the effective amount comprises an amount of the composition (or a component thereof) that is substantially non-toxic to primary bone marrow cells or normal primary human prostate epithelial cells. In embodiments, an amount of a compound is substantially non-toxic to primary bone marrow cells when the amount induces no increased cell death relative to the absence of the compound, or any increase in cell death is less than 20%, 15%, 10%, 5%, or less relative to the absence of the compound. Toxicity effects can be measured, for example, using commercially available live-dead cell staining assays. Additional examples of effective amounts are described herein, such as with regard to the various compositions of the disclosure.

In some aspects, the present disclosure provides uses of a composition in the manufacture of a medicament for the treatment of cancer in a subject in need thereof. In embodiments, the composition includes a polynucleotide, vector, cell, or composition described herein.

In some aspects, the present disclosure provides methods of producing an MDA-7/IL-24 protein by expressing a polynucleotide or vector of the present disclosure in a cell. In embodiments, the method further includes the step of purifying the MDA-7/IL-24 protein. The MDA-7/IL-24 produced according to these methods can be any MDA-7/IL-24 described herein. In embodiments, the MDA-7/IL-24 protein is secreted from a host cell, and purification may comprise purification without cell lysis. The mode of purification will also depend on the nature of the protein produced. For example, the MDA-7/IL-24 protein produced by the host cell can comprise additional elements, such as a protein tag to facilitate purification (e.g., a His, FLAG, or HA tag). A protein tag facilitates purification using a cognate binding partner (e.g., nickel in the case of a His tag), which may be adhered to a substrate. In embodiments, an MDA-7/IL-24 protein initially produced with a purification tag is treated to remove the tag before administration to a subject. In embodiments, the MDA-7/IL-24 protein produced by a host cell does not comprise a purification tag. In such cases, purification may comprise purification using reagents that bind to the MDA-7/IL-24 protein (e.g., antibodies adhered to a substrate). In embodiments, purification comprises removal of components of a media or lysate other than the MDA-7/IL-24 protein. For example, a lysate or cellular suspension can be centrifuged to produce a pellet of cells or cellular debris, and the supernatant separated to a different container, thereby purifying the MDA-7/IL-24 protein by separation of such cells or cellular debris.

SEQUENCES (nucleotide sequence encoding an MDA-7/IL-24 protein)
SEQ ID NO: 1
atgaattttcaacagaggctgcaaagcctgtggactttagccagaccettctgccctcctttg ctggcgacagcctctcaaatgcagatggttgtgctcccttgcctgggttttaccctgcttctc tggagccaggtatcaggggcccagggccaagaattccactttgggccctgccaagtgaagggg gttgttccccagaaactgtgggaagccttctgggctgtgaaagacactatgcaagctcaggat aacatcacgagtgcccggctgctgcagcaggaggttctgcagaacgtctcggatgctgagagc tgttaccttgtccacaccctgctggagttctacttgaaaactgttttcaaaaactaccacaat agaacagttgaagtcaggactctgaagtcattctctactctggccaacaactttgactcatcg tgtcacaactgcaacccagtcaagaaaatgagatgttttccatcagagacagtgcacacaggc ggttcctgctattccggagagcatttaaacagttggacgtagaagcagctctgaccaaagccc ttggggaagtggacattcttctgacctggatgcagaaattctacaagctctga (amino acid sequence of an MDA-7/IL-24 protein)
SEQ ID NO: 2
MNFQQRLQSLWTLARPFCPPLLATASQMQMVVLPCLGFTLLLWSQVSGAQGQEFHFGP

CQVKGVVPQKLWEAFWAVKDTMQAQDNITSARLLQQEVLQNVSDAESCYLVHTLLEFY

LKTVFKNYHNRTVEVRTLKSFSTLANNFVLIVSQLQPSQENEMFSIRDSAHRRFLLFR

RAFKQLDVEAALTKALGEVDILLTWMQKFYKL (amino acid sequence of an MDA-7/IL-24 protein)
SEQ ID NO: 3
QGQEFHFGPCQVKGVVPQKLWEAFWAVKDTMQAQDNITSARLLQQEVLQNVSDAESCY

LVHTLLEFYLKTVFKNYHNRTVEVRTLKSFSTLANNFVLIVSQLQPSQENEMFSIRDS

AHRRFLLFRRAFKQLDVEAALTKALGEVDILLTWMQKFYKL (amino acid sequence of an MDA-7/IL-24 protein)
SEQ ID NO: 4
ESCYLVHTLLEFYLKTVFKNYHNRTVEVRTLKSFSTLANNFVLIVSQLQPSQENEMFS

IRDSAHRRFLLFRRAFKQLDVEAALTKALGEVDILLTWMQKFYKL (amino acid sequence of an insulin signal peptide (sp))
SEQ ID NO: 5
MALWMRLLPLLALLALWGPDPAAA (Encoding an insulin(sp)-MDA-7 sequence)
SEQ ID NO: 6
ATG GCG CTG TGG ATG CGC CTG CTG CCG CTG CTG GCG CTG CTG GCG CTG

TGG GGC CCA GAT CCG GCG GCG GCG CAT CAC CAT CAC CAT CAC GAG AAC

CTG TAC TTC CAG GGC ATG CAA GAA TTC CAC TTT GGG CCC TGC CAA GTG

AAG GGG GTT GTT CCC CAG AAA CTG TGG GAA GCC TTC TGG GCT GTG AAA

GAC ACT ATG CAA GCT CAG GAT AAC ATC ACG AGT GCC CGG CTG CTG CAG

CAG GAG GTT CTG CAG AAC GTC TCG GAT GCT GAG AGC TGT TAC CTT GTC

CAC ACC CTG CTG GAG TTC TAC TTG AAA ACT GTT TTC AAA AAC TAC CAC

AAT AGA ACA GTT GAA GTC AGG ACT CTG AAG TCA TTC TCT ACT CTG GCC

AAC AAC TTT GTT CTC ATC GTG TCA CAA CTG CAA CCC AGT CAA GAA AAT

GAG ATG TTT TCC ATC AGA GAC AGT GCA CAC AGG CGG TTC CTG CTA TTC

CGG AGA GCA TTC AAA CAG TTG GAC GTA GAA GCA GCT CTG ACC AAA GCC

CTT GGG GAA GTG GAC ATT CTT CTG ACC TGG ATG CAG AAA TTC TAC AAG

CTC TAG (Encoding a Flt3(sp)-MDA-7 sequence)
SEQ ID NO: 7
ATG ACA GTG CTG GCG CCA GCC TGG AGC CCA ACA ACC TAT CTC CTC CTG

CTG CTG CTG AGC GGA TCC ATG CAA GAA TTC CAC TTT GGG CCC TGC

CAA GTG AAG GGG GTT GTT CCC CAG AAA CTG TGG GAA GCC TTC TGG GCT

GTG AAA GAC ACT ATG CAA GCT CAG GAT AAC ATC ACG AGT GCC CGG CTG

CTG CAG CAG GAG GTT CTG CAG AAC GTC TCG GAT GCT GAG AGC TGT TAC

CTT GTC CAC ACC CTG CTG GAG TTC TAC TTG AAA ACT GTT TTC AAA AAC

TAC CAC AAT AGA ACA GTT GAA GTC AGG ACT CTG AAG TCA TTC TCT ACT

CTG GCC AAC AAC TTT GTT CTC ATC GTG TCA CAA CTG CAA CCC AGT CAA

GAA AAT GAG ATG TTT TCC ATC AGA GAC AGT GCA CAC AGG CGG TTT CTG

CTA TTC CGG AGA GCA TTC AAA CAG TTG GAC GTA GAA GCA GCT CTG ACC

AAA GCC CTT GGG GAA GTG GAC ATT CTT CTG ACC TGG ATG CAG AAA TTC

TAC AAG CTC GGG GGT TCT CAT CAT CAT CAT CAT CAT TGA (Encoding a BM40(sp)-MDA-7 sequence)

SEQ ID NO: 8

ATG AGA GCC TGG ATC TTT TTT CTG CTC TGC CTC GCT GGC AGA GCC CTG

GCT CAT CAC CAT CAC CAT CAC GAG AAC CTG TAC TTC CAG GGC ATG CAA

GAA TTC CAC TTT GGG CCC TGC CAA GTG AAG GGG GTT GTT CCC CAG AAA

CTG TGG GAA GCC TTC TGG GCT GTG AAA GAC ACT ATG CAA GCT CAG GAT

AAC ATC ACG AGT GCC CGG CTG CTG CAG CAG GAG GTT CTG CAG AAC GTC

TCG GAT GCT GAG AGC TGT TAC CTT GTC CAC ACC CTG CTG GAG TTC TAC

TTG AAA ACT GTT TTC AAA AAC TAC CAC AAT AGA ACA GTT GAA GTC AGG

ACT CTG AAG TCA TTC TCT ACT CTG GCC AAC AAC TTT GTT CTC ATC GTG

TCA CAA CTG CAA CCC AGT CAA GAA AAT GAG ATG TTT TCC ATC AGA GAC

AGT GCA CAC AGG CGG TTT CTG CTA TTC CGG AGA GCA TTC AAA CAG TTG

GAC GTA GAA GCA GCT CTG ACC AAA GCC CTT GGG GAA GTG GAC ATT CTT

CTG ACC TGG ATG CAG AAA TTC TAC AAG CTC TGA (Encoding an IL-2(sp)-MDA-7 sequence)

SEQ ID NO: 9

ATG CAG CTG CTG TCA TGC ATC GCA TTG ATC TTG GCG CTG GTG ATG CAA

GAA TTC CAC TTT GGG CCC TGC CAA GTG AAG GGG GTT GTT CCC CAG AAA

CTG TGG GAA GCC TTC TGG GCT GTG AAA GAC ACT ATG CAA GCT CAG GAT

AAC ATC ACG AGT GCC CGG CTG CTG CAG CAG GAG GTT CTG CAG AAC GTC

TCG GAT GCT GAG AGC TGT TAC CTT GTC CAC ACC CTG CTG GAG TTC TAC

TTG AAA ACT GTT TTC AAA AAC TAC CAC AAT AGA ACA GTT GAA GTC AGG

ACT CTG AAG TCA TTC TCT ACT CTG GCC AAC AAC TTT GTT CTC ATC GTG

TCA CAA CTG CAA CCC AGT CAA GAA AAT GAG ATG TTT TCC ATC AGA GAC

AGT GCA CAC AGG CGG TTT CTG CTA TTC CGG AGA GCA TTC AAA CAG TTG

GAC GTA GAA GCA GCT CTG ACC AAA GCC CTT GGG GAA GTG GAC ATT CTT

CTG ACC TGG ATG CAG AAA TTC TAC AAG CTC TGA (Encoding an MDA-7(K122R) sequence)

SEQ ID NO: 10

ATG AAT TTT CAA CAG AGG CTG CAA AGC CTG TGG ACT TTA GCC AGA CCC

TTC TGC CCT CCT TTG CTG GCG ACA GCC TCT CAA ATG CAG ATG GTT GTG

CTC CCT TGC CTG GGT TTT ACC CTG CTT CTC TGG AGC CAG GTA TCA GGG

GCC CAG GGC CAA GAA TTC CAC TTT GGG CCC TGC CAA GTG AAG GGG GTT

GTT CCC CAG AAA CTG TGG GAA GCC TTC TGG GCT GTG AAA GAC ACT ATG

CAA GCT CAG GAT AAC ATC ACG AGT GCC CGG CTG CTG CAG CAG GAG GTT

CTG CAG AAC GTC TCG GAT GCT GAG AGC TGT TAC CTT GTC CAC ACC CTG

CTG GAG TTC TAC TTG AAA ACT GTT TTC AGA AAC TAC CAC AAT AGA ACA

GTT GAA GTC AGG ACT CTG AAG TCA TTC TCT ACT CTG GCC AAC AAC TTT

GTT CTC ATC GTG TCA CAA CTG CAA CCC AGT CAA GAA AAT GAG ATG TTT

TCC ATC AGA GAC AGT GCA CAC AGG CGG TTT CTG CTA TTC CGG AGA GCA

TTC AAA CAG TTG GAC GTA GAA GCA GCT CTG ACC AAA GCC CTT GGG GAA

GTG GAC ATT CTT CTG ACC TGG ATG CAG AAA TTC TAC AAG CTC TGA

-continued (Encoding an insulin(sp)-MDA-7-K122R)
SEQ ID NO: 11
ATG GCG CTG TGG ATG CGC CTG CTG CCG CTG CTG GCG CTG CTG GCG CTG

TGG GGC CCA GAT CCG GCG GCG GCG CAT CAC CAT CAC CAT CAC GAG AAC

CTG TAC TTC CAG GGC ATG CAA GAA TTC CAC TTT GGG CCC TGC CAA GTG

AAG GGG GTT GTT CCC CAG AAA CTG TGG GAA GCC TTC TGG GCT GTG AAA

GAC ACT ATG CAA GCT CAG GAT AAC ATC ACG AGT GCC CGG CTG CTG CAG

CAG GAG GTT CTG CAG AAC GTC TCG GAT GCT GAG AGC TGT TAC CTT GTC

CAC ACC CTG CTG GAG TTC TAC TTG AAA ACT GTT TTC AGA AAC TAC CAC

AAT AGA ACA GTT GAA GTC AGG ACT CTG AAG TCA TTC TCT ACT CTG GCC

AAC AAC TTT GTT CTC ATC GTG TCA CAA CTG CAA CCC AGT CAA GAA AAT

GAG ATG TTT TCC ATC AGA GAC AGT GCA CAC AGG CGG TTC CTG CTA TTC

CGG AGA GCA TTC AAA CAG TTG GAC GTA GAA GCA GCT CTG ACC AAA GCC

CTT GGG GAA GTG GAC ATT CTT CTG ACC TGG ATG CAG AAA TTC TAC AAG

CTC TAG (Encoding an Insulin(sp)-M4)
SEQ ID NO: 12
ATG GCG CTG TGG ATG CGC CTG CTG CCG CTG CTG GCG CTG CTG GCG CTG

TGG GGC CCA GAT CCG GCG GCG GCG CAT CAC CAT CAC CAT CAC GAG AAC

CTG TAC TTC CAG GGC ATG GAG AGC TGT TAC CTT GTC CAC ACC CTG CTG

GAG TTC TAC TTG AAA ACT GTT TTC AAA AAC TAC CAC AAT AGA ACA GTT

GAA GTC AGG ACT CTG AAG TCA TTC TCT ACT CTG GCC AAC AAC TTT GTT

CTC ATC GTG TCA CAA CTG CAA CCC AGT CAA GAA AAT GAG ATG TTT TCC

ATC AGA GAC AGT GCA CAC AGG CGG TTC CTG CTA TTC CGG AGA GCA TTC

AAA CAG TTG GAC GTA GAA GCA GCT CTG ACC AAA GCC CTT GGG GAA GTG

GAC ATT CTT CTG ACC TGG ATG CAG AAA TTC TAC AAG CTC TAG (Encoding an IL2(sp)-M4)
SEQ ID NO: 13
ATG CAG CTG CTG TCA TGC ATC GCA TTG ATC TTG GCG CTG GTG ATG GAG

AGC TGT TAC CTT GTC CAC ACC CTG CTG GAG TTC TAC TTG AAA ACT GTT

TTC AAA AAC TAC CAC AAT AGA ACA GTT GAA GTC AGG ACT CTG AAG TCA

TTC TCT ACT CTG GCC AAC AAC TTT GTT CTC ATC GTG TCA CAA CTG CAA

CCC AGT CAA GAA AAT GAG ATG TTT TCC ATC AGA GAC AGT GCA CAC AGG

CGG TTT CTG CTA TTC CGG AGA GCA TTC AAA CAG TTG GAC GTA GAA GCA

GCT CTG ACC AAA GCC CTT GGG GAA GTG GAC ATT CTT CTG ACC TGG ATG

CAG AAA TTC TAC AAG CTC TGA (Encoding a Flt-3(sp)-M4)
SEQ ID NO: 14
ATG ACA GTG CTG GCG CCA GCC TGG AGC CCA ACA ACC TAT CTC CTC CTG

CTG CTG CTG CTG AGC GGA TCC GAG AGC TGT TAC CTT GTC CAC ACC CTG

CTG GAG TTC TAC TTG AAA ACT GTT TTC AAA AAC TAC CAC AAT AGA ACA

GTT GAA GTC AGG ACT CTG AAG TCA TTC TCT ACT CTG GCC AAC AAC TTT

GTT CTC ATC GTG TCA CAA CTG CAA CCC AGT CAA GAA AAT GAG ATG TTT

TCC ATC AGA GAC AGT GCA CAC AGG CGG TTT CTG CTA TTC CGG AGA GCA

-continued

```
TTC AAA CAG TTG GAC GTA GAA GCA GCT CTG ACC AAA GCC CTT GGG GAA

GTG GAC ATT CTT CTG ACC TGG ATG CAG AAA TTC TAC AAG CTC GGG GGT

TCT CAT CAT CAT CAT CAT CAT TGA
```

(Encoding an MDA-7(sp)-M4)

SEQ ID NO: 15

```
ATG AAT TTT CAA CAG AGG CTG CAA AGC CTG TGG ACT TTA GCC AGA CCC

TTC TGC CCT CCT TTG CTG GCG ACA GCC TCT CAA ATG CAG ATG GTT GTG

CTC CCT TGC CTG GGT TTT ACC CTG CTT CTC TGG AGC CAG GTA TCA GGG

GCC CAG GGC GGA TCC GAG AGC TGT TAC CTT GTC CAC ACC CTG CTG GAG

TTC TAC TTG AAA ACT GTT TTC AAA AAC TAC CAC AAT AGA ACA GTT GAA

GTC AGG ACT CTG AAG TCA TTC TCT ACT CTG GCC AAC AAC TTT GTT CTC

ATC GTG TCA CAA CTG CAA CCC AGT CAA GAA AT GAG ATG TTT TCC ATC

AGA GAC AGT GCA CAC AGG CGG TTT CTG CTA TTC CGG AGA GCA TTC AAA

CAG TTG GAC GTA GAA GCA GCT CTG ACC AAA GCC CTT GGG GAA GTG GAC

ATT CTT CTG ACC TGG ATG CAG AAA TTC TAC AAG CTC TGA
```

(Encoding a Flt-3(sp)-M4(K122R))

SEQ ID NO: 16

```
ATG ACA GTG CTG GCG CCA GCC TGG AGC CCA ACA ACC TAT CTC CTC CTG

CTG CTG CTG CTG AGC GGA TCC GAG AGC TGT TAC CTT GTC CAC ACC CTG

CTG GAG TTC TAC TTG AAA ACT GTT TTC AGA AAC TAC CAC AAT AGA ACA

GTT GAA GTC AGG ACT CTG AAG TCA TTC TCT ACT CTG GCC AAC AAC TTT

GTT CTC ATC GTG TCA CAA CTG CAA CCC AGT CAA GAA AAT GAG ATG TTT

TCC ATC AGA GAC AGT GCA CAC AGG CGG TTT CTG CTA TTC CGG AGA GCA

TTC AAA CAG TTG GAC GTA GAA GCA GCT CTG ACC AAA GCC CTT GGG GAA

GTG GAC ATT CTT CTG ACC TGG ATG CAG AAA TTC TAC AAG CTC GGG GGT

TCT CAT CAT CAT CAT CAT CAT TGA
```

(Encoding an insulin(sp)-M4(K122R))

SEQ ID NO: 17

```
ATG GCG CTG TGG ATG CGC CTG CTG CCG CTG CTG GCG CTG CTG GCG CTG

TGG GGC CCA GAT CCG GCG GCG GCG CAT CAC CAT CAC CAT CAC GAG AAC

CTG TAC TTC CAG GGC ATG GAG AGC TGT TAC CTT GTC CAC ACC CTG CTG

GAG TTC TAC TTG AAA ACT GTT TTC AGA AAC TAC CAC AAT AGA ACA GTT

GAA GTC AGG ACT CTG AAG TCA TTC TCT ACT CTG GCC AAC AAC TTT GTT

CTC ATC GTG TCA CAA CTG CAA CCC AGT CAA GAA AAT GAG ATG TTT TCC

ATC AGA GAC AGT GCA CAC AGG CGG TTC CTG CTA TTC CGG AGA GCA TTC

AAA CAG TTG GAC GTA GAA GCA GCT CTG ACC AAA GCC CTT GGG GAA GTG

GAC ATT CTT CTG ACC TGG ATG CAG AAA TTC TAC AAG CTC TAG
```

(amino acid sequence of an MDA-7/EL-24 protein (K122R))

SEQ ID NO: 18

ESCYLVHTLLEFYLKTVFRNYHNRTVEVRTLKSFSTLANNFVLIVSQLQPSQENEMFSrR

DSAHRRFLLFRRAFKQLDVEAALTKALGEVDILLTWMQKFYKL

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

Example 1: Genetic Engineering of the Tumor Suppressor Gene MDA-7/IL-24 to Enhance Its Anti-Cancer Activity Melanoma differentiation associated gene-7/Interleukin-24 (MDA-7/IL-24) is a member of the IL-10 family of secreted interleukins and has tumor suppressive properties across different cancer subtypes. MDA-7/IL-24 is a secreted protein that mediates at least some of its tumor suppressive functions through its cell surface receptors.

In an effort to enhance its anti-cancer activity, genetic engineering experiments were conducted to enhance MDA-7/IL-24 secretion. Five different signal peptides (abbreviated "sp") were introduced, linked to MDA-7/IL-24, and assessed for protein secretion. A schematic illustration of the MDA-7/IL-24 modifications is shown in FIG. 1. The five signal peptides tested were endogenous human MDA-7/IL-24, human IL-2, human Insulin, Flt-3 and human BM40 (osteonectin/SPARC) signal peptides. The constructs were designated MDA-7(sp)-MDA-7 (wild type MDA-7 signal peptide), IL-2(sp)-MDA-7, Insulin(sp)-MDA-7, Flt-3(sp)-MDA-7 and BM40(sp)-MDA-7, respectively. Each of these constructs also included a Histidine-tag. These constructs were transfected into DU-145 cells (human prostate cancer cells).

Figure 2:
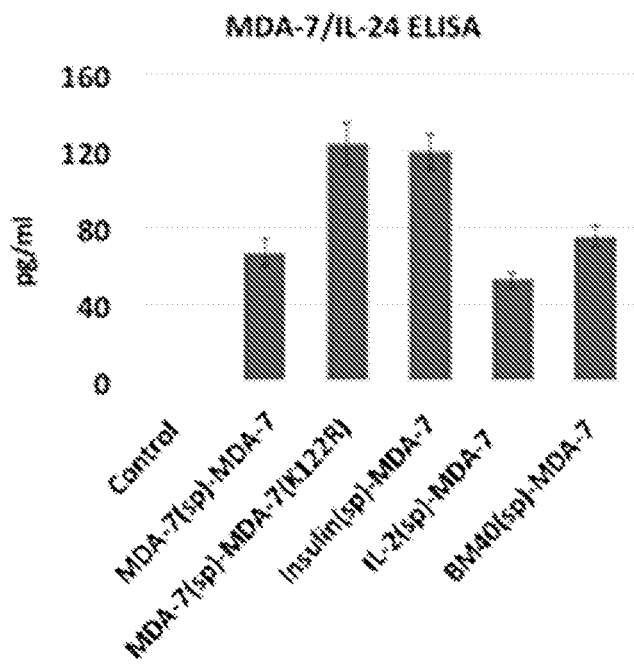
FIG. 2 shows examples results for MDA-7/IL-24 protein expression determined using ELISA in conditioned media of DU145 cells after transfection with the indicated plasmids.
Figure 3:
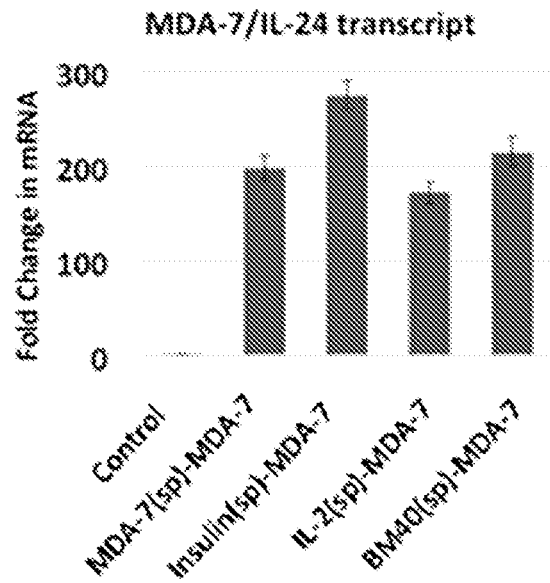
FIG. 3 shows example results for MDA-7/IL-24 expression assessed at the transcript level in DU145 cells after transfection with indicated plasmids.

The presence of MDA-7/IL-24 in the conditioned media was assessed by enzyme-linked immunosorbent assay (ELISA) and results are shown in FIG. 2. Transcript level of MDA-7/IL-24 in transfected cell lysates was assessed and the fold change in mRNA is shown in FIG. 3. The data demonstrated that the insulin signal peptide dramatically enhanced MDA-7/IL-24 protein secretion as compared to the other four (4) signal peptides.

Figure 4:
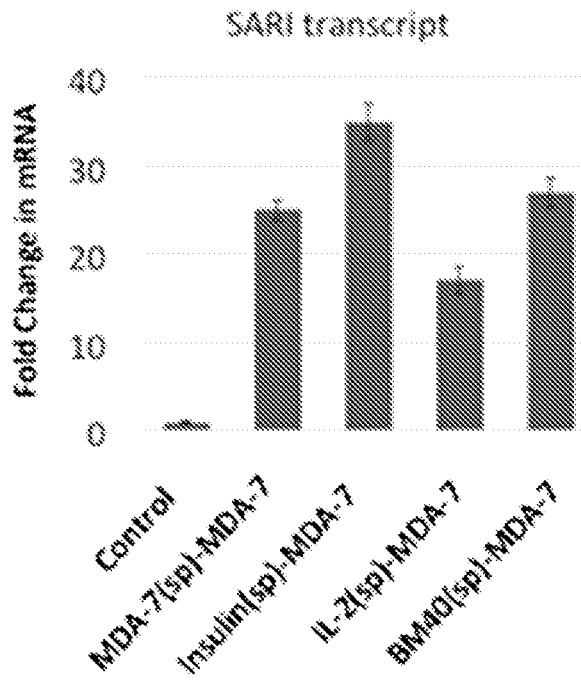
FIG. 4 shows example results for SARI expression assessed at the transcript level in DU145 cells after transfection with indicated plasmids.
Figure 5:
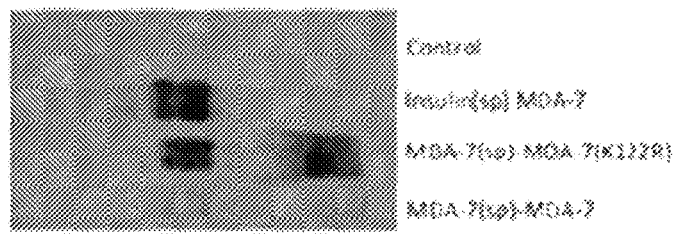
FIG. 5 shows example images illustrating MDA-7/IL-24 expression from the conditioned media of HeLa cells transfected with the indicated construct.
Figure 5:
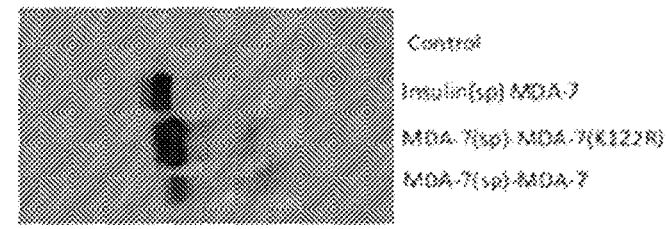
Figure 6:
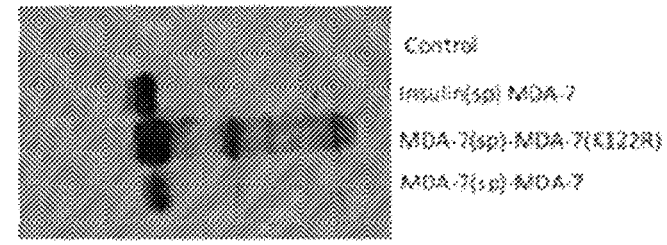
FIG. 6 shows example images illustrating MDA-7/IL-24 expression from the lysate of HeLa cells transfected with the indicated construct.

To confirm that enhanced MDA-7/IL-24 secretion resulted in enhanced downstream signaling, experiments were conducted to assess the expression of a downstream target of MDA-7/IL-24, the Suppressor of AP-1 regulated by interferon protein (SARI). SARI expression was determined at the transcript level in DU-145 cells after transfection with the indicated plasmids. As shown in FIG. 4, the highest SARI expression was observed in Insulin(sp)-MDA-7 transfected cells. The protein expression of MDA-7/IL-24 from the conditioned media (FIG. 5) and cell lysates (FIG. 6) of HeLa cells transfected with full length MDA-7 and Insulin (sp)-MDA-7 was assayed. Results showed a dramatic increase in MDA-7/IL-24 protein secretion with the insulin signal peptide.

Figure 7:
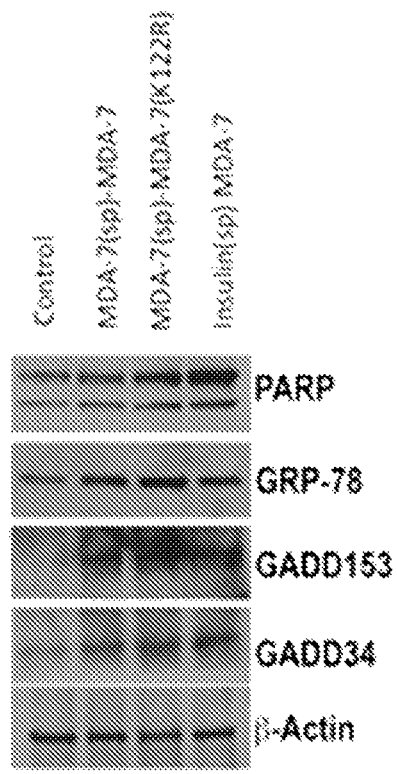
FIG. 7 shows example images illustrating cell signaling markers assessed from the lysates of HeLa cells transfected with the indicated construct.
Figure 8:
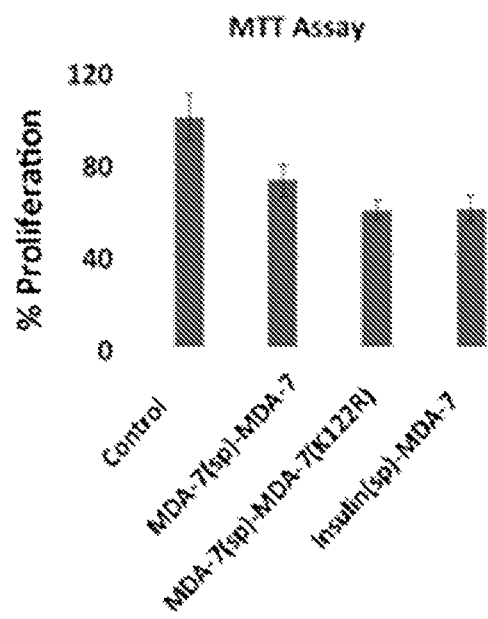
FIG. 8 shows example results for MTT assay following treatment of HeLa cells with conditioned media from Hela cells transfected with the indicated construct.
Figure 9:
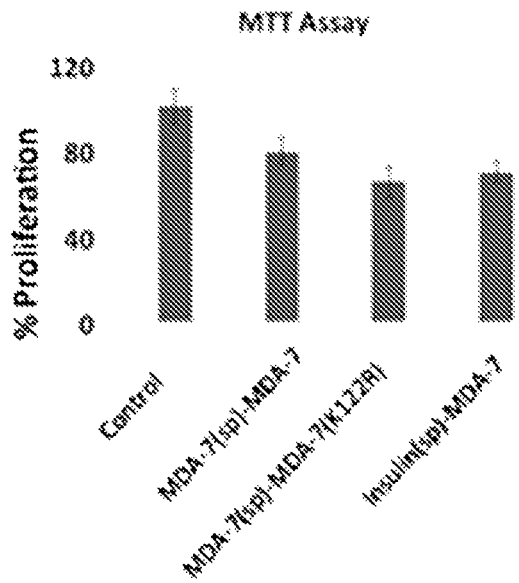
FIG. 9 shows example results for MTT assay following treatment of DU145 cells with conditioned media from HeLa cells transfected with the indicated construct.

Next, lysine 122 of MDA-7/IL-24 was converted to arginine by site directed mutagenesis using forward primer (5'-caactgttctattgtggtagtttctgaaaacagttttcaagtagaac-3') (SEQ ID NO: 19) and reverse primer (5'-gttctacttgaaaactgttttcagaaactaccacaatagaacagttg-3') (SEQ ID NO: 20). This construct (MDA-7(sp)-MDA-7(K122R) was transfected into HeLa cells and an increase in protein in the conditioned media (FIG. 5) and cell lysate (FIG. 6) by Western blotting was observed. Various cell signaling markers (PARP, GRP-78, GADD153, and GADD34) were also measured using the cell lysate and the results are shown in FIG. 7. The conditioned media from transfected Hela cells was added to HeLa cells and DU-145 cells, and MTT assays were performed. The MTT assay is a colorimetric assay that may be utilized to assess cell metabolic activity. NAD(P) H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. As shown in FIG. 8, HeLa cells treated with conditioned media from HeLa cells transfected with Insulin(sp)-MDA-7 and MDA-7 containing K122R showed a decrease in proliferation as compared to Hela cells treated with control conditioned media. Similarly, DU-145 cells treated with conditioned media from HeLa cells transfected with Insulin (sp)-MDA-7 and MDA-7 containing K122R showed a decrease in proliferation as compared to DU-145 cells treated with control conditioned media (FIG. 9).

Figure 10:
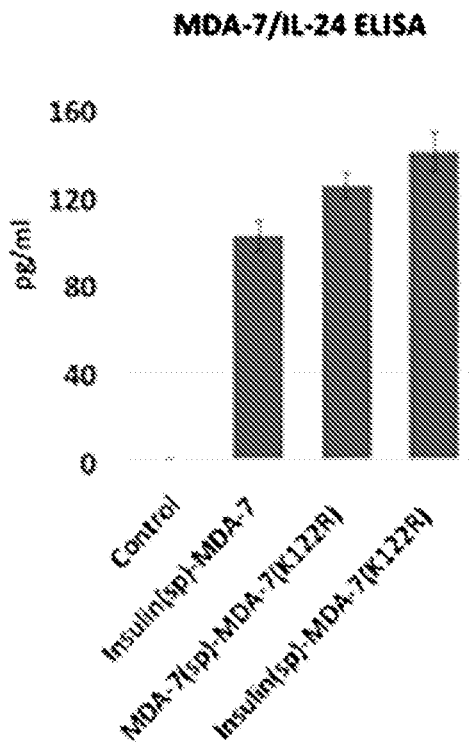
FIG. 10 shows example results for MDA-7/IL-24 protein expression determined by ELISA in the conditioned media of DU145 cells transfected with the indicated construct.
Figure 11:
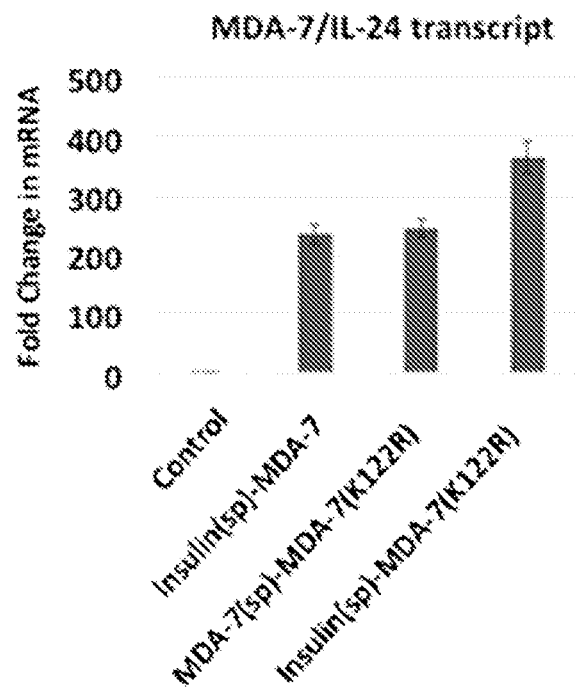
FIG. 11 shows example results for MDA-7/IL-24 expression assessed at the transcript level in DU145 cells after transfection with the indicated plasmids.
Figure 12:
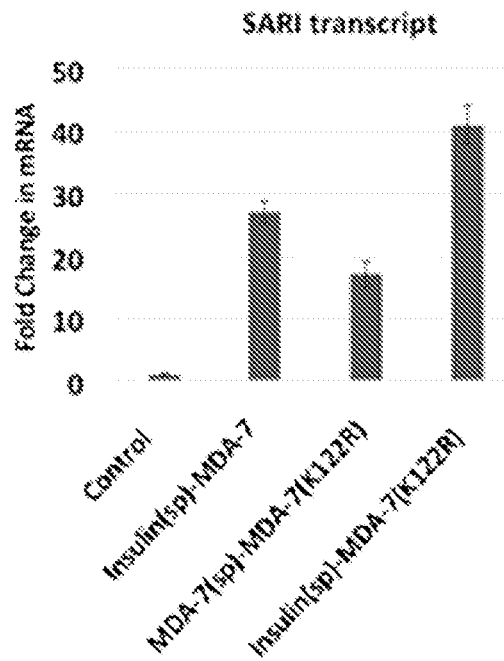
FIG. 12 shows example results for SARI expression assessed at the transcript level in DU145 cells after transfection with the indicated plasmids.
Figure 13:
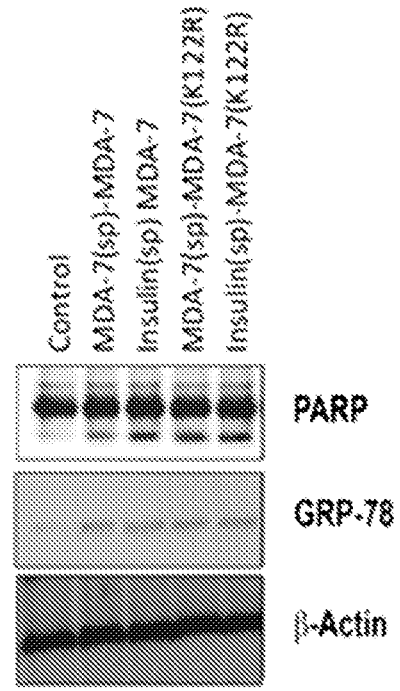
FIG. 13 shows example images illustrating PARP cleavage and GRP78 expression assessed in DU145 cells after transfection with indicated plasmids.
Figure 14:
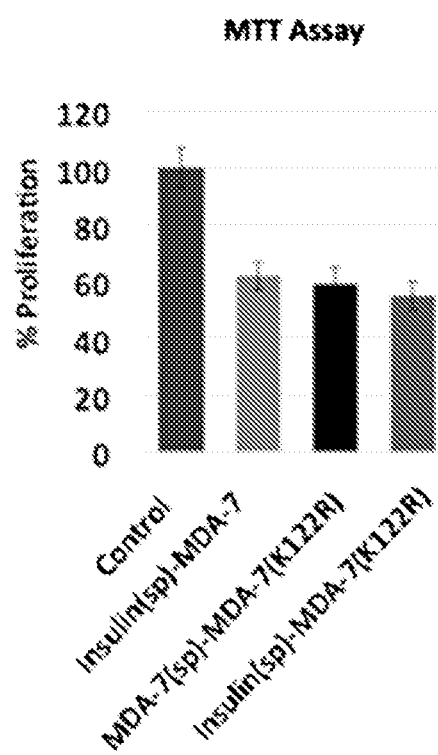
FIG. 14 shows example results for MTT assay following transfection of HeLa cells with the indicated constructs.

Having an MDA-7/IL-24 construct with enhanced protein secretion as well as enhanced protein stability may be very valuable as a potential gene therapeutic for cancer. Accordingly, lysine 122 was mutated to arginine in the Insulin(sp)-MDA-7 construct using site-directed mutagenesis. This construct was transfected in DU-145 cells and results showed enhanced MDA-7/IL-24 expression in the conditioned media using ELISA (FIG. 10) and at the transcript level using RTQ-PCR (FIG. 11). Expression of a downstream target of MDA-7/IL-24, SARI, was assessed at the transcript level, and Insulin(sp)-MDA-7(K122R) showed the highest SARI induction compared to Insulin(sp)-MDA-7 or single MDA-7/IL-24 modification (MDA-7 containing K122R) (FIG. 12). PARP cleavage and the expression of GRP-78 were also assessed in DU-145 cells following transfection with MDA-7(sp)-MDA-7 (wild type MDA-7 signal peptide), Insulin(sp)-MDA-7, MDA-7(sp)-MDA-7(K122R) and Insulin(sp)-MDA-7(K122R) (FIG. 13). Results of the MTT assays showed a decrease in proliferation following transfection of HeLa cells with the constructs Insulin(sp)-MDA-7, MDA-7(sp)-MDA-7(K122R), and Insulin(sp)-MDA-7 (K122R) (FIG. 14).

These experiments generated a recombinant protein through genetic engineering/cloning technology that links the insulin signal peptide to the MDA-7/IL-24 cDNA, thereby resulting in the coding of a functional protein displaying enhanced protein secretion. Additionally, a single amino acid mutation was introduced (lysine to arginine in at position 122) that enhanced protein stability. The combination of insulin with the mutated amino acid residue results in a novel version of MDA-7/IL-24 that is highly potent (enhanced secretion and stability) as compared to wild type MDA-7/IL-24.

Example 2: Engineered Interleukin with Selective Anti-Cancer Activity

Figure 15:
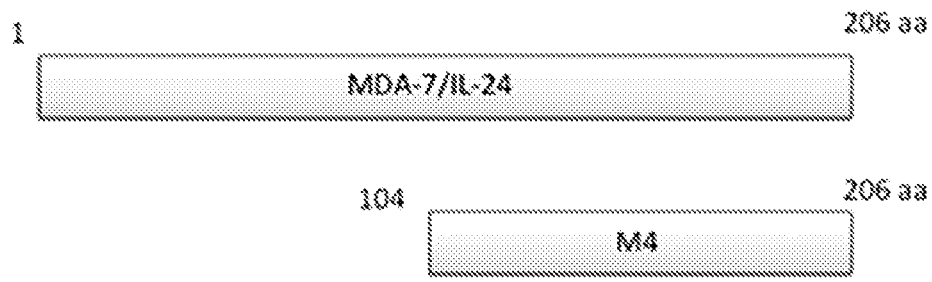
FIG. 15 shows a schematic illustration of full length MDA-7 and M4 (not drawn to scale).

M4 is a deletion mutant of full-length MDA-7/IL-24 protein with similar tumor inhibitory properties and mechanism of action as the full-length protein when administered internally using a virus or a GST-M4 fusion protein. A schematic illustration of M4 and MDA-7/IL-24 is shown in FIG. 15.

Experiments were conducted to determine if M4, like MDA-7/IL-24, could function as a secreted protein and induce "bystander" anti-cancer activity (anti-cancer activity against cancer cells distant from transfected cells). A secretory peptide was added to this mutant construct. A Flt-3(sp)-M4, which contains a Flt-3 signal peptide linked to M4, was created. Surprisingly, Flt-3(sp)-M4 had similar "bystander" anti-cancer effects as MDA-7/IL-24 protein, which were dependent on the presence of canonical IL-20R/IL-20R2, IL-22R/IL-20R2 and IL-20R1/IL-22R1 cell surface receptors.

Figure 16:
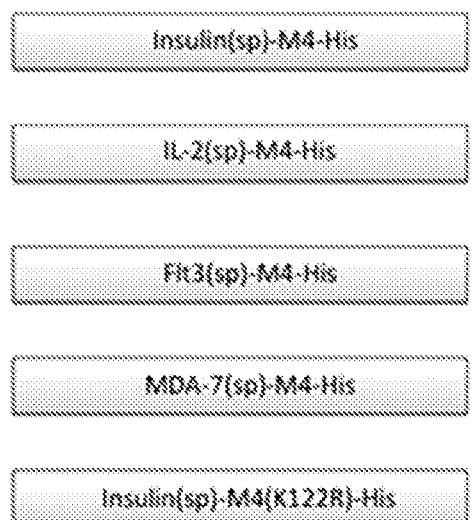
FIG. 16 shows a schematic illustration of example M4 modifications (not drawn to scale).
Figure 17:
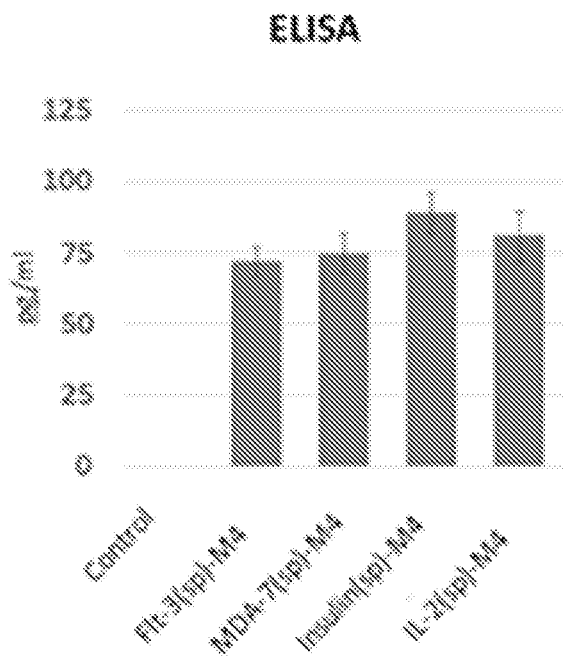
FIG. 17 shows example results for M4 expression assessed from the conditioned media of DU145 cells after transfection with the indicated plasmids using ELISA.
Figure 18:
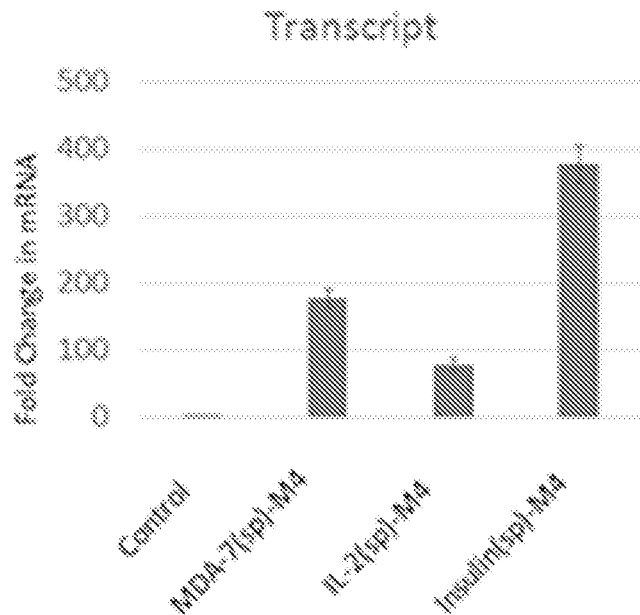
FIG. 18 shows example results for M4 expression assessed at the transcript level in DU145 cells after transfection with the indicated plasmids.

Based on these results, experiments were conducted to enhance M4 secretion and stability, and thereby potentially enhance anti-cancer activity. To determine if different sequence motifs could enhance the secretion of M4 over Flt-3(sp)-M4, three additional signal peptides linked to M4 were introduced and protein secretion was assessed. The four signal peptides tested were endogenous human MDA-7/IL-24, human IL-2, human Insulin, and Flt-3 signal peptides. The constructs were designated MDA-7(sp)-M4 (wildtype MDA-7/IL-24 secretory peptide), IL-2(sp)-M4, Insulin(sp)-M4, and Flt-3(sp)-M4, respectively, and a schematic illustration is shown in FIG. 16. Each of these constructs also included a Histidine-tag. These constructs were transfected into DU-145 cells and assessed for expression of M4 in the conditioned media (FIG. 17) and at the transcript level (FIG. 18). An MDA-7/IL-24 antibody and RT-Q-PCR primers able to detect M4 were used to assess M4 expression.

Figure 19:
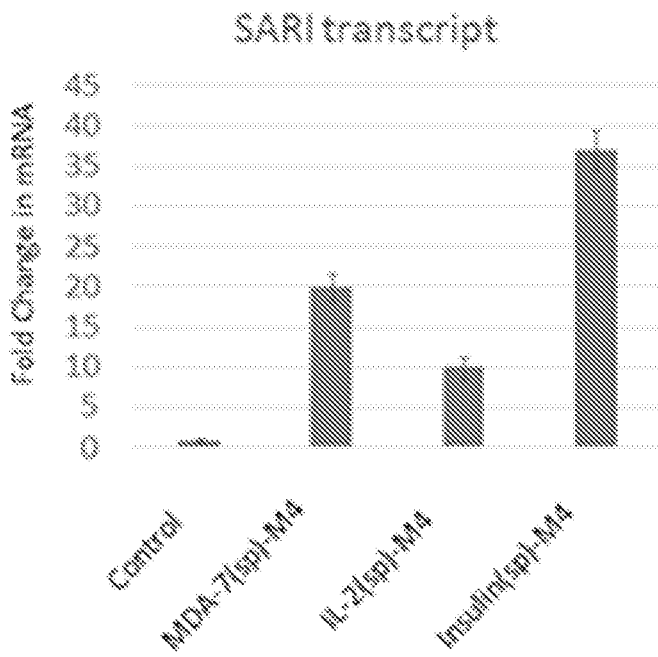
FIG. 19 shows example results for SARI expression was assessed at the transcript level in DU145 cells after transfection with indicated plasmids.
Figure 20:
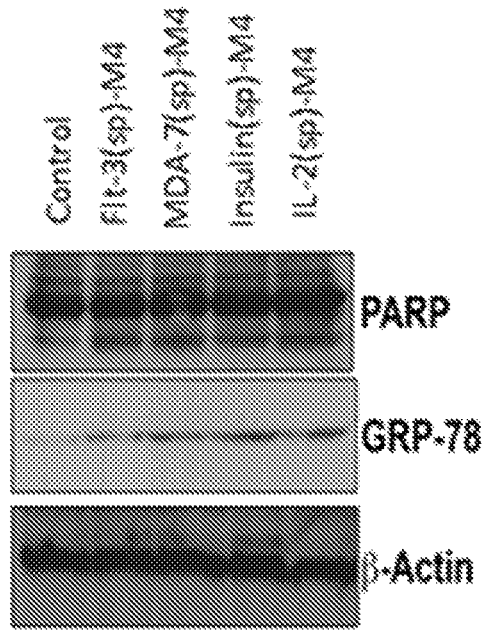
FIG. 20 shows example images illustrating PARP cleavage and GRP78 expression assessed in DU145 cells after transfection with the indicated plasmids.
Figure 21:
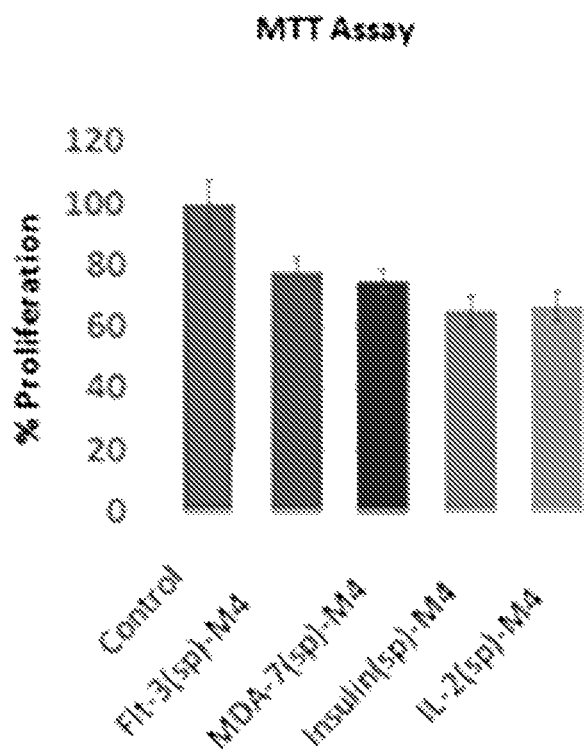
FIG. 21 shows example results for MTT assay following transfection of HeLa cells with the indicated constructs.

To ensure enhanced MDA-7/IL-24 secretion resulted in enhanced downstream signaling, the expression of a downstream target of MDA-7/IL-24, the Suppressor of AP-1 regulated by interferon protein (SARI), was assessed. The highest SARI expression was observed in Insulin(sp)-M4 and results are shown in FIG. 19. PARP cleavage and the expression of GRP-78 were also evaluated in DU-145 cells following transfection with these four constructs, the results for which are shown in FIG. 20. MTT assays provided evidence of growth suppression by Insulin(sp)-M4 as shown in FIG. 21. Taken together, these results demonstrated that the insulin signal peptide enhanced M4 protein secretion to a greater extent when compared to the other 3 signal peptides.

Figure 22:
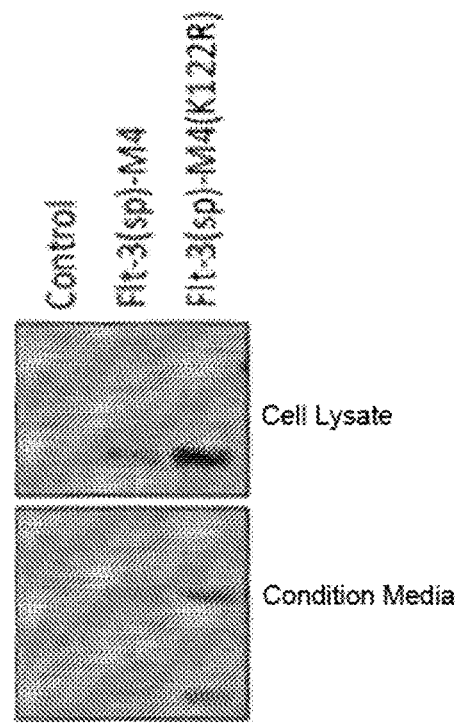
FIG. 22 shows example images illustrating M4 expression from the lysate and conditioned media of DU145 cells transfected with the indicated construct.
Figure 23:
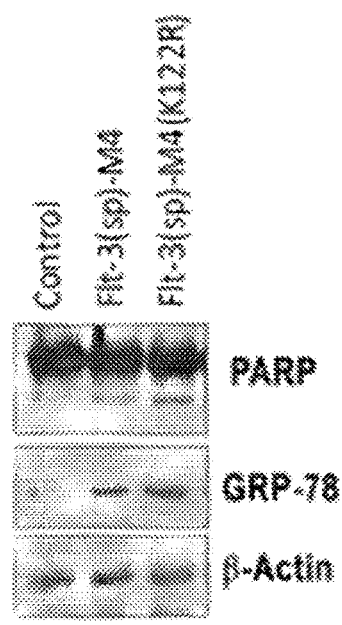
FIG. 23 shows example images illustrating PARP cleavage and GRP78 expression assessed in DU145 cells after transfection with the indicated plasmids.
Figure 24:
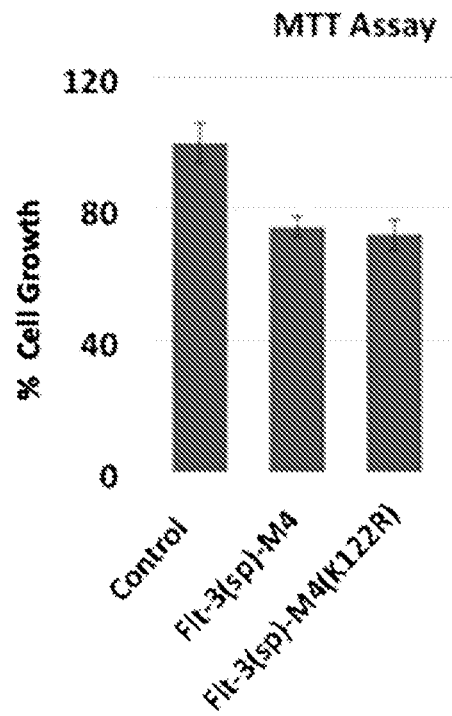
FIG. 24 shows example results for MTT assay following treatment of Du145 cells with conditioned media from IM-PHFA cells transfected with the indicated constructs.

As noted in Example 1, improvements were obtained by mutating lysine at position 122 to arginine in full-length MDA-7/IL-24. The corresponding lysine was identified in M4 and mutated to arginine using site directed mutagenesis using forward primer (5'-caactgttctattgtggtagtttct-gaaaacagttttcaagtagaac-3') (SEQ ID NO: 19) and reverse primer (5'-gttctacttgaaaactgttttcagaaactaccacaatagaacagttg-3') (SEQ ID NO: 20). Next, Flt-3(sp)-M4 and Flt-3(sp)-M4 (K122R) were transfected into DU-145 cells. An increase in protein in both the conditioned media and cell lysates was observed (FIG. 22). PARP cleavage and the expression of GRP-78 were also assessed in these DU-145 cells and the results shown in FIG. 23. The conditioned media from transfected IM-PHFA (immortalized primary human fetal astrocytes) cells was added to DU-145 cells and MTT assays were performed (FIG. 24). The results show cell growth suppression by conditioned media from cells transfected with either Flt-3(sp)-M4 or Flt-3(sp)-M4(K122R) compared to the control.

These experiments generated a genetically engineered chimera of MDA-7/IL-24 that links insulin signal peptide to M4 resulting in a protein with enhanced secretion and tumor suppressive capabilities similar to full length MDA-7/IL-24 in human cancers. Additionally, a single amino acid mutation (corresponding to a mutation of lysine to arginine at position 122 of full length MDA-7/IL-24) enhanced protein stability.

Example 3: Treatment and Monitoring of Metastatic Prostate Cancer Using Genetically Engineered Interleukin The next generation MDA-7/IL-24 protein, referred to as "NG.MDA-7/IL-24" or "NG.m7," displayed increased secretion and stability while retaining properties of the original molecule. NG.MDA-7/IL-24 features the insulin signal peptide fused to the K122R mutation variant of MDA-7/IL-24 (Insulin(sp)-MDA-7(K122R)).

Figure 25A:
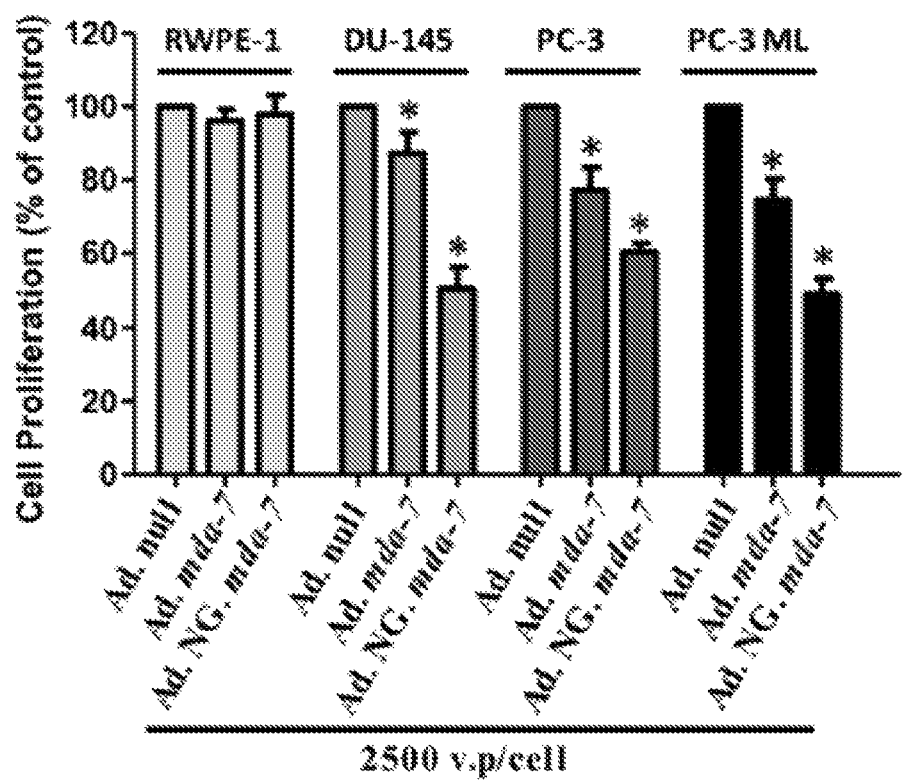
FIGS. 25A-25B show example results illustrating that adenovirus encoding MDA-7/IL-24 with a K122R mutation (designated "Ad.NG.mda-7/IL-24") suppresses proliferation of CaP cells more robustly than adenovirus encoding wild-type MDA-7/IL-24 (designated "Ad.mda-7/IL-24"). Human CaP cells (DU-145, PC3 and PC-3ML) and immortal primary prostate epithelial cells were infected with adenoviruses expressing either mda-7/IL-24 or NG.mda-7/IL-24 at an MOI of 2,500 VP. After 72-hr, cell proliferation (FIG. 25A) and apoptosis (FIG. 25B) were determined by MTT and Flow cytometry, respectively. *: Statistical significance ($p<0.05$).
Figure 25B:
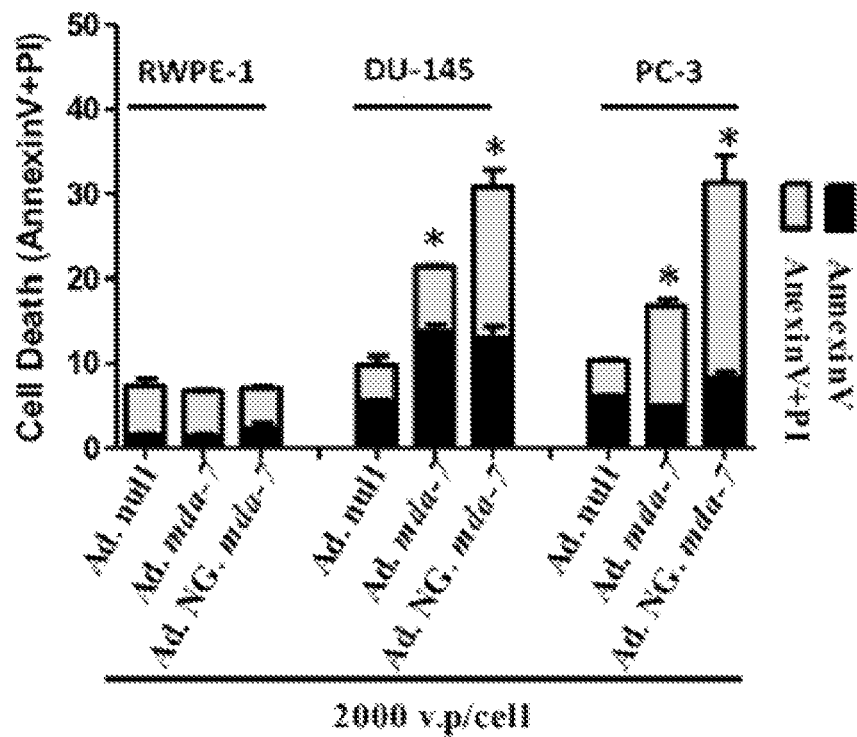

To test whether NG.MDA-7/IL-24 displayed greater antitumor activity against prostate cancer (abbreviated CaP) than native MDA-7/IL-24, a non-replicating adenovirus Type 5 vector in which NG.mda-7/IL-24 is under the transcriptional control of a CMV promoter (Ad.NG.mda-7/IL-24) was developed. Three prostate cancer cell lines (DU-145, PC3, PC3ML) and immortal primary human prostate epithelial (RWPE-1) cells were infected with adenoviral vectors carrying wild type mda-7/IL-24 gene or NG.mda-7/IL-24. The effects on cell growth (MTT assays) were evaluated and the results shown in FIG. 25A. Expression of both versions of MDA-7/IL-24 inhibited growth of the prostate cancer cell lines (p<0.05 vs. control) without showing any detrimental effects on normal immortal human prostate epithelial cells. Quantitatively, NG.mda-7/IL-24 caused significantly higher growth inhibition and cell killing effects in human cancer cells. Results indicated Ad.NG.mda-7/IL-24 mediated killing was a result of apoptosis (FIG. 25B). Infection of prostate cancer cells with Ad.NG.mda-7/IL-24 resulted in a significantly higher level of secreted protein in culture media in comparison with wild type Ad.mda-7/IL-24. These results demonstrated that NG.MDA-7/IL-24 has selective anti-cancer activity in human prostate cancer cells.

Targeting Mcl-1 Inhibition to Enhance NG.mda-7/IL-24 Therapy.

Figure 26A:
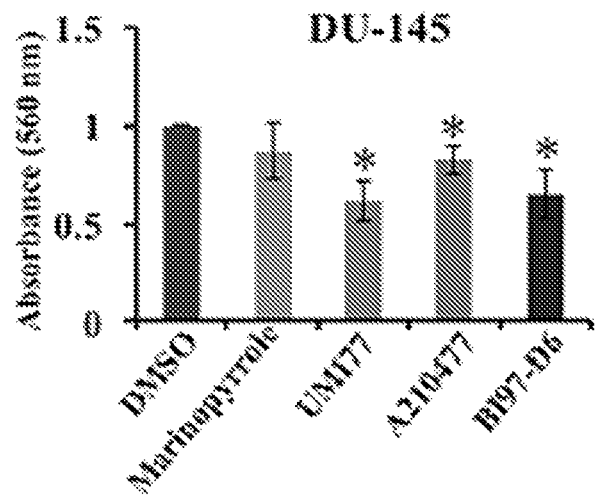
FIGS. 26A-26E show example results illustrating that MDA-7/IL-24 and a targeted Mcl-1 inhibitor synergistically inhibit the proliferation of human and mouse CaP cells. Human (DU-145) CaP cells were treated with different targeted small molecules alone (FIG. 26A) or in combination with MDA-7/IL-24 (FIG. 26B), and after 48 hrs cell growth was measured by MTT. * indicates statistical significance vs. respective control group. Immortalized primary normal human prostate epithelial cells, RWPE-1, were treated with different combinations as indicated and MTT assays were performed at 48 hrs (FIG. 26C). Murine (RMI-BM) CaP cells were treated with different targeted small molecules alone (FIG. 26D) or in combination with MDA-7/IL-24 (FIG. 26E), and after 48 hrs. cell growth was measured by MTT.
Figure 26B:
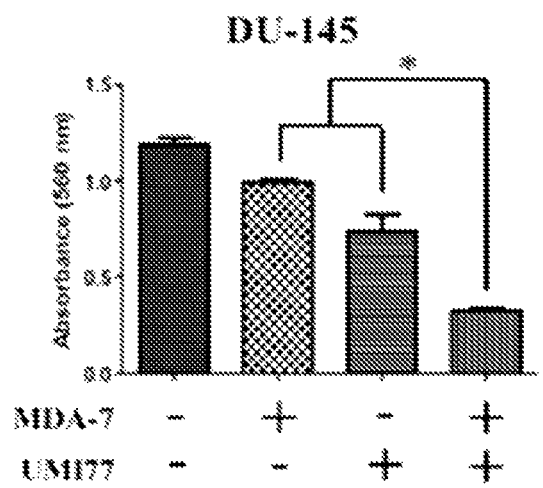
Figure 26C:
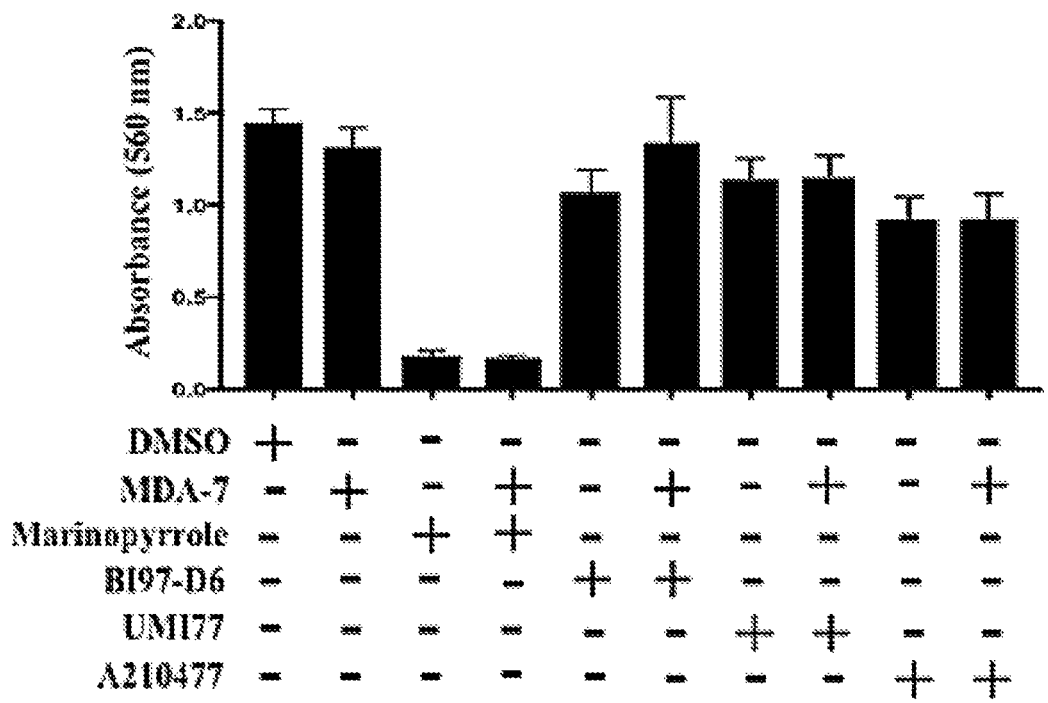
Figure 26D:
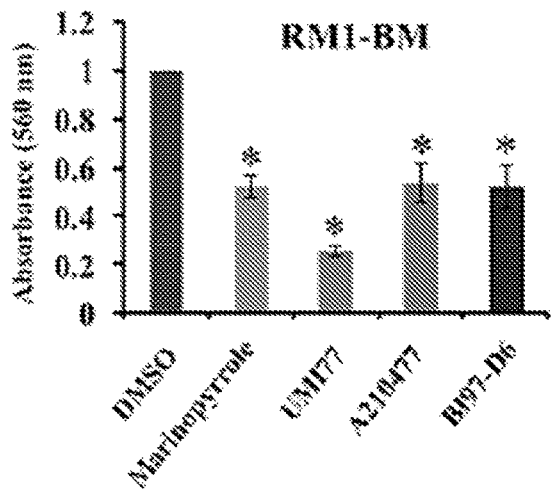
Figure 26E:
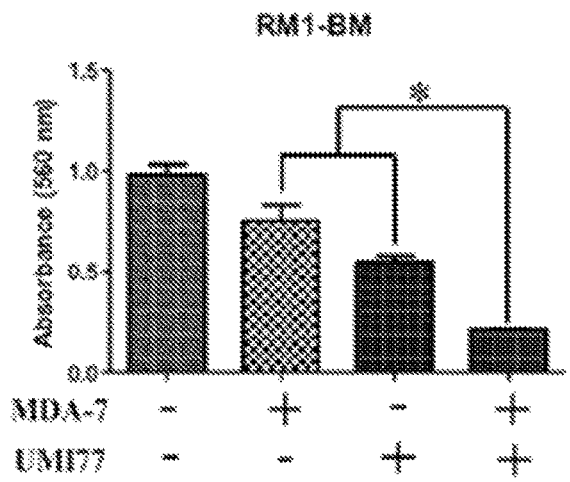

To test a multi-target approach for treatment of prostate cancer bone metastases, experiments were conducted to target Mcl-1 inhibition and investigate the effects on NG-mda-7/IL-24 efficacy. Using NMR (nuclear magnetic resonance) and computational biology, two Mcl-1 inhibitors were identified (Sabutoclax and BI-97D6) and their activity was validated in immune competent mice in combination with MDA-7/IL-24. In addition to these inhibitors, three commercially available targeted inhibitors were evaluated to determine potential synergistic effects with MDA-7/IL-24. The three inhibitors were UMI-77 (showing selectivity to Mcl-1 over other members of the Bcl-2 family), Marinopyrrole A (selective inhibitor of Mcl-1), and A-1210477. In an MTT assay, all of these inhibitors significantly inhibited proliferation of human (DU-145) and murine (RM1-BM) prostate cancer cells (FIGS. 26A and 26D, respectively). Mcl-1 expression was elevated by 1.7-fold in RM1-BM (RM1-BM cells selected for enhanced metastasis to bone) as compared to RM1 cells, indicating functional relevance of Mcl-1 in this metastatic process. As observed with Sabutoclax and BI-97D6, antitumor synergy was evident when combined with MDA-7/IL-24 (FIGS. 26B and 26E for DU-145 and RM1-BM, respectively). Except for Marinopyrrole, no anti-proliferative effects were observed with the other Mcl-1 inhibitors, either alone or in combination with MDA-7/IL-24, in MTT assays using RWPE-1 cells (FIG. 26C). This further supported the cancer-specificity of specific Mcl-1 inhibitors. Next, the therapeutic effect of MDA-7/IL-24 protein in combination with BI-97D6 was tested, in male athymic nude mice injected by the intracardiac route with human prostate cancer PC3-ML cells, resulting in bone metastases. While a significant level of bone metastases was evident in the control group, treatment with MDA-7/IL-24 or BI-97D6 alone resulted in a statistically significant inhibition of bone metastases.

Evaluation of "Bystander" Effects of MDA-7/IL-24 in Hi-Myc Mice

Figure 27A:
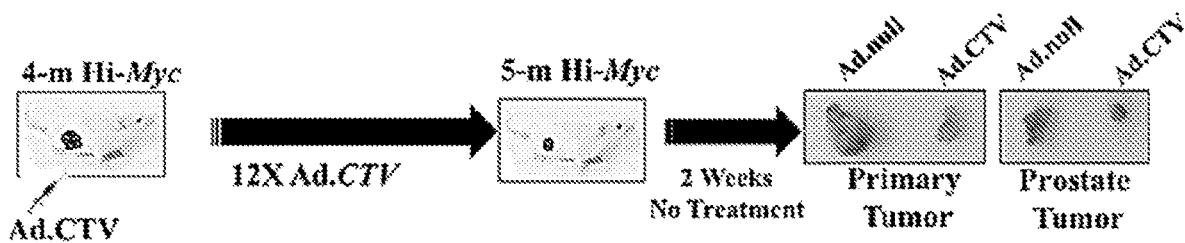
FIGS. 27A-27B show example experimental models and results illustrating that MDA-7/IL-24 treatment reduces both local (injected) and distant (non-injected) CaP tumor development in Hi-Myc mice.
Figure 27B:
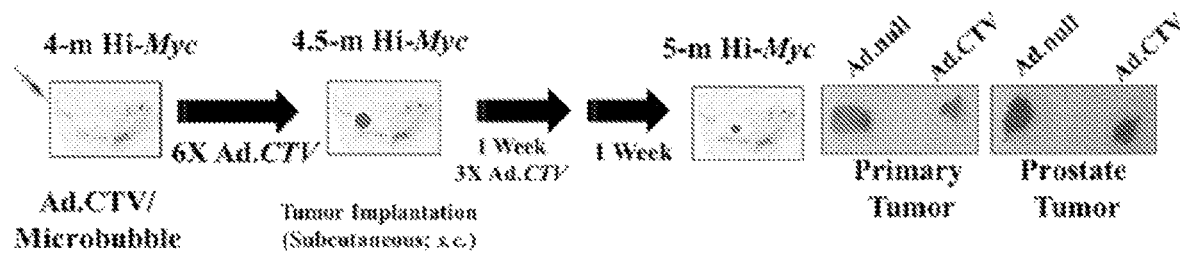

Among the many attributes of MDA-7/IL-24 as a potential cancer therapeutic is its ability to induce "bystander" tumor killing by initiating an autocrine/paracrine loop in both normal and cancer cells. To evaluate the potential "bystander" antitumor effect in the Hi-Myc model, two sets of experiments were performed. The schematic diagrams are presented in FIGS. 27A-B. First, a subcutaneous xenograft (mu-PDX established from a Hi-Myc mouse prostate tumor; mu-PDX Hi-Myc) was established in 4-month old Hi-Myc mice and the tumors were treated with Ad.null (adenovirus null vector) or Ad.CTV (adenovirus vector—Cancer Terminator Virus, expressing the viral replication gene E1A and therapeutic gene mda-7/IL-24 under the control of cancer-specific promoter PEG-3 and a ubiquitous CMV promoter, respectively) for 4 weeks (3 doses per week, total 12 injections). When compared on the 6 h week after mu-PDX Hi-Myc xenograft implantation, a significant reduction of both the primary subcutaneous xenograft (mu-PDX Hi-Myc) and the endogenous transgenic prostate tumor in the prostate gland were observed in mice receiving Ad.CTV (FIG. 27A). In the second experiment, 4-month old Hi-Myc mice were treated with Ad.CTV-m7 through tail vein (as a complex with microbubbles and ultrasound referred to as the UTMD (ultrasound-targeted microbubble-destruction) approach) and after six (6) doses within the first two weeks, mice were challenged with mu-PDX Hi-Myc cells by subcutaneous injection. Treatment continued for an additional one week (3 injections) and the following week mice were euthanized. As observed with the first protocol (direct intra-tumoral injection of subcutaneous mu-PDX tumor cells), a significant reduction of the subcutaneous mu-PDX Hi-Myc and endogenous transgenic prostate tumor was evident in the Ad.CTV-m7 group (FIG. 27B).

These two experiments demonstrated MDA-7/IL-24 treatment reduced both local (injected) and distant (non-injected) prostate cancer tumor development in Hi-Myc mice. This confirmed the "bystander" killing effect of MDA-7/IL-24, which, without being bound to theory, may be due to augmentation of immune system stimulation that negatively impacts tumor progression.

Example 4: Immunotherapy and Molecular Targeted Therapy

Figure 28A:
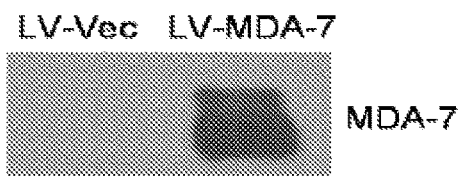
FIGS. 28A-28C shows examples results illustrating that engineering tumor-reactive T cells to produce MDA-7/IL-24 enhances elimination of CaP lung metastases.
Figure 28B:
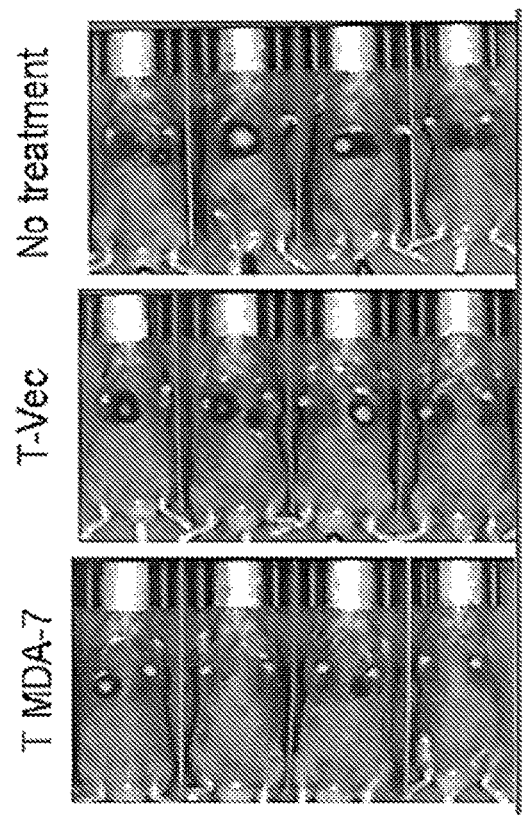
Figure 28C:
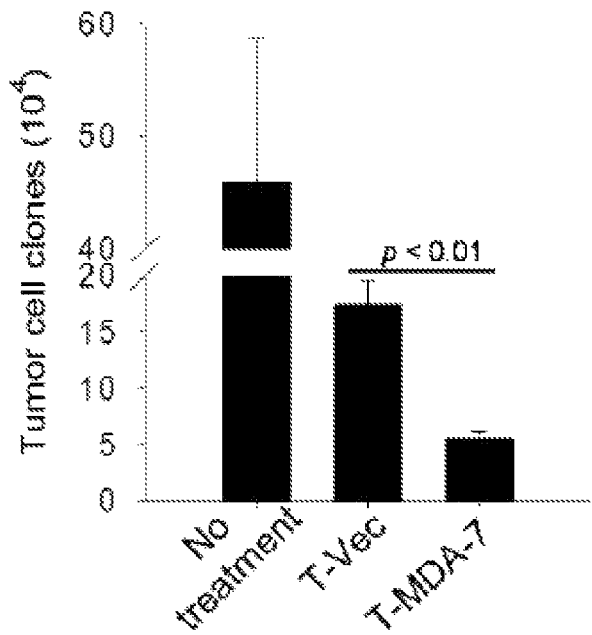

Experimental data shown in FIGS. 28A-C demonstrated that T cells genetically modified to express MDA-7/IL-24 were more effective than unmodified T cells in eradicating lung metastases of mouse prostate cancer. Tumor-sensitized T cells, derived from RMI prostate cancer bearing mice, were expanded by IL-7/IL-15 and infected with lentiviruses encoding MDA-7/IL-24 or empty vector. The level of MDA-7/IL-24 in the media was examined using immunoblotting and is shown in FIG. 28A. C57BL/6 mice with established RMI-Luc lung metastases were treated with or without MDA-7/IL-24-producing T cells. Pulmonary metastases were followed using a small animal imaging system (FIG. 28B) and quantified by clonogenic assays using lung tissues (FIG. 28C). The data supports the use of antigen and/or tumor-reactive T lymphocytes for adoptive T-cell therapy (ATT) to target MDA-7/IL-24 for selective delivery to the metastatic bone niche for potentially synergistic tumor eradication.

Figure 29:
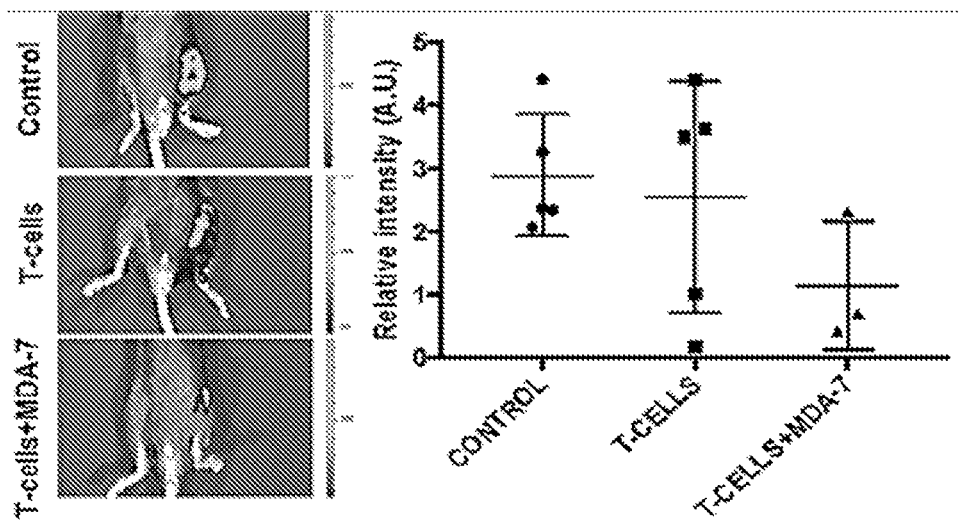
FIG. 29 shows example results illustrating that administration of recombinant MDA-7/IL-24 protein improves T cell therapy of CaP bone metastases. C57BL/6 mice established with experimental bone metastases via intratibial injection of ovalbumin-positive CaP RM1-Luc cells expressing luciferase were treated with OVA-specific T cells (OT-I) alone or in combination with recombinant MDA-7/IL-24 protein i.v. (5 mg/kg body weight, 3 times). Development of bone lesions was monitored by BLI. Luciferase intensity was quantified and is presented graphically.

The data in FIG. 29 showed that administration of recombinant MDA-7/IL-24 protein improved T cell therapy of prostate cancer bone metastases. While antigen-specific T cells only had a modest effect on prostate cancer bone metastases, systemic administration of recombinant MDA-7/IL-24 protein significantly enhanced the therapeutic potency of ATT, supporting strategic coupling of these two therapeutic agents. C57BL/6 mice established with experimental bone metastases via intra-tibial injection of ovalbumin-positive prostate cancer RMI-Luc cells expressing luciferase were treated with OVA-specific T cells (OT-I) alone or in combination with recombinant MDA-7/IL-24 protein intravenously (5 mg/kg body weight, 3 times). Development of bone lesions was monitored by bioluminescent imaging (BLI) (FIG. 29 left panel). Luciferase intensity was quantified and is presented graphically (FIG. 29 graph).

Figure 30:
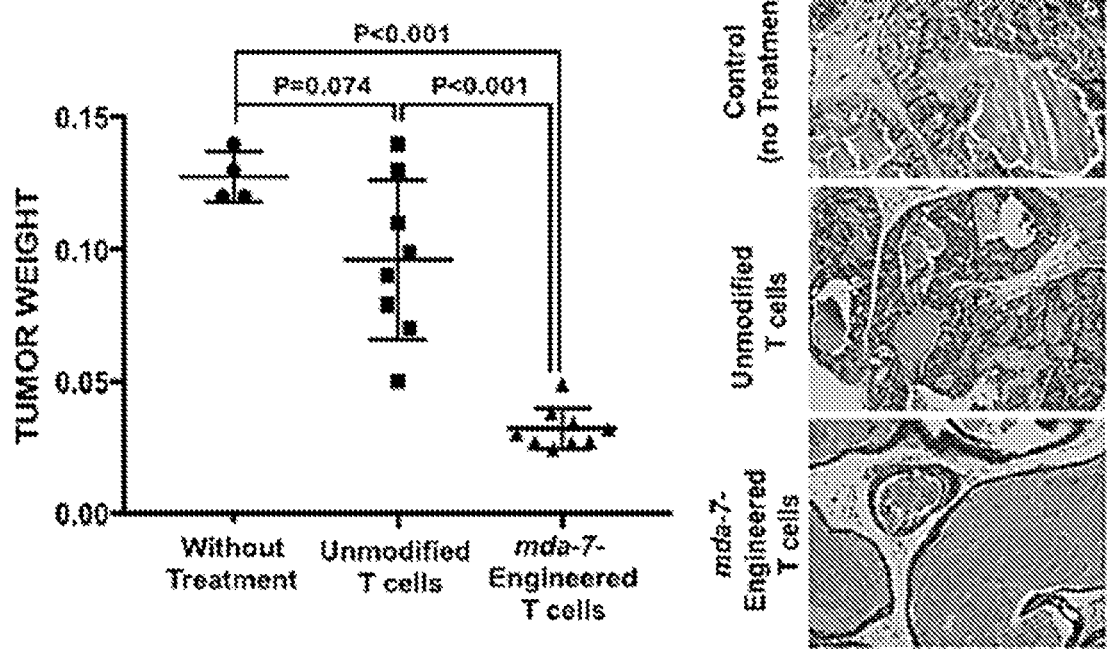
FIG. 30 shows example results illustrating therapeutic efficacy of mda-7/IL-24-engineered T cells against CaP in a transgenic model. Cohorts of Hi-Myc mice received tumor-reactive T cells infected with or without a lentivirus encoding mda-7/IL-24 (once a week, 4 maximum) i.v. Tumor burden, measured by weights of the prostates, was examined at 6-month of age and the average value (n=4) are presented. Each point in the graph represents tumor weight of an individual mouse (Left Panel). Representative H/E sections of prostate from each experimental group (Right panel).

To reduce possible risk of toxicity from systemic delivery of cytokines, targeted delivery of MDA-7/IL-24 using T cells as a vehicle was investigated. Tumor-reactive T lymphocytes from 6-month-old Hi-Myc transgenic mice that have developed prostate cancer were recovered and infected with a lentivirus encoding mda-7/IL-24. These engineered T cells were used to treat a cohort of Hi-Myc transgenic mice with established prostate cancer (4 months old), which resulted in a marked tumor suppression as shown in FIG. 30. Tumor burden, measured by weights of the prostates, was examined at 6-month of age and the average value (n=4) are presented (FIG. 30, left panel). Each point in the graph represents tumor weight of an individual mouse. Representative H/E sections of prostate from each experimental group (FIG. 30, Right panel). The results further demonstrated the therapeutic potency of MDA-7/IL-24-engineered T cell therapy.

Figure 31A:
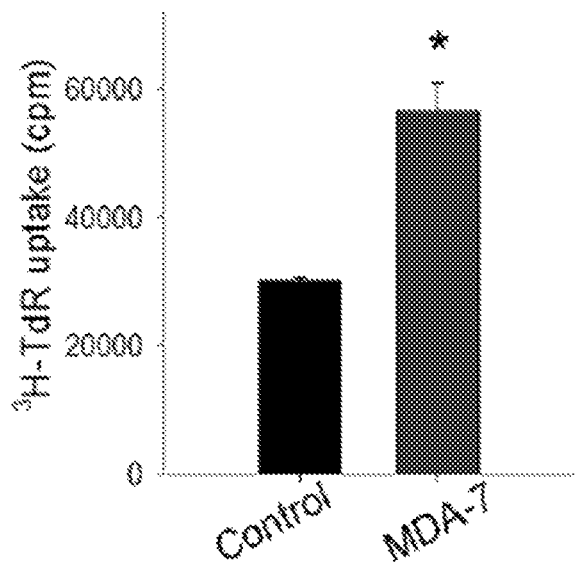
FIGS. 31A-31B show example results illustrating that MDA-7/IL-24 promotes T cell expansion and activation.
Figure 31B:
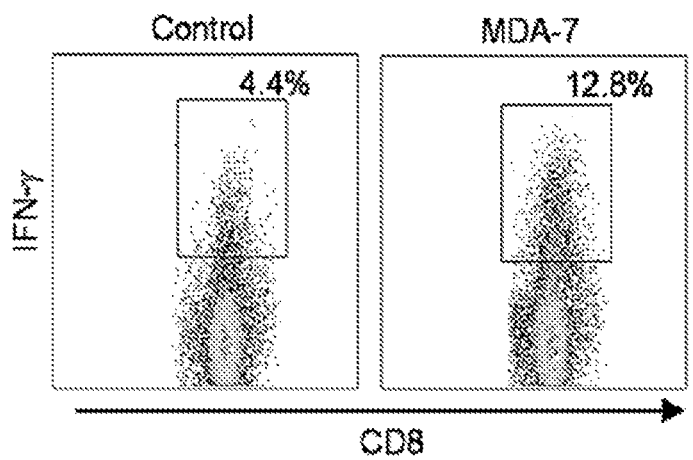

In subsequent experiments, $CD8^+$ T cells were stimulated with anti-CD3/CD28 antibodies in the presence or absence of purified MDA-7/IL-24 protein (20 ng/ml). Cell proliferation was measured using $^3$H-thymidine (TdR) incorporation assays. $p<0.05$. The data in FIG. 31A showed that delivering MDA-7/IL-24 significantly enhanced the proliferation of T cells upon T-cell receptor (TCR) ligation. Treatment of mice with recombinant MDA-7/IL-24 protein increased the frequency of IFN-γ-expressing $CD8^+$ T cells (FIG. 31B). C57BL/6 mice were injected intravenously with MDA-7/IL-24 protein (10 μg) or PBS; 48 hours later, lymph node cells were assessed for IFN-γ-producing $CD8^+$ T cells by intracellular staining. The data demonstrated that MDA-7/IL-24 promotes T cell expansion and activation, which supports a role of MDA-7/IL-24 as a pro-Th1 cytokine.

Figure 32A:
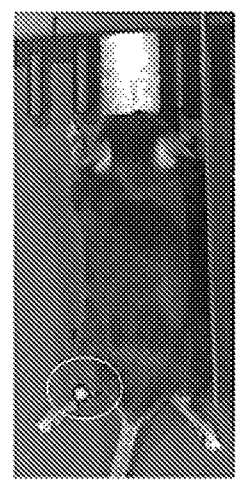
FIGS. 32A-32B show example results illustrating that CaP bone metastases enhances PD-1 expression on CD8+ T cells in the bone niche.
Figure 32B:
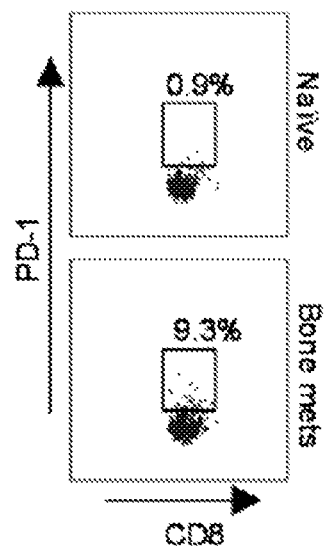

To understand the immune environment of prostate cancer bone metastatic niche, experiments were undertaken to analyze this specific niche. Bone metastases was established by intratibial injection of the RM1-Luc cells and followed by bioluminescence imaging analysis (FIG. 32A). $CD8^+$ cells in the bone marrow cavity from naïve mice or mice with established prostate cancer bone metastases were examined for PD-1 expression by FACS (FIG. 32B). These data demonstrate prostate cancer bone metastases enhances PD-1 expression on $CD8^+$ T cells in the bone niche. When analyzing T cells in the bone marrow niche, PD-1 expression was highly elevated on T cells from mice established with prostate cancer bone metastases following intratibial injections of prostate cancer cells compared to those in naïve mice, indicating immunosuppression exists in bone niche with metastases.

Figure 33:
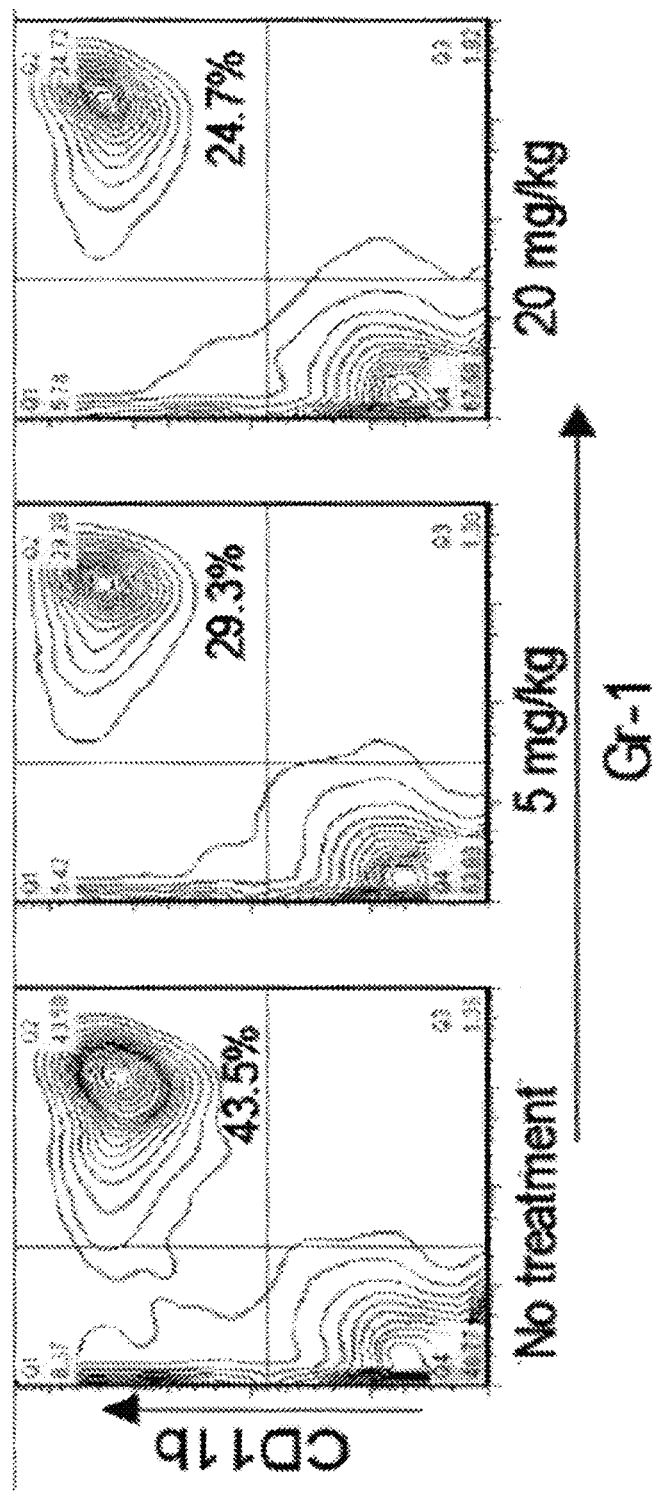
FIG. 33 shows example results illustrating potential immune modulation by Mcl-1 inhibition. Mcl-1 inhibitor reduces MDSCs in tumor-bearing mice. Tumor-bearing mice received BI-97C1 (Sabutoclax) (5 mg/kg or 20 mg/kg) i.p. or left untreated. 24 hrs. later, splenic CD11b+Gr-1+ MDSCs were assessed by FACS.

Immunosuppressive networks in the TME include recruitment and expansion of myeloid-derived suppressor cells (MDSCs). MDSCs mediate tumor-associated immunosuppression as well as non-immunological functions, e.g., angiogenesis, tumor invasion. To investigate pharmacologic targeting of MDSCs, tumor-bearing mice received the Mcl-1 inhibitor, BI-97C1 (Sabutoclax) (5 mg/kg or 20 mg/kg) intraperitoneally or were left untreated. Twenty-four (24) hours later, splenic $CD11b^+Gr-1^+$ MDSCs were assessed by FACS. As shown in FIG. 33, a single administration of a Mcl-1 inhibitor (BI-97C1; Sabutoclax) in tumor-bearing mice substantially reduced the frequency of $CD11b^+Gr-1^+$ MDSCs, without inducing toxicity. These results provide a rationale for using small molecule Mcl-1 inhibitors to promote or amplify T cell-mediated antitumor toxicity by potentially conditioning the bone metastatic environment and overcoming prostate cancer-induced immune defects.

Example 5: MDA-7/IL24 and Breast Cancer

Experiments were conducted to investigate MDA-7/IL-24 as a candidate therapy for breast cancer (abbreviated BCa). Cancer-Specific Oncolytic Adenovirus Expressing mda-7/IL-24 Eradicates Primary and Distant BCa Tumors.

Figure 34A:
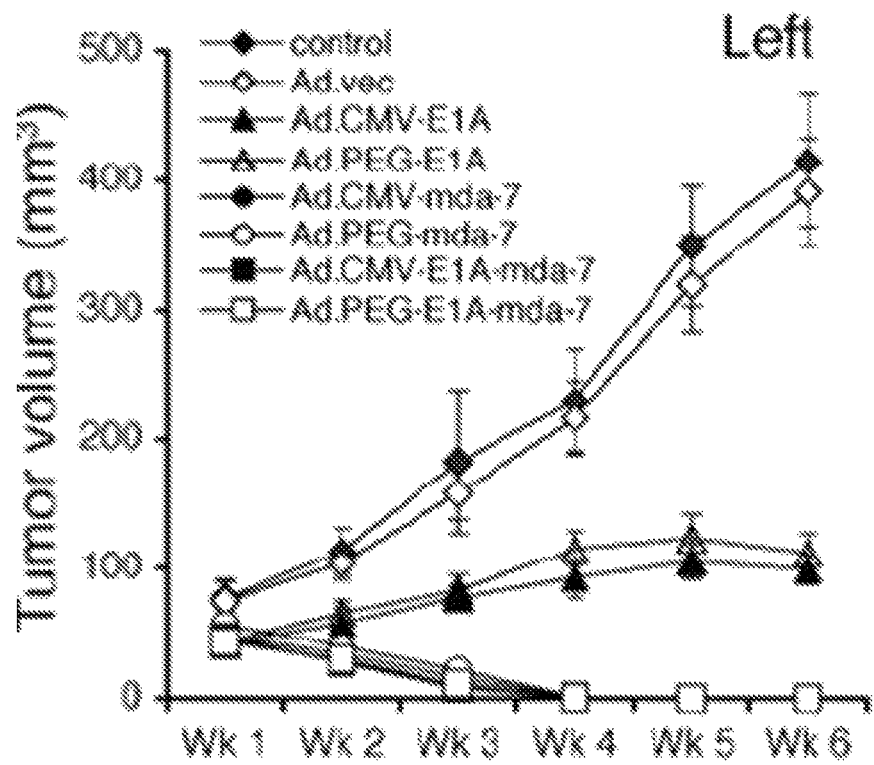
FIGS. 34A-34D show example results illustrating that cancer-specific oncolytic adenovirus (Ad) expressing mda-7/IL-24 eradicates primary and distant BCa tumors. Tumor xenografts from T47D cells were established in athymic nude mice in both the right and left flanks, and only tumors on the left side were injected with PBS (control) or with the indicated Ad for 3 weeks (total of seven injections).
Figure 34B:
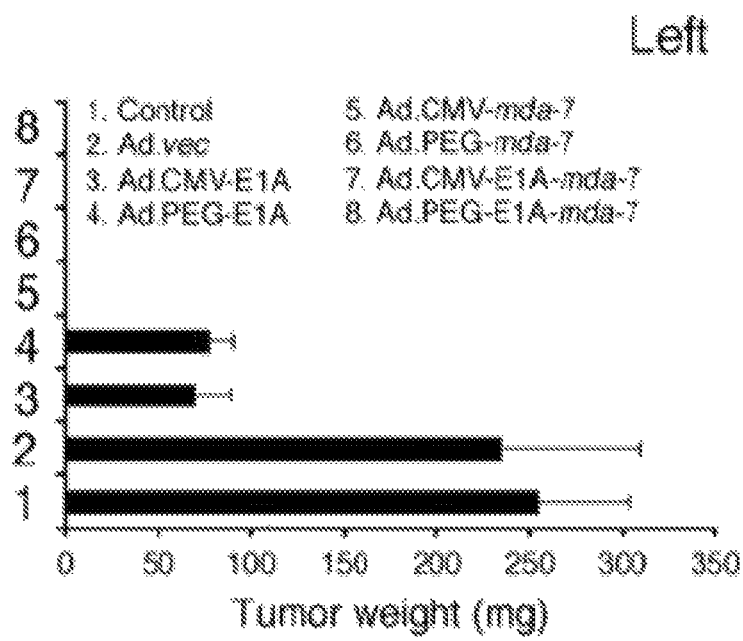
Figure 34C:
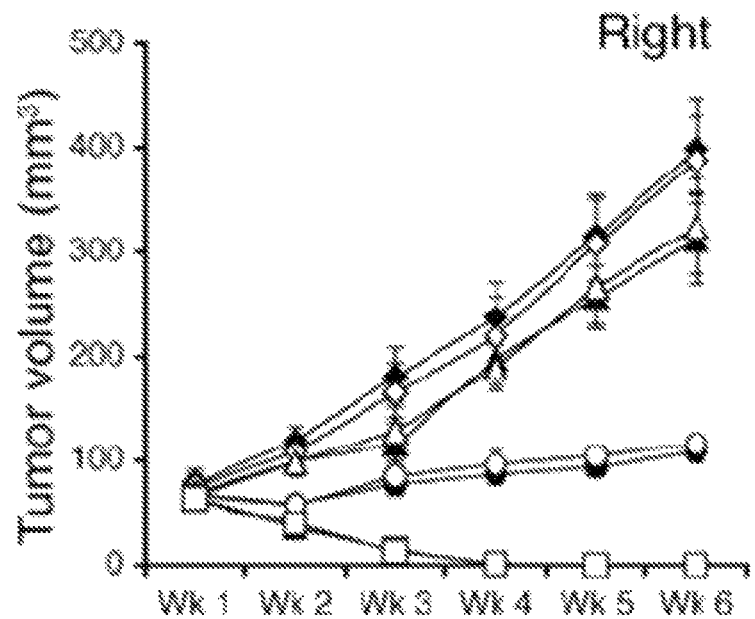
Figure 34D:
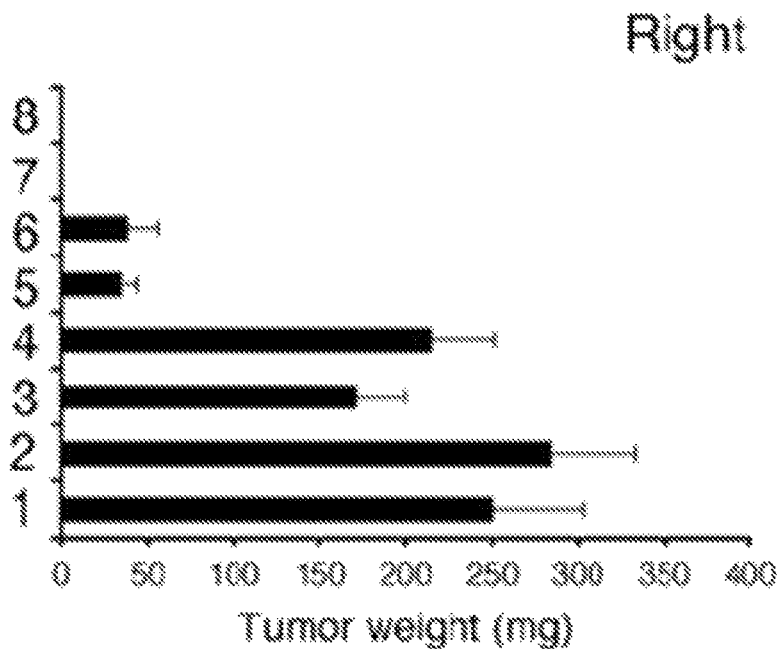

Ad.5-CTV-m7, a conditionally replication competent oncolytic adenovirus carrying mda-7/IL-24 efficiently reduced tumor burden in a breast cancer-derived xenograft model. An outcome of this experiment was that secreted MDA-7/IL-24, even from a non-replicating adenovirus vector, not only eradicated the primary tumor but also reduced growth in the contralateral tumor, indicating a marked 'bystander' antitumor effect (FIGS. 34A-D). Tumor xenografts from T47D cells (human breast cancer cell line) were established in athymic nude mice in both the right and left flanks, and only tumors on the left side were injected with PBS (control) or with the indicated adenovirus for 3 weeks (total of seven injections). Measurement of tumor volume is shown in FIGS. 34A and 34C. The data represent mean±SD with a minimum of five mice per group. Measurement of tumor weight at the end of the study is shown in FIGS. 34B and 34D. The data represent mean±SD with at least five mice per group. The data demonstrated that the Ad.5-CTV-m7 injected in tumor on one flank cured tumors on both flanks of these animals.

Adenoviral Mediated mda-7/IL-24 Expression Efficiently Decreases Mammary Tumor Burden in MMTV-PyMT Transgenic Mice.

Figure 35A:
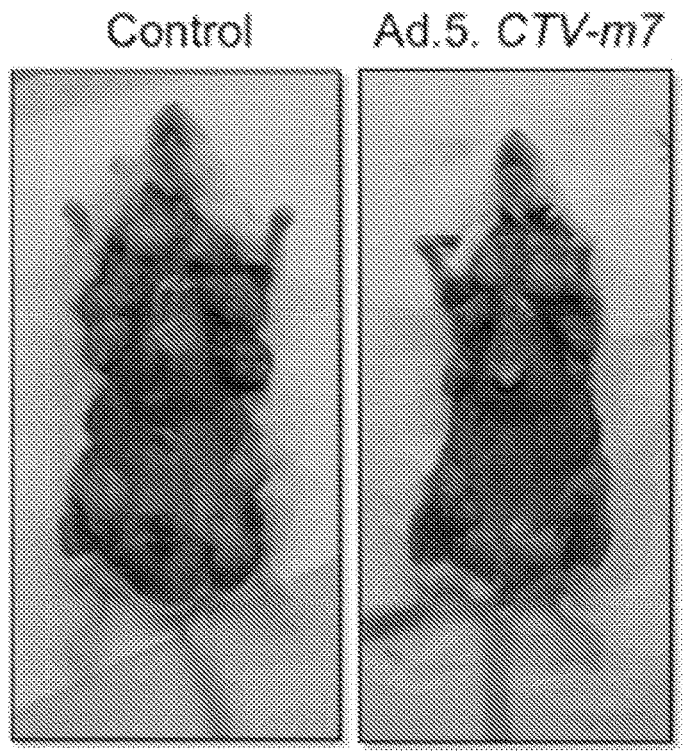
FIGS. 35A-35C provide example images and results showing that adenoviral mediated mda-7/IL-24 expression efficiently decreases mammary tumor burden in MMTV-PyMT transgenic mice.
Figure 35B:
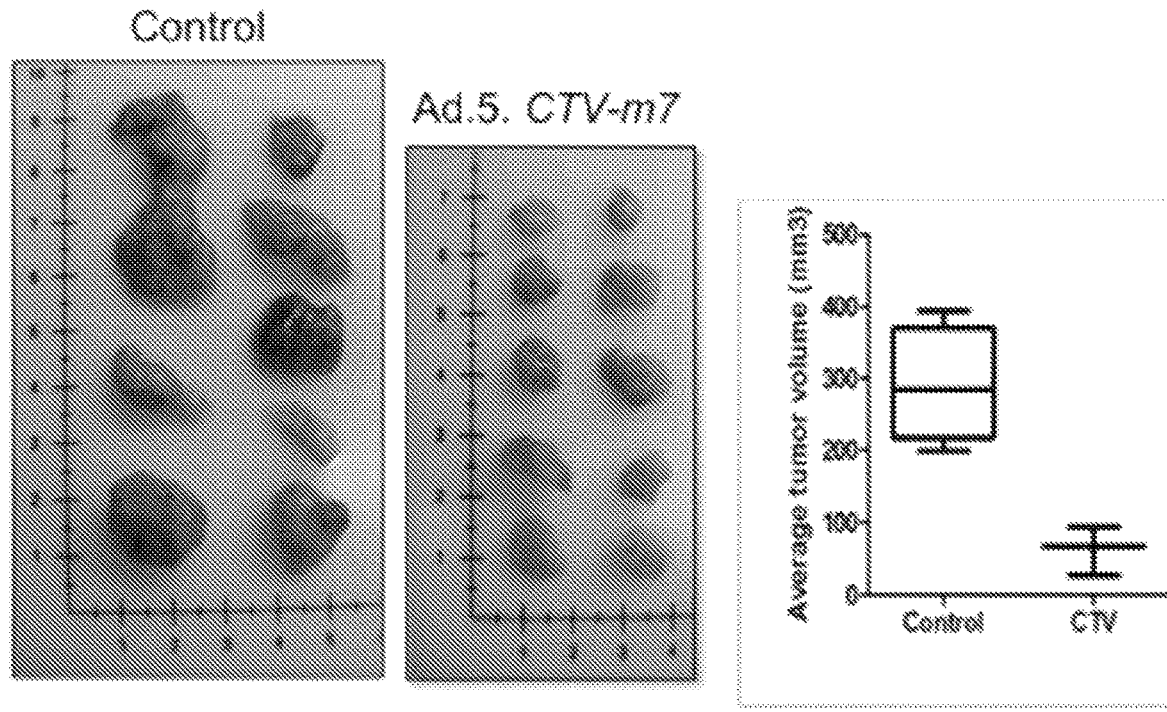
Figure 35C:
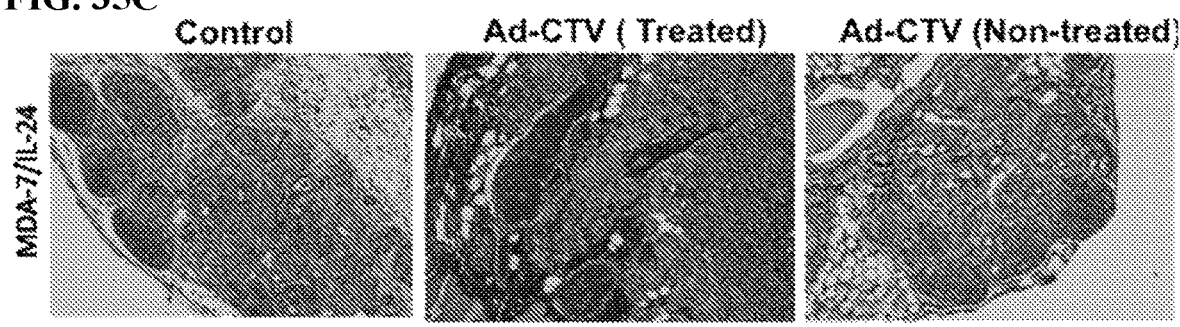

Ad.5-CTV-m7 was tested in the MMTV-driven polyomavirus middle T oncogene model (MMTV-PyMT). This transgenic strain develops multifocal mammary adenocarcinomas and metastatic lesions in the lymph nodes and lungs within 3-4 months, which are histologically similar to human breast cancer. Tumor-bearing mice upon receiving mda-7/IL-24 intratumorally showed a significant reduction in tumor volume as compared to control untreated mice (FIGS. 35A-C). Representative images of mice treated with or without Ad.5.CTV-m7 virus are shown in FIG. 35A. Fifty percent (50%) of palpable tumors that formed were injected with Ad.5.-CTV-m7. A maximum of 10 injections were administered per injected tumor (depending on when the tumors arose) over 4 weeks. FIG. 35B shows representative images of the resected tumors. The average tumor volumes are represented graphically. Immuno-histochemical staining of tumors was done to detect MDA-7/IL-24 expression and results shown in FIG. 35C. While tumors that formed in the control mice did not show MDA-7/IL-24 expression, both injected and uninjected tumors on Ad5.CTV-m7 treated mice showed expression of MDA-7/IL-24. These results support MDA-7/IL-24 as a potential therapeutic for treatment of breast cancer.

Ad.NG.m7 Suppresses Proliferation of Breast Cancer Cells More Robustly than Wild-Type Ad.mda-7/IL-24

Figure 36A:
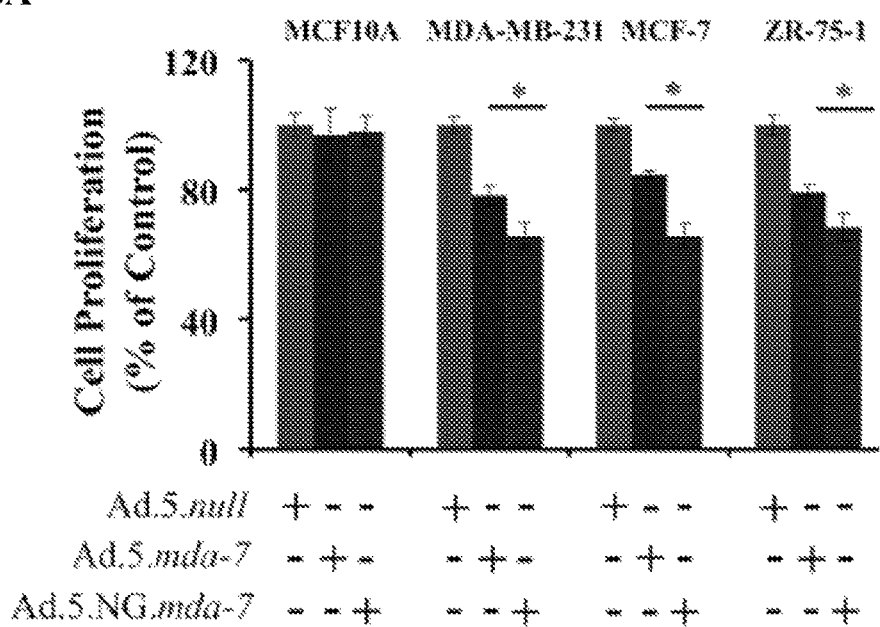
FIGS. 36A-36C show example results illustrating that Ad.NG.m7 suppresses proliferation of BCa cells more robustly than wild-type Ad.mda-7/IL-24. Human BCa cells and immortal primary mammary epithelial cells were infected with Ads expressing either mda-7/IL-24 or NG.m7 at an MOI of 2,000 VP. After 72-hr, cell proliferation (FIG. 36A) and apoptosis (FIG. 36B) were determined by MTT and Flow cytometry, respectively. *: statistical significance (P<0.05).
Figure 36B:
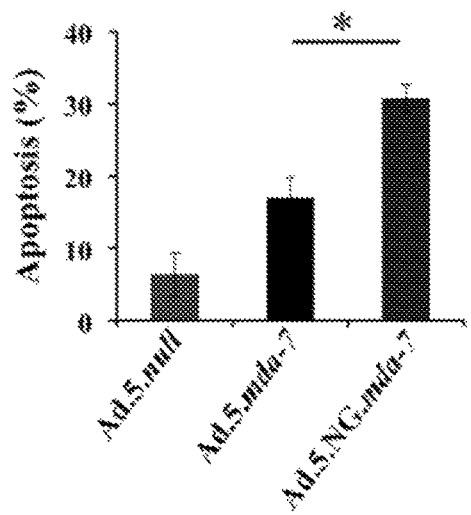
Figure 36C:
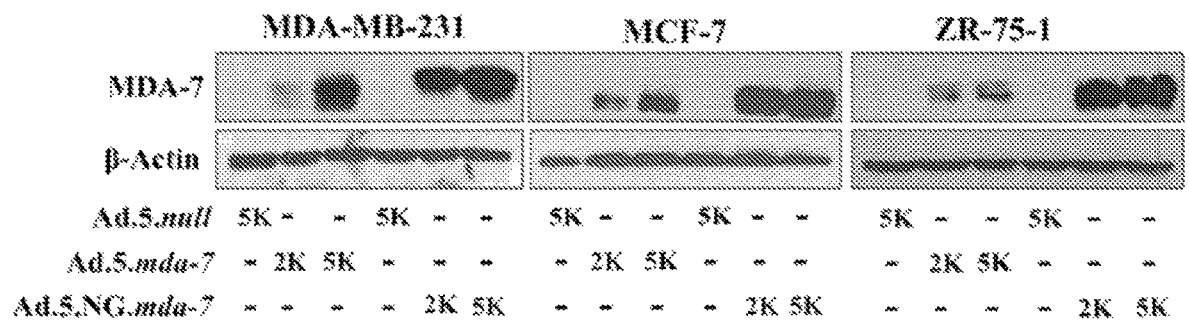

A non-replicating Adenovirus 5 vector in which NG.m7 is transcriptionally controlled by a CMV promoter (Ad.NG.m7) was developed. In this variant, MDA-7/IL-24 is linked to an insulin signal peptide and Lysine 122 was mutated to an Arginine by site directed mutagenesis. Three breast cancer cell lines (MDA-MB-231, MCF-7, ZR-751) and immortal primary human mammary epithelial (MCF10A) cells were infected with adenoviral vectors carrying wild type mda-7/IL-24 or NG.m7 at a multiplicity of infection (MOI) of 2000 VP (virus particles). Cell proliferation was evaluated by MTT assays (as described above) and the results presented in FIG. 36A. Both versions of MDA-7/IL-24 inhibited growth of the breast cancer cell lines (p<0.05 vs. control) without any detrimental effects on normal immortal human mammary epithelial cells. Quantitatively, NG.m7 caused significantly higher growth inhibition and cell killing (induction of apoptosis) in human cancer cells as measured by flow cytometry and shown in FIG. 36B. Infection of breast cancer cells with Ad.NG.m7 resulted in a significantly higher level of secreted protein in comparison with wild type Ad.mda-7/IL-24 as determined by Western blotting (FIG. 36C). These results provide evidence that NG.M7 has selective anti-cancer activity in human breast cancer cells.

Targeting MDA-7/IL-24 Protein Delivery

Figure 37A:
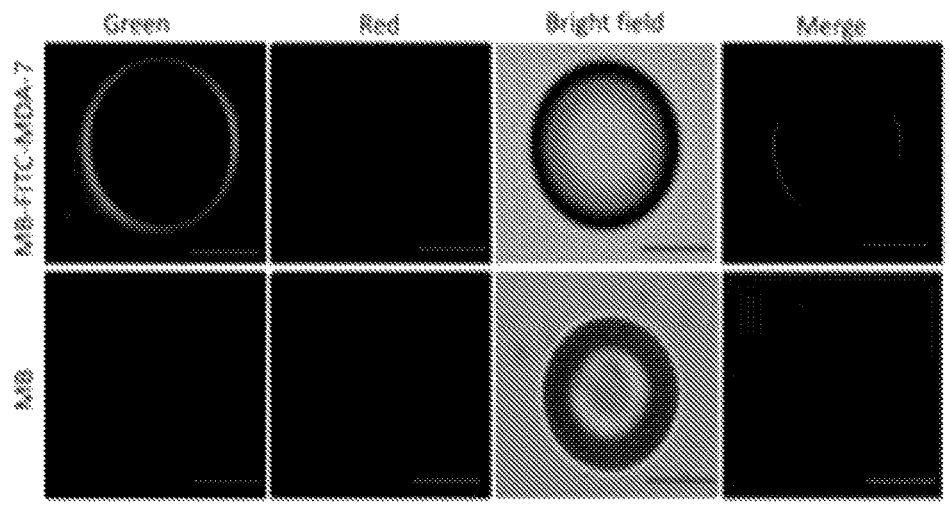
FIGS. 37A-37D show example results illustrating preparation of His-MDA-7 in complex with microbubbles (MBs) and generating decorated MBs (D-MBs).
Figure 37B:
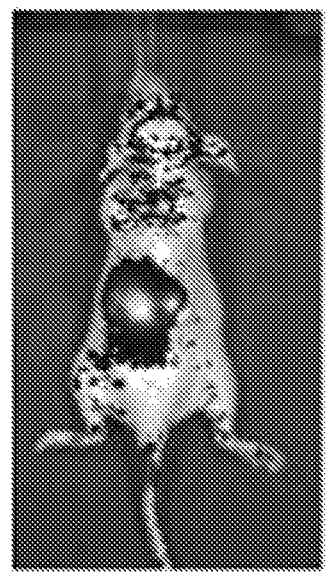

Microbubbles (MBs) and the Ultrasound Targeted Microbubble Destruction (UTMD) approach were used to deliver MDA-7/IL-24 protein in vivo to human tumor xenografts. To confirm the association of His-MDA-7 with MBs, Alexa Fluor 488 labeled His-MDA-7 was mixed and incubated with lyophilized MBs. The unincorporated labeled His-MDA-7 was removed by centrifugation and the MB (white layer) was mixed with 1 ml PBS and observed under a fluorescent microscope. The labeled His-MDA-7 (green fluorescence) was associated with the lipid shell of the MB (FIG. 37A). Tail vein injection of Alexa-Fluor-His-MDA-7/IL-24 into nude mice containing a DU-145 tumor xenograft followed by UTMD confirmed tumor targeting. DU-145, human prostate cancer cells, were established as xenografts in the left flank of nude mice. Alexa Fluor labeled His-MDA-7/MB complexes were injected through the tail vein and sonoporated in the tumor implanted in the left flank with an ultrasound portable SonoSite Micro-Maxx US platform (SonoSite) for 10 min. The fluorescent image was captured using Xenogen IVIS spectrum (FIG. 37B).

Figure 37C:
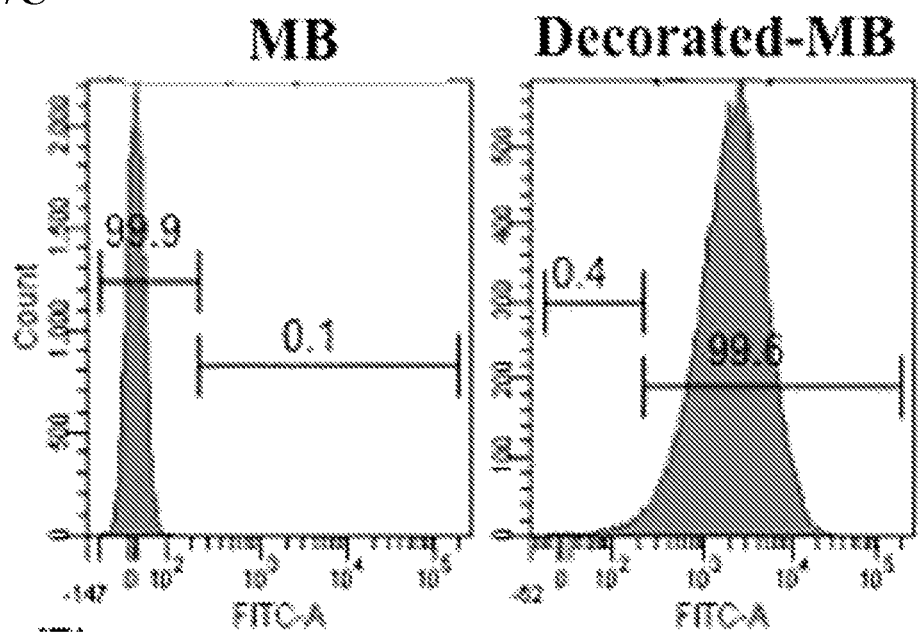

To achieve better payload delivery while retaining cancer specificity, MBs were decorated by adding a targeting antibody (VCAM-1) via a biotin-streptavidin spacer (D-MBs) (e.g. Ellegala et al.). To confirm complexation of VCAM-1 with the MB, biotinylated anti-VCAM-1 (B-VCAM-1) (100 µg) was incubated with Streptavidin microbubbles (MB-SA) (~$10^9$ MB particles) to form the complex Biotin-anti-V-CAM-1-Streptavidin-MB (MB-SA-B-anti-VCAM-1; D-MB). The preparation of the D-MB, both the D-MB as well as simple MB-SA, were mixed with Avidin-FITC, and flow-cytometry confirmed the formation of D-MB (FIG. 37C). These D-MBs were functionalized with an Ad.luc (Adenovirus expressing luciferase) and were evaluated by tail vein injection and UTMD in MMTV-PyMT mice (FIG.

Figure 37D:

37B). Upon ultrasound (sonoporation), the Ad.luc was released adjacent to the tumor niche. Since VCAM-1 was overexpressed in inflamed vascular endothelial cells and the tumor vasculature, this proof-of-concept with VCAM-1 bound D-MBs (FIG. 37B) demonstrated efficient delivery in MMTV-PyMT mice. D-MB complexed with Ad.luc was systemically injected via tail vein and sonoporated in the tumor region of MMTV-PyMT. Bioluminescence imaging (BLI) was done after 72-h of post injection of D-MB/Ad.luc using IVIS spectrum (FIG. 37D). These decorated MBs may be useful in delivering MDA-7/IL-24 protein (including variants) to primary tumors and metastatic sites in a breast cancer context. Delivery of polynucleotides and vectors encoding MDA-7/IL-24 protein, and delivery to other types of cancers are also contemplated.

Figure 38A:
FIGS. 38A-38B show example images illustrating enhanced eradication of mouse mammary tumor metastases by MDA-7/IL-24-producing T cells.
Figure 38B:
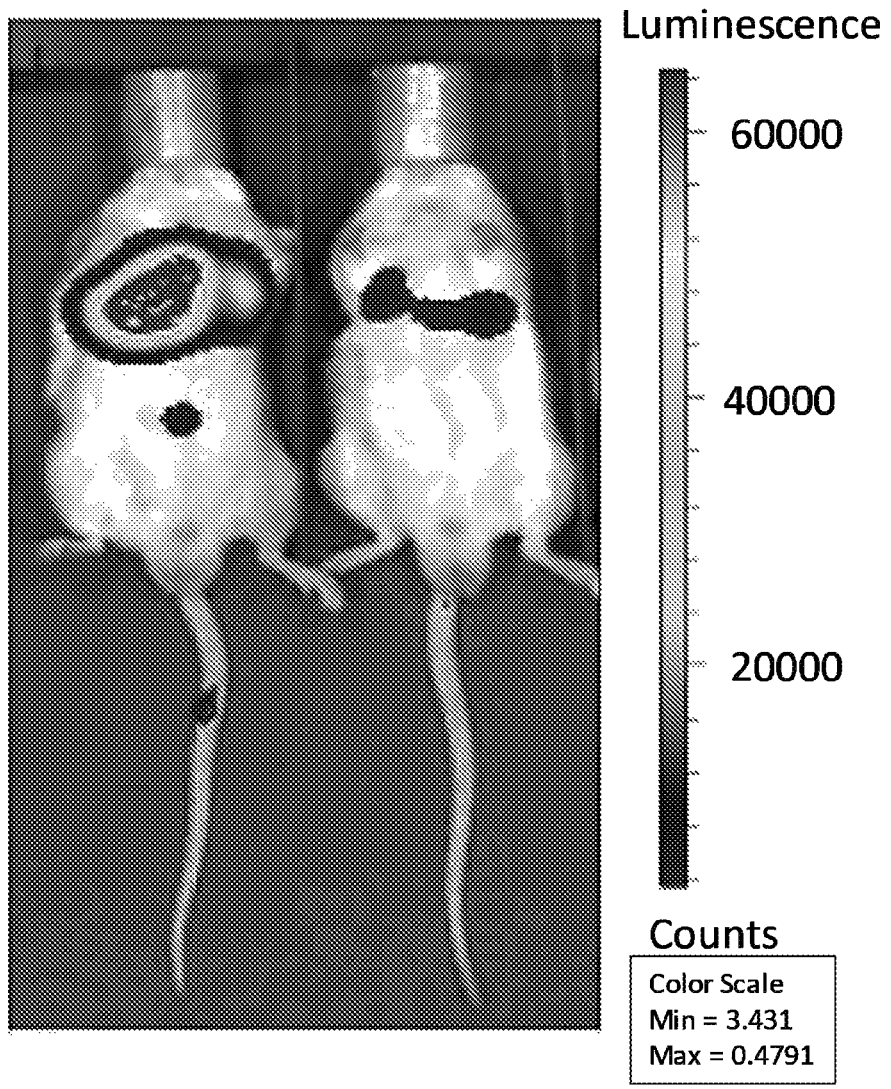

Enhanced Eradication of Mouse Mammary Tumor Metastases by MDA-7/IL-24-Producing T Cells T cells from 4T1-mammary tumor-bearing mice were reprogrammed and expanded by IL-7/IL-15, and engineered with a lentivirus encoding MDA-7/IL-24. Media of modified T cells was analyzed for MDA-7/IL-24 levels by immunoblotting (FIG. 38A). Mice were injected intravenously with $2.5 \times 10^5$ 4T1-Luc cells, followed by treatment with T cells engineered to produce MDA-7/IL-24(T-MDA-7) or T cells correspondingly modified with a control virus (T-vec). Tumors in the lungs were imaged two weeks later (FIG. 38B). Results showed that T cells genetically modified to express MDA-7/IL-24 were more effective than mock-modified T cells in eradicating lung metastases of mouse mammary tumors, suggesting that antigen and/or tumor-reactive T lymphocytes for adoptive T-cell therapy can target MDA-7/IL-24 selectively to breast cancer sites for potentially synergistic tumor eradication.

T Cell Engineering with a Lentivirus Expressing MDA-7/IL-24 or NG.M7

Figure 39:
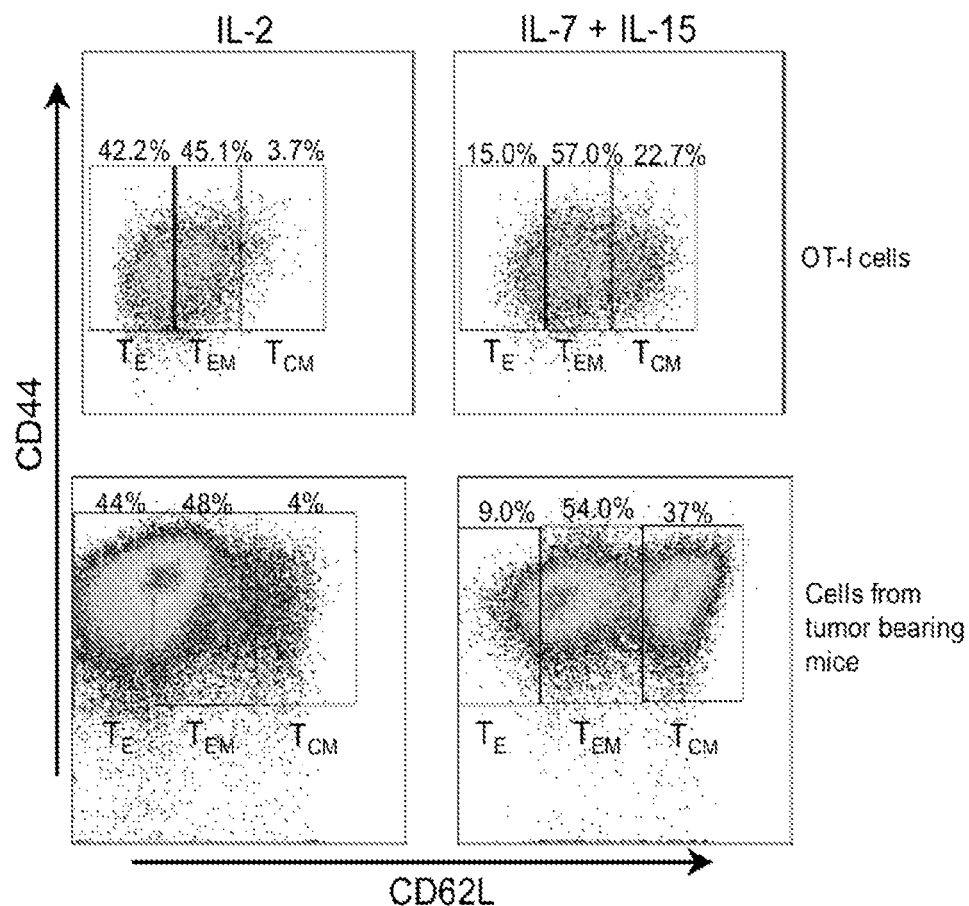
FIG. 39 shows example results illustrating that combination of IL-7 and IL-15 preferentially generates CD8+ T cells with a central memory phenotype. OVA-specific OT-I cells (upper) or lymphocytes from tumor-bearing mice (lower) were stimulated with Ionomycin (1 μM) and Bryostatin (5 nM) for 16 h. Cells were then cultured in the presence of IL-7/IL-15 (10 ng/ml) for 6 days. For conventional T cell expansion, lymphocytes were cultured in the presence of IL-2 (20 U/ml). FACS analysis was performed by gating on CD8+ T cells.

Tumor-reactive T lymphocytes (TILs or T cells from draining lymph nodes) were prepared from mice with established transplantable mammary tumors and expanded using an ex vivo protocol involving Bryostatin/Ionomycin and common γ-chain cytokines (IL-7/IL-15) as described in e.g. Kmieciak et al J Immunol 2011, Cha et al 2010, and Kmieciak et al JoVE 2011. As shown in FIG. 39, OVA-specific OT-I cells (upper panels) or lymphocytes from tumor-bearing mice (lower panels) were stimulated with Ionomycin (1 µM) and Bryostatin (5 nM) for 16 hours. Cells were then cultured in the presence of IL-7/IL-15 (10 ng/ml) for 6 days. For conventional T cell expansion, lymphocytes were cultured in the presence of IL-2 (20 U/ml) and FACS analysis was performed by gating on CD8+T cells. The data demonstrated that the combination of IL-7 and IL-15 preferentially generated CD8+T cells with a central memory phenotype (CD44+CD62Lhigh).

Figure 40:
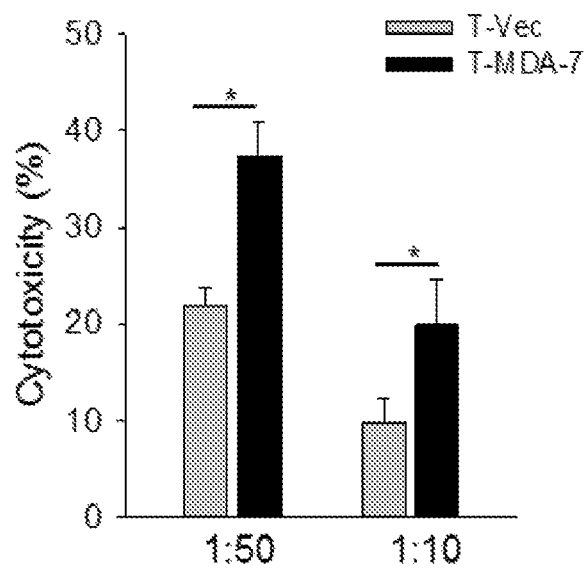
FIG. 40 shows example results illustrating that MDA-7/IL-24-engineered T cells display enhanced killing of BCa cells. T cells from MMTV-PyMT mice (C57BL/6 background) bearing mammary tumors were expanded and transduced with LV-MDA-7 (T-MDA-7) or LV-Vec (T-Vec), followed by co-culture with MMTV-PyMT (E0771) cells at indicated ratio for 20 h. Cytotoxicity was assayed by LDH assay. *, p<0.05.

The in vitro data presented in FIG. 40 demonstrated that MDA-7/IL-24-engineered T cells display enhanced killing of breast cancer cells. T cells from MMTV-PyMT mice (C57BL/6 background) bearing mammary tumors were expanded and transduced with LV-MDA-7 (T-MDA-7) or LV-Vec (T-Vec), followed by co-culture with MMTV-PyMT (E0771) cells at indicated ratio for 20 hours. Cytotoxicity was assayed by LDH assay. The data supports optimization of T cell engineering with a lentivirus expressing MDA-7/IL-24 or NG-m7.

MDA-7/IL-24 Therapy Enhances Immunogenicity of Mouse Mammary Tumors

Figure 41A:
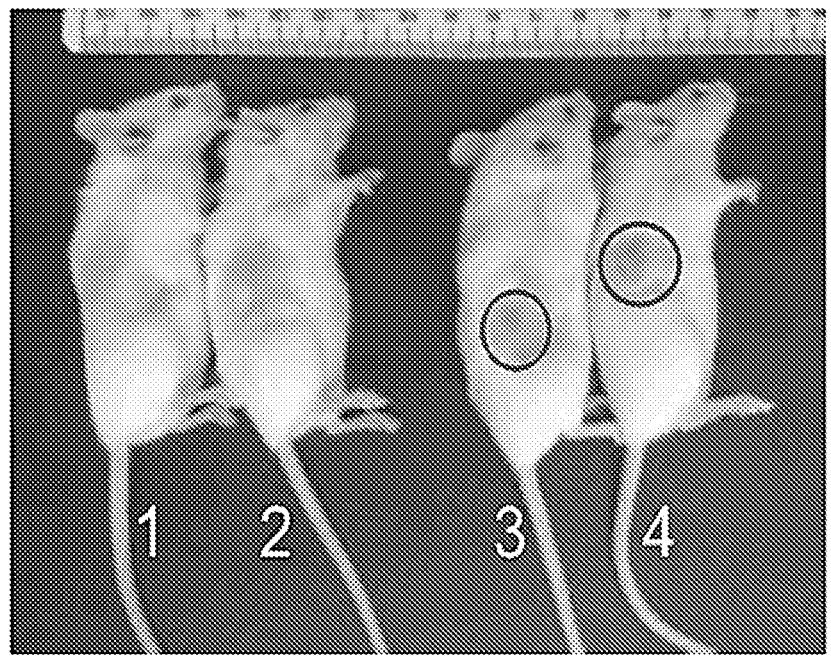
FIGS. 41A-41C show example images illustrating that MDA-7/IL-24 therapy enhances immunogenicity of mouse mammary tumors.
Figure 41B:
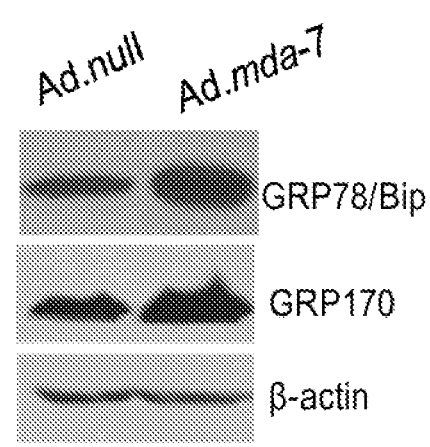
Figure 41C:
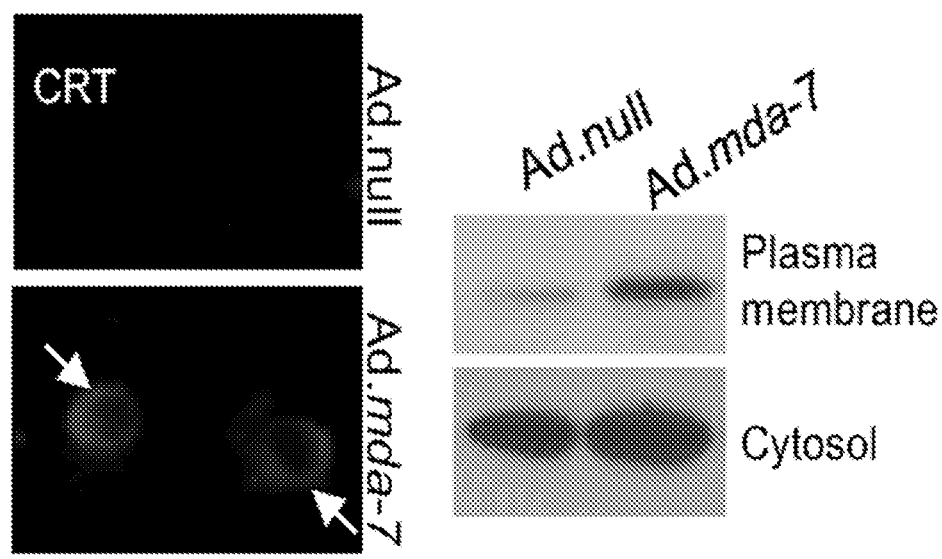

MDA-7/IL-24 has been shown to induce cancer cell death by binding to GRP78/BiP, a major ER-resident stress protein and molecular chaperone, and triggering ER stress signals in a cancer cell-specific manner. Immunization with poorly immunogenic 4T1 cells treated with Ad.mda-7 provided protection against tumor challenge as shown in FIG. 41A. Immunogenic breast cancer cell death was induced by MDA-7/IL-24 therapy. BALB/c mice were immunized with irradiated, Ad.mda-7 (mouse 1 and 2) or Ad.null (mouse 3 and 4) infected 4T1 cells (MOI=1), and then challenged with live 4T1 cells. The images were taken two weeks' post-tumor challenge. ER stress response was induced by MDA-7/IL-24 as indicated by upregulation of ER-resident chaperones as shown in FIG. 41B. MDA-7/IL-24 therapy triggers the surface presence of calreticulin (CRT) as assessed by immunofluorescence staining (FIG. 41C, left) and immunoblotting analysis of plasma membrane or cytosolic fractions (FIG. 41C, right). Taken together, these results demonstrated MDA-7/IL-24 therapy induced an ER stress response in breast cancer cells, indicated by upregulation of GRP78/BiP, GRP170, and calreticulin that resulted in immunogenic cancer cell death (ICD).

REFERENCES

Azab, B. M., Dash, R., Das, S. K., Bhutia, S. K., Sarkar, S., Shen, X. N., Quinn, B. A., Dent, P., Dmitriev, I. P., Wang, X. Y., Curiel, D. T., Pellecchia, M., Reed, J. C., Sarkar, D. & Fisher, P. B. Enhanced Prostate Cancer Gene Transfer and Therapy Using a Novel Serotype Chimera Cancer Terminator Virus (Ad.5/3-CTV). *J Cell Physiol* 229, 34-43 (2014).

Bhutia, S. K., Dash, R., Das, S. K., Azab, B., Su, Z. Z., Lee, S. G., Grant, S., Yacoub, A., Dent, P., Curiel, D. T., Sarkar, D. & Fisher, P. B. Mechanism of autophagy to apoptosis switch triggered in prostate cancer cells by antitumor cytokine melanoma differentiation-associated gene 7/interleukin-24. *Cancer Res* 70, 3667-3676 (2010).

Cha, E., Graham, L., Manjili, M. H. & Bear, H. D. IL-7+IL-15 are superior to IL-2 for the ex vivo expansion of 4T1 mammary carcinoma-specific T cells with greater efficacy against tumors in vivo. *Breast cancer research and treatment* 122, 359-369 (2010).

Dash, R., Azab, B., Quinn, B. A., Shen, X. N., Wang, X. Y., Das, S. K., Rahmani, M., Wei, J., Hedvat, M., Dent, P., Dmitriev, I. P., Curiel, D. T., Grant, S., Wu, B. N., Stebbins, J. L., Pellecchia, M., Reed, J. C., Sarkar, D. & Fisher, P. B. Apogossypol derivative BI-97C1 (Sabutoclax) targeting Mcl-1 sensitizes prostate cancer cells to mda-7/IL-24-mediated toxicity. *P Natl Acad Sci USA* 108, 8785-8790 (2011).

Dash, R., Bhutia, S. K., Azab, B., Su, Z. Z., Quinn, B. A., Kegelmen, T. P., Das, S. K., Kim, K., Lee, S. G., Park, M. A., Yacoub, A., Rahmani, M., Emdad, L., Dmitriev, I. P., Wang, X. Y., Sarkar, D., Grant, S., Dent, P., Curiel, D. T. & Fisher, P. B. mda-7/IL-24: a unique member of the IL-10 gene family promoting cancer-targeted toxicity. *Cytokine Growth Factor Rev* 21, 381-391 (2010).

Dash, R., Dmitriev, I., Su, Z. Z., Bhutia, S. K., Azab, B., Vozhilla, N., Yacoub, A., Dent, P., Curiel, D. T., Sarkar, D. & Fisher, P. B. Enhanced delivery of mda-7/IL-24 using a serotype chimeric adenovirus (Ad.5/3) improves therapeutic efficacy in low CAR prostate cancer cells. *Cancer Gene Ther* 17, 447-456 (2010).

Ellegala, D. B., Leong-Poi, H., Carpenter, J. E., Klibanov, A. L., Kaul, S., Shaffrey, M. E., Sklenar, J. & Lindner, J. R. Imaging tumor angiogenesis with contrast ultrasound and microbubbles targeted to alpha(v)beta3. *Circulation* 108, 336-341 (2003).

Gupta, P., Walter, M. R., Su, Z. Z., Lebedeva, I. V., Emdad, L., Randolph, A., Valerie, K., Sarkar, D. & Fisher, P. B. BiP/GRP78 is an intracellular target for MDA-7/IL-24 induction of cancer-specific apoptosis. *Cancer Res* 66, 8182-8191 (2006).

Fisher, P. B. Is mda-7/IL-24 a "magic bullet" for cancer? *Cancer Res* 65, 10128-10138 (2005).

Fisher, P. B., Gopalkrishnan, R. V., Chada, S., Ramesh, R., Grimm, E. A., Rosenfeld, M. R., Curiel, D. T. & Dent, P. mda-7/IL-24, a novel cancer selective apoptosis inducing cytokine gene: from the laboratory into the clinic. *Cancer Biol Ther* 2, S23-37 (2003)

Fisher, P. B., Sarkar, D., Lebedeva, I. V., Emdad, L., Gupta, P., Sauane, M., Su, Z. Z., Grant, S., Dent, P., Curiel, D. T., Senzer, N. & Nemunaitis, J. Melanoma differentiation associated gene-7/interleukin-24 (mda-7/IL-24): novel gene therapeutic for metastatic melanoma. *Toxicology and applied pharmacology* 224, 300-307 (2007).

Kantoff, P. W., Higano, C. S., Shore, N. D., Berger, E. R., Small, E. J., Penson, D. F., Redfern, C. H., Ferrari, A. C., Dreicer, R., Sims, R. B., Xu, Y., Frohlich, M. W., Schellhammer, P. F. & Investigators, I. S. Sipuleucel-T immunotherapy for castration-resistant prostate cancer. *N Engl J Med* 363, 411-422 (2010).

Kmieciak, M., Basu, D., Payne, K. K., Toor, A., Yacoub, A., Wang, X. Y., Smith, L., Bear, H. D. & Manjili, M. H. Activated NKT cells and NK cells render T cells resistant to myeloid-derived suppressor cells and result in an effective adoptive cellular therapy against breast cancer in the FVBN202 transgenic mouse. *J Immunol* 187, 708-717 (2011).

Kmieciak, M., Toor, A., Graham, L., Bear, H. D. & Manjili, M. H. Ex vivo expansion of tumor-reactive T cells by means of bryostatin 1/ionomycin and the common gamma chain cytokines formulation. *Journal of visualized experiments: JoVE* 47, 2381-2385 (2011).

Lebedeva, I. V., Sauane, M., Gopalkrishnan, R. V., Sarkar, D., Su, Z. Z., Gupta, P., Nemunaitis, J., Cunningham, C., Yacoub, A., Dent, P. & Fisher, P. B. mda-7/IL-24: exploiting cancer's Achilles' heel. *Mol Ther* 11, 4-18 (2005).

Matsuura, N., PuzonMcLaughlin, W., Irie, A., Morikawa, Y., Kakudo, K. & Takada, Y. Induction of experimental bone metastasis in mice by transfection of integrin alpha 4 beta 1 into tumor cells. *Am J Pathol* 148, 55-61 (1996).

Park, M. A., Walker, T., Martin, A. P., Allegood, J., Vozhilla, N., Emdad, L., Sarkar, D., Rahmani, M., Graf, M., Yacoub, A., Koumenis, C., Spiegel, S., Curiel, D. T., Voelkel-Johnson, C., Grant, S., Fisher, P. B. & Dent, P. MDA-7/IL-24-induced cell killing in malignant renal carcinoma cells occurs by a ceramide/CD95/PERK-dependent mechanism. *Mol Cancer Ther* 8, 1280-1291 (2009).

Rahmani, M., Mayo, M., Dash, R., Sokhi, U. K., Dmitriev, I. P., Sarkar, D., Dent, P., Curiel, D. T., Fisher, P. B. & Grant, S. Melanoma differentiation associated gene-7/interleukin-24 potently induces apoptosis in human myeloid leukemia cells through a process regulated by endoplasmic reticulum stress. *Molecular pharmacology* 78, 1096-1104 (2010).

Ramesh, R., Mhashilkar, A. M., Tanaka, F., Saito, Y., Branch, C. D., Sieger, K., Mumm, J. B., Stewart, A. L., Boquoi, A., Dumoutier, L., Grimm, E. A., Renauld, J. C., Kotenko, S. & Chada, S. Melanoma differentiation-associated gene 7/interleukin (IL)-24 is a novel ligand that regulates angiogenesis via the IL-22 receptor. *Cancer Res* 63, 5105-5113 (2003).

Sato, Y. The vasohibin family: a novel family for angiogenesis regulation. *J Biochem* 153, 5-11 (2013).

Sauane, M., Su, Z. Z., Dash, R., Liu, X., Norris, J. S., Sarkar, D., Lee, S. G., Allegood, J. C., Dent, P., Spiegel, S. & Fisher, P. B. Ceramide plays a prominent role in MDA-7/IL-24-induced cancer-specific apoptosis. *Journal of cellular physiology* 222, 546-555 (2010).

Schreiber, R. D., Old, L. J. & Smyth, M. J. Cancer immunoediting: integrating immunity's roles in cancer suppression and promotion. *Science* 331, 1565-1570 (2011).

Shrimali, R. K., Yu, Z., Theoret, M. R., Chinnasamy, D., Restifo, N. P. & Rosenberg, S. A. Antiangiogenic agents can increase lymphocyte infiltration into tumor and enhance the effectiveness of adoptive immunotherapy of cancer. *Cancer Res* 70, 6171-6180 (2010).

Tian H., Li L., Zhang B., Di J., Chen F., Li H., Liu J., Pei D., Zheng J. Critical role of lysine 123 in the ubiquitin-mediated degradation of MDA-7/IL-24. *J Interferon Cytokine Res*. 32(12), 575-582 (2012).

Topalian, S. L., Sznol, M., McDermott, D. F., Kluger, H. M., Carvajal, R. D., Sharfman, W. H., Brahmer, J. R., Lawrence, D. P., Atkins, M. B., Powderly, J. D., Leming, P. D., Lipson, E. J., Puzanov, I., Smith, D. C., Taube, J. M., Wigginton, J. M., Kollia, G. D., Gupta, A., Pardoll, D. M., Sosman, J. A. & Hodi, F. S. Survival, durable tumor remission, and long-term safety in patients with advanced melanoma receiving nivolumab. *J Clin Oncol* 32, 1020-1030 (2014).

Unger, E., Porter, T., Lindner, J. & Grayburn, P. Cardiovascular drug delivery with ultrasound and microbubbles. *Adv Drug Deliv Rev* 72, 110-126 (2014).

Wang, X. Y., Zuo, D., Sarkar, D. & Fisher, P. B. Blockade of cytotoxic T-lymphocyte antigen-4 as a new therapeutic approach for advanced melanoma. *Expert Opin Pharmacother* 12, 2695-2706 (2011)

Yee, C., Thompson, J. A., Byrd, D., Riddell, S. R., Roche, P., Celis, E. & Greenberg, P. D. Adoptive T cell therapy using antigen-specific CD8+ T cell clones for the treatment of patients with metastatic melanoma: in vivo persistence, migration, and antitumor effect of transferred T cells. *Proceedings of the National Academy of Sciences of the United States of America* 99, 16168-16173 (2002).

Yi, H., Guo, C., Yu, X., Gao, P., Qian, J., Zuo, D., Manjili, M. H., Fisher, P. B., Subjeck, J. R. & Wang, X. Y. Targeting the immunoregulator SRA/CD204 potentiates specific dendritic cell vaccine-induced T cell response and antitumor immunity. *Cancer Res* 71, 6611-6620 (2011).

Yu, X., Guo, C., Yi, H., Qian, J., Fisher, P. B., Subjeck, J. R. & Wang, X. Y. A multifunctional chimeric chaperone serves as a novel immune modulator inducing therapeutic antitumor immunity. *Cancer Res* 73, 2093-2103 (2013).

EMBODIMENTS

Embodiment 1. A polynucleotide encoding a fusion protein, wherein the fusion protein comprises an insulin signal peptide and an MDA-7/IL-24 protein Embodiment 2. The polynucleotide of embodiment 1, wherein the MDA-7/IL-24 protein comprises an amino acid sequence that is at least 90% identical to SEQ ID NO: 4.

Embodiment 3. The polynucleotide of embodiment 1 or 2, wherein the MDA-7/IL-24 protein comprises an amino acid sequence that is at least 90% identical to SEQ ID NO: 3.

Embodiment 4. The polynucleotide of any one of embodiments 1-3, wherein the MDA-7/IL-24 protein comprises a mutation corresponding to (a) a change of K122R relative to SEQ ID NO: 2, (b) a change of K73R relative to SEQ ID NO: 3, or (c) a change of K19R relative to SEQ ID NO: 4.

Embodiment 5. The polynucleotide of any one of embodiments 1-4, wherein the insulin signal peptide is a human insulin signal peptide.

Embodiment 6. The polynucleotide of any one of embodiments 1-5, wherein the insulin signal peptide comprises an amino acid sequence that is at least 90% identical to SEQ ID NO: 5.

Embodiment 7. The polynucleotide of any one of embodiments 1-6, wherein the polynucleotide comprises a nucleotide sequence that is at least 90% identical to any one of SEQ ID NOs: 6, 10-12, or 17.

Embodiment 8. The polynucleotide of any one of embodiments 1-7, wherein the MDA-7/IL-24 protein is capable of activating an IL-20/IL-22 receptor complex of a cancer cell.

Embodiment 9. The polynucleotide of any one of embodiments 1-8, wherein the MDA-7/IL-24 protein comprises an amino acid sequence of SEQ ID NO: 18.

Embodiment 10. The polynucleotide of any one of embodiments 1-9, wherein the polynucleotide does not encode amino acids 1-49 of SEQ ID NO: 2.

Embodiment 11. The polynucleotide of any one of embodiments 1, 2, or 4-10, wherein the polynucleotide does not encode amino acids 1-54 of SEQ ID NO: 3.

Embodiment 12. A vector comprising the polynucleotide of any one of embodiments 1-11.

Embodiment 13. The vector of embodiment 12, wherein the vector is a plasmid.

Embodiment 14. The vector of embodiment 12, wherein the vector is a virus.

Embodiment 15. The vector of embodiment 14, wherein the virus is an adenovirus or a lentivirus.

Embodiment 16. The vector of embodiment 15, wherein the virus is replication incompetent.

Embodiment 17. The vector of embodiment 15, wherein virus replication is under control of a cancer-specific promoter.

Embodiment 18. The vector of embodiment 17, wherein the cancer-specific promoter is a Progression Elevated Gene (PEG)-3 promoter.

Embodiment 19. A cell comprising the polynucleotide of any one of embodiments 1-11 or the vector of any one of embodiments 12-18.

Embodiment 20. The cell of embodiment 19, wherein the cell is an immune cell.

Embodiment 21. The cell of embodiment 20, wherein the immune cell is a T cell.

Embodiment 22. A composition comprising (a) the polynucleotide of any one of embodiments 1-11 or the vector of any one of embodiments 12-18, and (b) a pharmaceutically acceptable excipient.

Embodiment 23. The composition of embodiment 22, further comprising an Mcl-1 inhibitor.

Embodiment 24. The composition of embodiment 23, wherein the Mcl-1 inhibitor is BI-97D6, BI-97C1, UMI-77, Marinopyrrole A, or A-1210477.

Embodiment 25. The composition of any one of embodiments 22-24, further comprising a PI3K inhibitor.

Embodiment 26. The composition of embodiment 25, wherein the PI3K inhibitor is LY294002.

Embodiment 27. A method of treating cancer, the method comprising administering to a subject in need thereof the polynucleotide of any one of embodiments 1-11, the vector of any one of embodiments 12-18, or the composition of any one of embodiments 22-26.

Embodiment 28. The method of embodiment 27, further comprising administering an Mcl-1 inhibitor to said subject.

Embodiment 29. The method of embodiment 28, wherein the Mcl-1 inhibitor is BI-97D6, BI-97C1, UMI-77, Marinopyrrole A, or A-1210477.

Embodiment 30. The method of any one of embodiments 27-29, further comprising administering a PI3K inhibitor to said subject.

Embodiment 31. The method of embodiment 30, wherein the PI3K inhibitor is LY294002.

Embodiment 32. The method of any one of embodiments 27-31, wherein the cancer is prostate cancer, breast cancer, or lung cancer.

Embodiment 33. The method of any one of embodiments 27-32, wherein the prostate cancer comprises cancer cells having an increased expression of one or more of Mcl-1, RANKL, Bcl-2, Bcl-xL, and Akt, relative to normal prostate cells.

Embodiment 34. Use of a composition comprising the polynucleotide of any one of embodiments 1-11, the vector of any one of embodiments 12-18, the cell of any one of embodiments 19-21, or the composition of any one of embodiments 22-26 in the manufacture of a medicament for the treatment of cancer in a subject in need thereof.

Embodiment 35. A fusion protein comprising an insulin signal peptide and an MDA-7/IL-24 protein.

Embodiment 36. The fusion protein of embodiment 32, wherein the MDA-7/IL-24 protein comprises an amino acid sequence that is at least 90% identical to SEQ ID NO: 4.

Embodiment 37. The fusion protein of embodiment 32 or 36, wherein the MDA-7/IL-24 protein comprises an amino acid sequence that is at least 90% identical to SEQ ID NO: 3.

Embodiment 38. The fusion protein of any one of embodiments 32-37, wherein the MDA-7/IL-24 protein comprises a mutation corresponding to (a) a change of K122R relative to SEQ ID NO: 2, (b) a change of K73R relative to SEQ ID NO: 3, or (c) a change of K19R relative to SEQ ID NO: 4.

Embodiment 39. The fusion protein of any one of embodiments 32-38, wherein the insulin signal peptide is a human insulin signal peptide.

Embodiment 40. The fusion protein of any one of embodiments 32-39, wherein the insulin signal peptide comprises an amino acid sequence that is at least 90% identical to SEQ ID NO: 5.

Embodiment 41. The fusion protein of any one of embodiments 32-40, wherein the fusion protein has an amino acid sequence that is at least 90% identical to the amino acid sequence encoded by any one of SEQ ID NOs: 6, 10-12, or 17.

Embodiment 42. The fusion protein of any one of embodiments 32-41, wherein the MDA-7/IL-24 protein is capable of activating an IL-20/IL-22 receptor complex of a cancer cell.

Embodiment 43. The fusion protein of any one of embodiments 32-42, wherein the MDA-7/IL-24 protein comprises an amino acid sequence of SEQ ID NO: 18.

Embodiment 44. The fusion protein of any one of embodiments 32-43, wherein the fusion protein does not comprise amino acids 1-49 of SEQ ID NO: 2.

Embodiment 45. The fusion protein of any one of embodiments 32, 36, or 38-44, wherein the polynucleotide does not encode amino acids 1-54 of SEQ ID NO: 3.

What is claimed is:

1. A polynucleotide encoding a fusion protein, wherein the fusion protein comprises an insulin signal peptide and an MDA-7/IL-24 protein.
2. The polynucleotide of claim 1, wherein the MDA-7/IL-24 protein comprises an amino acid sequence that is at least 90% identical to SEQ ID NO: 4.
3. The polynucleotide of claim 2, wherein the MDA-7/IL-24 protein comprises a full-length mature MDA-7/IL-24 protein.
4. The polynucleotide of claim 3, wherein the MDA-7/IL-24 protein comprises the amino acid sequence of SEQ ID NO: 18.
5. The polynucleotide of claim 2, wherein the MDA-7/IL-24 protein comprises an amino acid sequence that is at least 90% identical to SEQ ID NO: 3.
6. The polynucleotide of claim 1, wherein the MDA-7/IL-24 protein comprises an amino acid sequence that is at least 90% identical to SEQ ID NO: 3.
7. The polynucleotide of claim 1, wherein the MDA-7/IL-24 protein comprises a mutation corresponding to K19R relative to SEQ ID NO: 4.
8. The polynucleotide of claim 1, wherein the insulin signal peptide is a human insulin signal peptide comprising an amino acid sequence at least 90% identical to SEQ ID NO: 5.
9. The polynucleotide of claim 1, wherein the insulin signal peptide comprises the amino acid sequence of SEQ ID NO: 5.
10. The polynucleotide of claim 1, wherein the polynucleotide comprises a nucleotide sequence that is at least 90% identical to any one of SEQ ID NOs: 6, 10-12, and 17.
11. The polynucleotide of claim 1, wherein the MDA-7/IL-24 protein is capable of activating an IL-20/IL-22 receptor complex of a cancer cell.
12. The polynucleotide of claim 1, wherein the polynucleotide does not encode amino acids 1-49 of SEQ ID NO: 2.
13. The polynucleotide of claim 1, wherein the polynucleotide does not encode amino acids 1-54 of SEQ ID NO: 3.
14. The polynucleotide of claim 1, wherein the polynucleotide comprises the nucleotide sequence of SEQ ID NO: 11.
15. A vector comprising the polynucleotide of claim 1.
16. The vector of claim 15, wherein the vector is:
(a) a plasmid;
(b) a virus;
(c) an adenovirus or a lentivirus;
(d) a replication incompetent virus; or
(e) a virus in which virus replication is under control of a cancer-specific promoter.
17. The vector of claim 16, wherein the vector is an adenovirus in which virus replication is under control of a cancer-specific promoter.
18. The vector of claim 11, wherein the cancer-specific promoter is a Progression Elevated Gene (PEG)-3 promoter.
19. A cell comprising the polynucleotide of claim 1.
20. The cell of claim 19, wherein the cell is an immune cell.
21. A composition comprising the polynucleotide of claim 1 and a pharmaceutically acceptable excipient.
22. A method of treating cancer, the method comprising administering to a subject in need thereof the polynucleotide of claim 1.
23. The method of claim 22, further comprising administering to the subject:
(a) an Mcl-1 inhibitor; or
(b) a PI3K inhibitor.
24. The method of claim 22, wherein:
(a) the cancer is prostate cancer, breast cancer, or lung cancer; or
(b) the cancer comprises prostate cancer cells having an increased expression of one or more of Mcl-1, RANKL, Bcl-2, Bcl-xL, and Akt relative to normal prostate cells.
25. The method of claim 22, wherein the MDA-7/IL-24 protein comprises an amino acid sequence that is at least 90% identical to SEQ ID NO: 4.
26. The method of claim 25, wherein the MDA-7/IL-24 protein comprises the amino acid sequence of SEQ ID NO: 18.
27. The method of claim 22, wherein the MDA-7/IL-24 protein comprises an amino acid sequence that is at least 90% identical to SEQ ID NO: 3.
28. The method of claim 22, wherein the MDA-7/IL-24 protein comprises a mutation corresponding to K19R relative to SEQ ID NO: 4.
29. The method of claim 22, wherein the insulin signal peptide is a human insulin signal peptide comprising an amino acid sequence at least 90% identical to SEQ ID NO: 5.
30. The method of claim 22, wherein the insulin signal peptide comprises the amino acid sequence of SEQ ID NO: 5.
31. The method of claim 22, wherein the polynucleotide comprises the nucleotide sequence of SEQ ID NO: 11.
32. The method of claim 22, wherein the polynucleotide is comprised in an adenovirus vector in which virus replication is under control of a cancer-specific promoter.
33. The method of claim 32, wherein the cancer-specific promoter is a Progression Elevated Gene (PEG)-3 promoter.

* * * * *